US010420748B2

(12) United States Patent
Marschke et al.

(10) Patent No.: US 10,420,748 B2
(45) Date of Patent: *Sep. 24, 2019

(54) METHODS OF TREATMENT ASSOCIATED WITH THE GRANULOCYTE COLONY-STIMULATING FACTOR RECEPTOR

(71) Applicant: LIGAND PHARMACEUTICALS INCORPORATED, San Diego, CA (US)

(72) Inventors: Keith B. Marschke, La Jolla, CA (US); Lin Zhi, La Jolla, CA (US)

(73) Assignee: LIGAND PHARMACEUTICALS INCORPORATED, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/908,504

(22) Filed: Feb. 28, 2018

(65) Prior Publication Data

US 2018/0185333 A1    Jul. 5, 2018

Related U.S. Application Data

(63) Continuation of application No. 14/775,587, filed as application No. PCT/US2014/022721 on Mar. 10, 2014, now Pat. No. 9,962,370.

(60) Provisional application No. 61/913,111, filed on Dec. 6, 2013, provisional application No. 61/790,548, filed on Mar. 15, 2013.

(51) Int. Cl.
| | |
|---|---|
| *A61K 31/4045* | (2006.01) |
| *A61K 31/4152* | (2006.01) |
| *A61K 45/06* | (2006.01) |
| *A61K 31/41* | (2006.01) |
| *A61K 31/4155* | (2006.01) |
| *A61K 31/454* | (2006.01) |
| *A61N 5/10* | (2006.01) |
| *G01N 33/50* | (2006.01) |
| *A61K 31/40* | (2006.01) |
| *A61K 31/4015* | (2006.01) |

(52) U.S. Cl.
CPC .......... *A61K 31/4045* (2013.01); *A61K 31/41* (2013.01); *A61K 31/4152* (2013.01); *A61K 31/4155* (2013.01); *A61K 31/454* (2013.01); *A61K 45/06* (2013.01); *A61N 5/10* (2013.01); *G01N 33/5011* (2013.01); *A61K 31/40* (2013.01); *A61K 31/4015* (2013.01)

(58) Field of Classification Search
CPC .............................. A61K 31/40; A61K 31/4015
USPC .................................................. 514/418, 424
See application file for complete search history.

(56) References Cited

U.S. PATENT DOCUMENTS

| | | | |
|---|---|---|---|
| 3,116,282 A | * | 12/1963 | Hunter ................... C07H 19/06 536/28.5 |
| 6,737,434 B2 | | 5/2004 | Tokizawa et al. |
| 7,026,334 B1 | | 4/2006 | Takemoto et al. |
| 9,962,370 B2 | * | 5/2018 | Marschke .......... A61K 31/4152 |
| 2006/0116417 A1 | | 6/2006 | Chen et al. |
| 2008/0139621 A1 | | 6/2008 | Spencer et al. |
| 2014/0296292 A1 | | 10/2014 | Zhi |

FOREIGN PATENT DOCUMENTS

| | | | |
|---|---|---|---|
| CA | 2323111 A1 * | 10/1999 | ........... C07D 209/34 |
| EP | 1 647 553 | 4/2006 | |
| EP | 1 655 291 | 5/2006 | |
| EP | 2 025 671 | 2/2009 | |
| JP | 2003-267869 | 9/2003 | |
| WO | WO 2001/89457 | 11/2001 | |
| WO | WO 2003/037905 | 5/2003 | |
| WO | WO 2003/103686 | 12/2003 | |
| WO | WO 2004/033433 | 4/2004 | |
| WO | WO 2004/043353 | 5/2004 | |
| WO | WO 2004/096154 | 11/2004 | |
| WO | WO 2005/007651 | 1/2005 | |
| WO | WO 2005/014561 | 2/2005 | |
| WO | WO 2006/033005 | 3/2006 | |
| WO | WO 2006/047344 | 5/2006 | |
| WO | WO 2007/004038 | 1/2007 | |
| WO | WO 2007/036769 | 4/2007 | |
| WO | WO 2007/054783 | 5/2007 | |
| WO | WO 2007/062078 | 5/2007 | |

(Continued)

OTHER PUBLICATIONS

Amir et al., 2012, Synthesis and antimicrobial activity of pyrazolinones and pyrazoles having benzothiazole moiety, Medicinal Chemistry Research, 21(7):1261-1270.
Bains and Tacke, Silicon chemistry as a novel source of chemical diversity in drug design, Curr. Opin. Drug Discov Devel. 6(4):526-43 (2003).
Bains et al., 2003, Silicon chemistry as a novel source of chemical diversity in drug design, Curr. Opin. Drug Discov Devel. 6(4):526-543.
Berge et al., Jan. 1977, Pharmaceutical Salts, J. Pharm. Sci. 66(1):1-19.

(Continued)

*Primary Examiner* — Kevin E Weddington
(74) *Attorney, Agent, or Firm* — Knobbe, Martens, Olson & Bear LLP

(57) ABSTRACT

Some embodiments include methods for treating, preventing, reversing, halting, or slowing the progression of cancer, comprising administering to a subject in need thereof an effective amount of one or more chemotherapeutic agents, or a pharmaceutically acceptable salt thereof, or a pharmaceutical composition, wherein at least one of the chemotherapeutic agents is a cytotoxic granulocyte colony-stimulating factor receptor (GCFR) modulator. Methods are also disclosed for treating, preventing, reversing, halting, or slowing the progression of a hematopoietic disorder, comprising administered a therapeutically effective cytotoxic amount of a GCFR modulator to a subject in need thereof.

14 Claims, 3 Drawing Sheets

(56) References Cited

FOREIGN PATENT DOCUMENTS

| | | |
|---|---|---|
| WO | WO 2007/106564 | 9/2007 |
| WO | WO 2008/101141 | 8/2008 |
| WO | WO 2009/103218 | 8/2009 |
| WO | WO 2013/074459 | 5/2013 |

OTHER PUBLICATIONS

Bighley et al., 1996, Salt forms of drugs and absorption, in Encyclopedia of Pharmaceutical Technology, Swarbrick et al. eds., Marcel Dekker, Inc., New York, pp. 453-499.

Boyd and Paull, Some Practical Considerations and Applications of the National Cancer Institute In Vitro Anticancer Drug Discovery Screen, Drug. Dev. Res. 34:91-109 (1995).

Boyd et al., 1995, Some practical considerations and applications of the National Cancer Institute in vitro anticancer drug discovery screen, Drug Development Research, 34:91-109.

Doyle et al., Mar. 14, 2003, Selective binding and oligomerization of the murine granulocyte colony-stimulating factor receptor by a low molecular weight, nonpeptidyl ligand. The Journal of Biological Chemistry, 278(11):9426-9434.

Duffy et al., Jan. 2001, Hydrazinonaphthalene and azonaphthalene thrombopoetin mimics are nonpeptidyl promoters of megakaryocytopoiesis, J. Med. Chem. 44:3730-3745.

Erickson-Miller et al., 2004, Species specificity and receptor domain interaction of small molecule TPO receptor agonists. Blood (ASH Annual Meeting Abstracts) 2004 104: Abstract 2909.

Fingl et al. 1975, General Principles (Chapter 1) in The Pharmacological Basis of Therapeutics, Goodman et al., eds., MacMillan Publishing Co., Inc., New York, pp. 1-46.

Golub, et al, Molecular Classificiaton of Cancer: Class Discovery and Class Prediction by Fene Expression Monitoring, Science, 286:531-537 (1999).

Gould, 1986, Salt selection for basic drugs, International Journal of Pharmaceutics, 33:201-217.

Gowri et al., 2012, DNA binding and cytotoxicity of newly synthesized schiff base (Z)-4-(((2-hydroxyphenyl) amino) (phenyl)methylene)-3-methyl-1-phenyl-1H-pyrazol-5(4H)-one and it analogues, International Journal of Applied Biology and Pharmaceutical Technology, 3(4):327-337.

Gowri, M. et al, DNA Binding and Cytotoxicity of Newly Synthesized Schiff Base(Z)-4(((2-hyrdoxyphenyl)amino)(phenyl)methyl1-1-phenyl-1H-pyrazol-5(4H)-one and its Analogues, Intl J Applied Bio and Pharma Tech 3(4):327-337 (2012).

Greene et al., eds., Protective Groups in Organic Synthesis, 3$^{rd}$ Ed., John Wiley & Sons, New York, NY, 1999.

http://en.wikipedia.org/wiki/Cancer downloaded Jul. 6, 2007.

http://www.nlm.nih.gov/medlineplus/print/cancer.html downloaded Jul. 6, 2007.

International Search Report and Written Opinion dated Jul. 28, 2014 in PCT/US2014/022721.

International Search Report dated Feb. 14, 2013 received in International Application No. PCT/US2012/064706.

Komatsu et al, Jan. 1, 1991, Establishment and characterization of a human leukemic cell line with megakaryocytic features: dependency on granulocyte-macrophage colony-stimulating factor, interleukin 3, or erythropoietin for growth and survival, Cancer Research, 51:341-348.

Kumar et al., Jan. 9, 2011, Design, synthesis and evaluation of 3-methylene-substituted indolinones as antimalarials, Europ. J. Med. Chem., 46(3):927-933.

Kusano et al., Feb. 1, 2004, A potential therapeutic role for small nonpeptidyl compounds that mimic human granulocyte colony-stimulating factor, Blood, 103(3):836-842.

Lala, et al, Rolse of nitric oxide in tumor progression: Lessons from Experimental tumors, Cancer and Metastasis Reviews 17(1):91-106 (1998).

Lu et al., Mar. 17, 2006, Active conformation of the erythropoietin receptor: random and cycteine-scanning mutagenesis of the extracellular juxtamembrane and transmembrane domains. The Journal of Bioloigcal Chemistry, 281(11):7002-7011.

Lu X, et al. Active conformation of the erythropoietin receptor: Random and cycteine-scanning mutagenesis of the extracellular juxtamembrane and transmembrane domains. JBC 281:7002-7011 (2006).

Monfardini et al., Jan. 2002, Structure-based design of mimetics for granulocyte-macrophage colony stimulating factor (GM-CSF), Current Pharmaceutical Design, 8(24):2185-2199.

Plo et al. Jul. 20, 2009, An activating mutation in the CSF3R gene induces a hereditary chronic neutrophilia, The Journal of Experimental Medicine, 206:1701-1707.

Plo I, et al. An activating mutation in the CSF3R gene induces a hereditary chronic neutrophilia. JEM 206:1701-1707 (2009).

Praveen et al., 2011, Design, synthesis and evaluation of 3-methylene-substituted indolinones as antimalarials, European Journal of Medicinal Chemistry, 46(3):927-933 (Abstract).

Reaxys Database accession No. 36649, 1968, Toda et al., Nippon Kagaku Zasshi, 81:1292, 1298.

Sambrook et al. 1989, Molecular Cloning: A Laboratory Manual (2d ed.), Cold Spring Harbor Laboratory Press, Cold Spring Harbor, N.Y.

Skehan et al., Jul. 4, 1990, New colorimetric cytotoxicity assay for anticancer-drug screening, Journal of the National Cancer Institute, 82(13):1107-1112.

Skehan, et al., New Colorimetric Cytotoxicity Assay for Anticancer-Drug Screening, J. Natl. Cancer Inst., 82:1107-1112 (1990).

Stahl et al., eds., 2002, Handbook of Pharmaceutical Aalts: Properties, Selection and Use, Verlag Helvetica Chimica Acta, Zurich, Switzerland.

Tacke and Zilch, Sila-substitution—a useful strategy for drug design? Endeavour, New Series, 10:191-197 (1986).

Tacke et al., 1986, Sila-substitution—a useful strategy for drug design? Endeavour, New Series, 10(4):191-197.

Tamada et al., Feb. 28, 2006, Homodimeric cross-over structure of the human granulocyte colony-stimulating factor (GCSF) receptor signaling complex, PNAS, 103(9):3135-3140.

Tamada T, et al., Homodimeric cross-over structure of the human GCSF receptor signaling complex. PNAS 103:3135-3140 (2006).

Tang et al., Oct. 2010, Novel indoline-1- or 3,4-dihydroquinoline-1(2h)-substituted carbothiohydrazides as TPO receptor agonists, Bioorg. Med. Chem. Lett., 29(19):5670-5672.

Tian et al., Jul. 10, 1998, A small, nonpeptidyl mimics of granulocyte-colony-stimulating factor, Science, 281:257-259.

* cited by examiner

METHODS OF TREATMENT ASSOCIATED WITH THE GRANULOCYTE COLONY-STIMULATING FACTOR RECEPTOR

CROSS-REFERENCE TO RELATED APPLICATIONS

This application is a continuation of U.S. application Ser. No. 14/775,587 filed Sep. 11, 2015 which is the U.S. National Phase of International Application No. PCT/US2014/022721 which was published in English on Sep. 25, 2014 as WO 2014/150252 which claims the benefit of priority to U.S. Prov. App. No. 61/790,548, filed Mar. 15, 2013, and U.S. Prov. App. No. 61/913,111, filed Dec. 6, 2013, which are each expressly incorporated by reference in its entirety.

FIELD OF THE INVENTION

Granulocyte colony-stimulating factor receptor (GCFR) modulators for treating certain diseases such as cancer and/or reducing cellular proliferation.

BACKGROUND OF THE INVENTION

Granulocyte colony-stimulating factor (GCSF) is one of the hematopoietic growth factors with multifunctional activities. As a glycoprotein, GCSF plays important regulatory functions in the processes of maturation, proliferation, differentiation, and functional activation of granulocyte precursors and mature granulocytes in the bone marrow. It is able to augment white blood cell production when bone marrow dysfunction exists. Recombinant DNA technology has made it possible to clone the genes responsible for GCSF and to develop pharmaceutical products to treat a number of human hematopoietic conditions and disorders such as neutropenia and hematopietic stem cell transplantation.

Human GCSF (hGCSF) protein has a molecular mass of 19.6 kDa and exerts its biological functions through binding to the human GCSF receptor (hGCSFR), a single transmembrane protein with a large extracellular region that consists of an immunoglobulin-like (Ig-like) domain, a cytokine receptor homology (CRH) domain, and three fibronectin type III domains. Binding of GCSF to the extracellular Ig-like and CRH domains of the receptor triggers receptor homodimerization with a 2:2 stoichiometry of hGCSF/hGCSFR (Tamada T, et al. 2006 Homodimeric cross-over structure of the human GCSF receptor signaling complex. PNAS 103:3135-3140). The dimerization results in activation of intracellular Janus tyrosine kinase-signal transducers and activators of transcription (Jak-Stat) type signaling cascade. The signaling transfer of hematopoietic factor receptors from extracellular region to intracellular cascades has been suggested to be via conformational changes of the receptor dimer in TM domains. It has been demonstrated that the dimeric erythropoietin (EPO) receptor can be activated by mutations at the TM domain in the absence of the natural ligand EPO, a hematopoietic growth factor regulating red blood cell production (Lu X, et al. 2006 Active conformation of the erythropoietin receptor: Random and cycteine-scanning mutagenesis of the extracellular juxtamembrane and transmembrane domains. JBC 281:7002-7011). Patients with mutations in TM domain of hGCSFR have experienced chronic neutrophilia due to the receptor constitutive activation (Plo I, et al. 2009 An activating mutation in the CSF3R gene induces a hereditary chronic neutrophilia. JEM 206:1701-1707).

Several techniques for treating cancer are known in the art. Such techniques include, but are not limited to chemotherapy, radiation therapy, surgery, and transplantation. Many of these techniques, however, have undesirable side effects and varying success rates. Indeed, U.S. statistics for 2012 indicate that there will be an estimated 1,638,910 new cases of cancer (not including non-melanoma skin cancers) and 577,190 estimated deaths from cancer. Therefore, a need exists to develop new methods for treating cancer and/or diseases associated with cellular proliferation. While certain GCSF modulators have been clinically approved for the treatment of chemotherapy-induced neutropenia, thereby treating abnormally low numbers of neutrophils in a cancer patient, we have surprisingly discovered a new class of GCSF modulators that are cytotoxic to cancer cells.

SUMMARY OF THE INVENTION

Methods are disclosed for treating, preventing, reversing, halting, or slowing the progression of cancer, comprising administering to a subject in need thereof an effective amount of one or more chemotherapeutic agents, or a pharmaceutically acceptable salt thereof, or a pharmaceutical composition, wherein at least one of the chemotherapeutic agents is a cytotoxic granulocyte colony-stimulating factor receptor (GCFR) modulator.

Methods are also disclosed for treating, preventing, reversing, halting, or slowing the progression of a hematopoietic disorder, comprising administered a therapeutically effective cytotoxic amount of a GCFR modulator to a subject in need thereof. In some embodiments, the GCFR modulator is administered to a subject in need thereof at an interval that achieves a therapeutically effective plasma concentration of the modulator in the subject's bloodstream over a period of time.

Methods are also disclosed for treating, preventing, reversing, halting, or slowing the progression of a hematopoietic disorder, comprising administering a therapeutically effective amount of a GCFR modulator to a subject in need thereof at an interval that achieves a therapeutically effective plasma concentration of the modulator in the subject's bloodstream over a period of time. In some embodiments, the period of time is greater than 1 hour. In some embodiments, the period of time is greater than 3 hours. In some embodiments, the period of time is greater than 6 hours. In some embodiments, the period of time is greater than 9 hours. In some embodiments, the period of time is greater than 1 day. In some embodiments, the period of time is greater than 2 days. In some embodiments, the period of time is greater than 3 days. In some embodiments, the period of time is greater than 1 week. In some embodiments, the period of time is less than 1 week.

In some embodiments, the interval that achieves a therapeutically effective plasma concentration of the modulator is dosing more than one time daily. In some embodiments, the interval that achieves a therapeutically effective plasma concentration of the modulator is dosing more than two times daily. In some embodiments, the interval that achieves a therapeutically effective plasma concentration of the modulator is dosing 2-6 times daily. In some embodiments, the interval that achieves a therapeutically effective plasma concentration of the modulator is dosing 2-5 times daily. In some embodiments, the interval that achieves a therapeutically effective plasma concentration of the modulator is dosing 2-4 times daily. In some embodiments, the interval that achieves a therapeutically effective plasma concentration of the modulator is dosing two, three, four, five, or six times daily. In some embodiments, wherein the interval that achieves a therapeutically effective plasma concentration of the modulator is dosing three times daily. In some embodiments, the GCFR modulator is administered at a first interval for 1-5 days, followed by administration at a second interval that is different from the first interval. In some embodiments, the GCFR modulator is administered at the first interval for 2, 3, 4, or 5 days, and the administration at the second interval is once daily dosing. In some embodiments, the GCFR modulator is administered at the first interval for three days, and the administration at the second interval is once daily dosing. In some embodiments, the therapeutically effective plasma concentration of the modulator is the in vitro $EC_{50}$ of the modulator.

In some embodiments, about 0.5-4 mg of the GCFR modulator per kg of the subject's body weight is administered to the subject at each interval. In some embodiments, about 1-3 mg of the GCFR modulator per kg of the subject's body weight is administered to the subject at each interval. In some embodiments, about 2 mg of the GCFR modulator per kg of the subject's body weight is administered to the subject at each interval.

In some embodiments, the hematopoietic disorder is a granulocytopenia. In some embodiments, the hematopoietic disorder is neutropenia.

In some embodiments, the subject is diagnosed as having cancer. In some embodiments, the subject is undergoing cancer treatment. In some embodiments, the subject is in need of both hematopoietic disorder treatment and cancer treatment.

Some embodiments are disclosed in which the GCFR modulator is a GCFR agonist or partial agonist. Other embodiments are disclosed in which the cancer is a cancer of the blood, lung, kidney, or liver. In some embodiments, the cancer is a cancer of the breast, skin, or plasma cells. In some embodiments, the cancer is leukemia, non-small cell lung cancer, colon cancer, CNS cancer, skin cancer, ovarian cancer, renal cancer, prostate cancer, breast cancer, or a myeloma. In some embodiments, the cancer is leukemia, non-small cell lung cancer, colon cancer, CNS cancer, melanoma, ovarian cancer, renal cancer, prostate cancer, multiple myeloma, or breast cancer. In some embodiments, the cancer is a lung cancer, a liver cancer, a kidney cancer, a breast cancer, a melanoma, or a myeloma. In some embodiments, the cancer is leukemia. In some embodiments, the leukemia is chronic lymphocytic leukemia (CLL), chronic myeloid leukemia (CML), acute lymphocytic leukemia (ALL), acute myeloid leukemia (AML), T-cell prolymphocytic leukemia, large granular lymphocytic leukemia, adult T-cell leukemia, juvenile myelomonocytic leukemia, or hairy cell leukemia. In some embodiments, the leukemia is chronic leukemia or acute leukemia. In some embodiments, the leukemia is acute myeloid leukemia. In some embodiments, the leukemia is lymphocytic leukemia or myelogenous leukemia. In some embodiments, the GCFR modulator is cytotoxic to white blood cells. In some embodiments, the subject has neutropenia.

Other embodiments are disclosed in which the cytotoxic GCFR modulator, or a pharmaceutically acceptable salt thereof, or a pharmaceutical composition thereof is administered in combination with one or more additional therapeutic regimens. In some embodiments, the additional therapeutic regimen is selected from the group consisting of chemotherapy, bone marrow transplantation, and radiation therapy. In some embodiments, the additional therapeutic regimen is chemotherapy. In some embodiments, the chemotherapy comprises administering an agent selected from the group consisting of alkylating agents, anthracyclines, cytoskeletal disruptors, epothilones, histone deacetylase inhibitors, topoisomerase inhibitors, kinase inhibitors, monoclonal antibodies, nucleotide analogs, peptide antibiotics, platinum-based agents, retinoids, and vinca alkaloids. In some embodiments, the chemotherapy comprises administering one or more agents selected from the group consisting of gemcitabine, cytarabine, cisplatin, methotrexate, 6-mercaptopurine, chlorambucil, cyclophosphamide, fludarabine, pentostatin, cladribine, imatinib, rituximab, interferon-alpha, doxorubicin, vincristine, prednisone, etoposide, bleomycin, or Alemtuzumab In some embodiments, the cytotoxic GCFR modulator is selected by measuring a biomarker in the patient. In some embodiments, the biomarker is a cellular response to the GCFR agonist or partial agonist. In some embodiments, the cellular response is cytotoxicity. In some embodiments, the method further comprises selecting one or more chemotherapeutic agents by subjecting a sample from the patient to a companion diagnostic device. In some embodiments, the companion diagnostic device measures a biomarker in the patient. In some embodiments, the biomarker is a cellular response to one or more chemotherapeutic agents. In some embodiments, the cellular response is cytotoxicity Some methods include a cytotoxic GCFR modulator of Formula (I), (II), (III), or (IV):

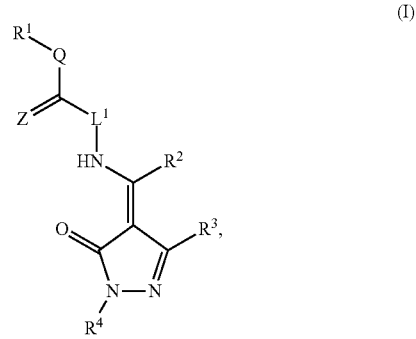

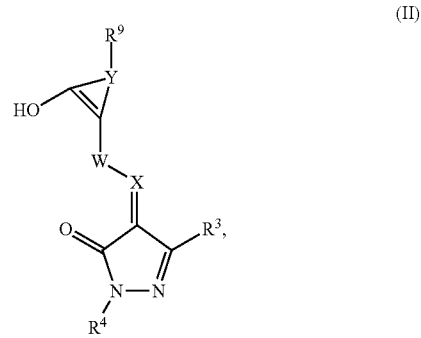

-continued

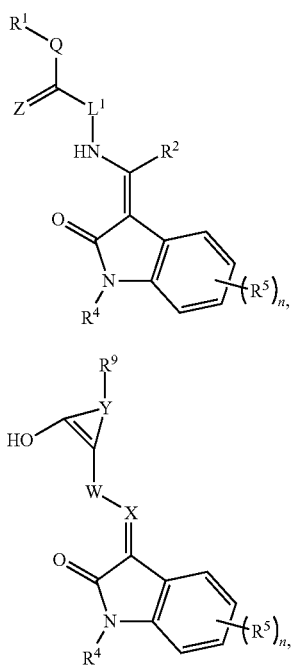

a tautomer thereof, or a pharmaceutically acceptable salt thereof, wherein:

$R^1$ is selected from hydrogen, $OR^6$, $NO_2$, CN, $NR^6R^7$, $CO_2R^6$, $C(=O)NR^6R^7$, $SO_3R^6$, $SO_2NR^6R^8$, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted arylalkyl, an optionally substituted aryl, and an optionally substituted heteroaryl;

$R^2$ and $R^3$ are independently selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, an optionally substituted heteroaryl, an optionally substituted arylalkyl, an optionally substituted arylalkenyl, an optionally substituted arylalkynyl, and an optionally substituted heteroarylalkyl;

$R^5$ is selected from hydrogen, halogen, $NO_2$, CN, $CF_3$, $OR^6$, $CO_2R^6$, $C(=O)NR^6R^7$, $SO_3R^6$, and $SO_2NR^6R^8$, an optionally substituted aryl, an optionally substituted $C_1$-$C_6$ alkyl, and an optionally substituted $C_1$-$C_6$ heteroalkyl;

$R^6$ is selected from hydrogen, an optionally substituted $C_1$-$C_6$ alkyl, a $C_1$-$C_6$ heteroalkyl, an optionally substituted aryl, and an optionally substituted heteroaryl;

$R^7$ is selected from hydrogen, $C(=O)R^8$, $C(=O)NHR^8$, an optionally substituted $C_1$-$C_6$ alkyl, and an optionally substituted $C_1$-$C_6$ heteroalkyl; or $-NR^6R^7$ is an optionally substituted non-aromatic heterocycle linked through a ring nitrogen;

$R^8$ is selected from hydrogen, an optionally substituted $C_1$-$C_6$ alkyl, and an optionally substituted $C_1$-$C_6$ heteroalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

Q is selected from the group consisting of $NR^6$, an optionally substituted $C_1$-$C_6$ alkyl, an optionally substituted $C_3$-$C_8$ cycloalkyl, an optionally substituted $C_1$-$C_6$ heteroalkyl, and an optionally substituted non-aromatic heterocycle;

$L^1$ is selected from NH and $CHR^2$;

W is selected from O (oxygen) and NH;

X is N (nitrogen) or $CR^2$;

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl;

Z is O (oxygen) or S (sulfur);

n is 1, 2 or 3; and

Some embodiments include a cytotoxic GCFR modulator of Formula (I), (II), (III), or (IV) as defined above, with the proviso that if $R^2$ is methyl, $R^4$ is phenyl, $L^1$ is NH, and Q is N-Ph-$R^1$ in Formula I and III, $R^1$ of Formula I and III is not selected from the group of halogen, alkyl, substituted alkyl, carboxylic acid, and carboxylic esters.

In some methods, the cytotoxic GCFR modulator has the structure of Formula (Ia):

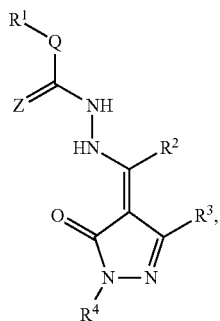

a tautomer thereof, or a pharmaceutically acceptable salt thereof, wherein:

$R^1$ is selected from hydrogen, an optionally substituted $C_1$-$C_6$ alkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted aryl, and an optionally substituted heteroaryl;

$R^2$ and $R^3$ are independently selected from hydrogen, an optionally substituted $C_1$-$C_6$ alkyl, an optionally substituted $C_3$-$C_6$ cycloalkyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_3$-$C_6$ cycloalkyl, an optionally substituted $C_3$-$C_6$ cycloalkenyl, an optionally substituted $C_1$-$C_6$ heterocycle, an optionally substituted aryl, and an optionally substituted heteroaryl;

Q is selected from an optionally substituted $C_1$-$C_6$ alkyl, an optionally substituted $C_3$-$C_8$ cycloalkyl, and an optionally substituted non-aromatic heterocycle; and Z is O (oxygen) or S (sulfur).

In some methods, the cytotoxic GCFR modulator has the structure of Formula (Ia) and $R^1$ is selected from hydrogen, and an optionally substituted $C_1$-$C_6$ alkyl; $R^2$ and $R^3$ are independently selected from hydrogen, and an optionally substituted $C_1$-$C_6$ alkyl; $R^4$ is selected from hydrogen, an optionally substituted $C_1$-$C_6$ alkyl, an optionally substituted aryl, and an optionally substituted heteroaryl; Q is selected from an optionally substituted $C_1$-$C_6$ alkyl, and an optionally substituted $C_3$-$C_8$ cycloalkyl; and Z is O (oxygen).

In some methods, the cytotoxic GCFR modulator has the structure of Formula (Ia) and $R^1$ is selected from hydrogen, and an optionally substituted $C_1$-$C_3$ alkyl; $R^2$ and $R^3$ are independently selected from hydrogen, and an optionally substituted $C_1$-$C_3$ alkyl; $R^4$ is selected from optionally substituted $C_1$-$C_6$ alkyl, and an optionally substituted aryl; and Q is selected from an optionally substituted $C_1$-$C_3$ alkyl, and an optionally substituted $C_3$-$C_3$ cycloalkyl and the remaining variables are as previously defined.

In some methods, the cytotoxic GCFR modulator has the structure of Formula (Ia) and $R^1$ is hydrogen; $R^2$ and $R^3$ are independently an optionally substituted $C_1$-$C_3$ alkyl; $R^4$ is an optionally substituted phenyl; and Q is an optionally substituted $C_1$-$C_3$ alkyl and the remaining variables are as previously defined.

In some methods, the cytotoxic GCFR modulator has the structure of Formula (IIa) or (IIb):

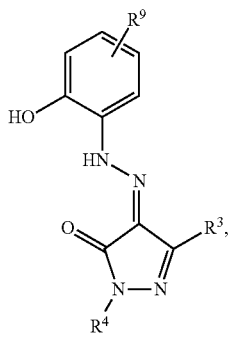

(IIa)

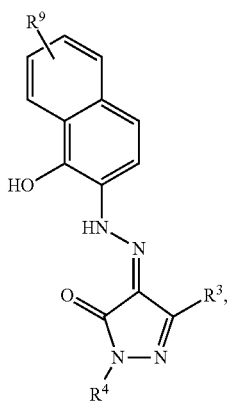

(IIb)

a tautomer thereof, or a pharmaceutically acceptable salt thereof, wherein: $R^3$ is selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl; $R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

In some methods, the cytotoxic GCFR modulator has the structure of Formula (IIa) or (IIb) and $R^3$ is selected from hydrogen, and an optionally substituted $C_1$-$C_3$ alkyl; $R^4$ is selected from an optionally substituted $C_1$-$C_6$ alkyl, an optionally substituted $C_3$-$C_8$ cycloalkyl, and an optionally substituted aryl; and $R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl and all other variables are as previously defined.

In some methods, the cytotoxic GCFR modulator has the structure of Formula (IIa) or (IIb) and $R^3$ is an optionally substituted $C_1$-$C_3$ alkyl; $R^4$ is selected from an optionally substituted $C_1$-$C_4$ alkyl, and an optionally substituted aryl; and $R^9$ is selected from an optionally substituted $C_1$-$C_3$ alkyl, an optionally substituted arylalkyl, an optionally substituted arylalkenyl, and an optionally substituted arylalkynyl and all other variables are as previously defined.

In some methods, the cytotoxic GCFR modulator has the structure of Formula (IIIa):

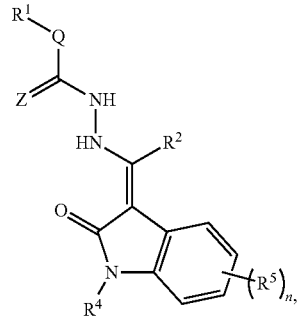

(IIIa)

a tautomer thereof, or a pharmaceutically acceptable salt thereof, wherein: $R^1$ is selected from hydrogen, $OR^6$, $NR^6R^7$, $CO_2R^6$, $C(=O)NR^6R^7$, an optionally substituted $C_2$-$C_6$ heterocyclyl, an optionally substituted arylalkyl, an optionally substituted aryl, and an optionally substituted heteroaryl; $R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl; $R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl; $R^5$ is selected from hydrogen, halogen, CN, $CF_3$, $OR^6$, an optionally substituted aryl, and an optionally substituted $C_1$-$C_6$ alkyl; $R^6$ is selected from hydrogen, an optionally substituted $C_1$-$C_6$ alkyl, an optionally substituted aryl, and an optionally substituted heteroaryl; $R^7$ is selected from hydrogen, C(=O)$R^8$, C(=O)NH$R^8$, and an optionally substituted $C_1$-$C_6$ alkyl; or —N$R^6R^7$ is an optionally substituted non-aromatic heterocycle linked through a ring nitrogen; $R^8$ is selected from hydrogen, and an optionally substituted $C_1$-$C_6$ alkyl; Q is selected from N$R^6$, an optionally substituted $C_1$-$C_6$ alkyl, an optionally substituted $C_3$-$C_8$ cycloalkyl, and an optionally substituted non-aromatic heterocyclyl; Z is O (oxygen) or S (sulfur); and n is 1, or 2.

In some methods, the cytotoxic GCFR modulator has the structure of Formula (IIIa) and $R^1$ is selected from hydrogen, O$R^6$, N$R^6R^7$, CO$_2R^6$, C(=O)N$R^6R^7$, an optionally substituted $C_2$-$C_6$ heterocyclyl, an optionally substituted arylalkyl, an optionally substituted aryl, and an optionally substituted heteroaryl; $R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl; $R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl; $R^5$ is selected from hydrogen, halogen, CN, CF$_3$, O$R^6$, an optionally substituted aryl, and an optionally substituted $C_1$-$C_6$ alkyl; $R^6$ is selected from hydrogen, and an optionally substituted $C_1$-$C_6$ alkyl; $R^7$ is selected from hydrogen, C(=O)$R^8$, C(=O)NH$R^8$, and an optionally substituted $C_1$-$C_6$ alkyl; $R^8$ is selected from hydrogen, and an optionally substituted $C_1$-$C_6$ alkyl; Q is selected from N$R^6$, an optionally substituted $C_1$-$C_4$ alkyl, an optionally substituted $C_3$-$C_6$ cycloalkyl, and an optionally substituted non-aromatic heterocyclyl; Z is O (oxygen); and n is 1 and all other variables are as previously defined.

In some methods, the cytotoxic GCFR modulator has the structure of Formula (IIIa) and $R^1$ is selected from hydrogen, O$R^6$, N$R^6R^7$, C(=O)N$R^6R^7$, an optionally substituted arylalkyl, and an optionally substituted heteroaryl; $R^2$ is selected from hydrogen, an optionally substituted $C_1$-$C_6$ alkyl, an optionally substituted aryl, and an optionally substituted heteroaryl; $R^4$ is an optionally substituted aryl; $R^5$ is selected from hydrogen, chloro, CN, CF$_3$, O$R^6$, an optionally substituted aryl, and an optionally substituted $C_1$-$C_6$ alkyl; $R^6$ is selected from hydrogen, and an optionally substituted $C_1$-$C_3$ alkyl; $R^7$ is selected from hydrogen, C(=O)$R^8$, C(=O)NH$R^8$, and an optionally substituted $C_1$-$C_3$ alkyl; $R^8$ is selected from hydrogen, and an optionally substituted $C_1$-$C_3$ alkyl; and Q is selected from optionally substituted $C_1$-$C_3$ alkyl, an optionally substituted $C_3$-$C_6$ cycloalkyl, and an optionally substituted non-aromatic heterocyclyl and all other variables are as previously defined.

In some methods, the cytotoxic GCFR modulator has the structure of Formula (IIIa) and $R^1$ is C(=O)N$R^6R^7$. In some embodiments, $R^2$ is an optionally substituted aryl. In other embodiments, $R^2$ is aryl. In some embodiments, $R^4$ is an optionally substituted aryl. In some embodiments, $R^4$ is an aryl optionally substituted with $C_1$-$C_3$alkyl, or $C_1$-$C_3$alkoxy. In other embodiments, $R^4$ is 3,5-di($C_1$-$C_3$alkyl)phenyl, 3,5-di($C_1$-$C_3$alkoxy)phenyl, 3-($C_1$-$C_3$alkyl)phenyl, 4-($C_1$-$C_3$alkyl)phenyl, or 3-($C_1$-$C_3$alkoxy)phenyl. In some embodiments, $R^4$ is 3,5-dimethylphenyl, 3,5-dimethoxyphenyl, 3-methylphenyl, 4-methylphenyl, or 3-methoxyphenyl. In other embodiments, $R^5$ is CF$_3$. In some embodiments, $R^6$ is hydrogen. In other embodiments, $R^7$ is hydrogen. In some embodiments, Q is optionally substituted $C_1$-$C_3$ alkyl. In other embodiments, Z is oxygen.

In some methods, the cytotoxic GCFR modulator has the structure of Formula (IVa) or (IVb):

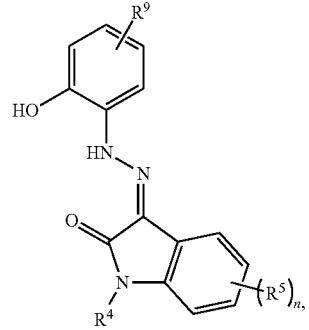

(IVa)

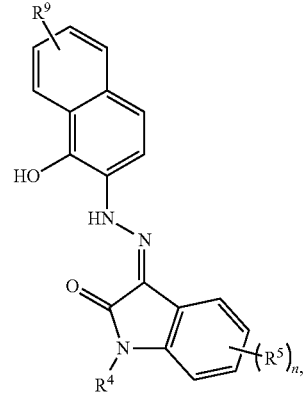

(IVb)

a tautomer thereof, or a pharmaceutically acceptable salt thereof, wherein: $R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl; $R^5$ is selected from halogen, CN, CF$_3$, O$R^6$, an optionally substituted aryl, and an optionally substituted $C_1$-$C_6$ alkyl; $R^6$ is selected from hydrogen, an optionally substituted $C_1$-$C_6$ alkyl, an optionally substituted aryl, and an optionally substituted heteroaryl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

In some methods, the cytotoxic GCFR modulator has the structure of Formula (IVa) or (IVb) and $R^4$ is selected from an optionally substituted $C_1$-$C_6$ alkyl, an optionally substituted $C_3$-$C_8$ cycloalkyl, and an optionally substituted aryl; $R^5$ is selected from chloro, CN, CF$_3$, O$R^6$, an optionally substituted aryl, and an optionally substituted $C_1$-$C_6$ alkyl; $R^6$ is selected from hydrogen, and an optionally substituted $C_1$-$C_3$ alkyl; $R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl, and n is 1, or 2.

In some methods, the cytotoxic GCFR modulator has the structure of Formula (IVa) or (IVb) and $R^4$ is selected from an optionally substituted $C_1$-$C_4$ alkyl, and an optionally substituted aryl; $R^5$ is selected from chloro, CN, CF$_3$, and an optionally substituted $C_1$-$C_3$ alkyl; $R^9$ is selected from an optionally substituted $C_1$-$C_3$ alkyl, an optionally substituted arylalkyl, an optionally substituted arylalkenyl, and an optionally substituted arylalkynyl; and n is 1.

In some methods, unless otherwise specified, groups indicated as "optionally substituted" are optionally substituted with one or more group(s) individually and independently selected from the group consisting of $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, $C_3$-$C_6$ cycloalkyl, aryl, arylalkyl, alkenylO—, arylalkylO—, arylalkylNH—, alkenylO—, cycloalkylC(=O)—, arylC(=O)—, arylC(=O)NH—, arylNHC(=O)—, aryl$(CH_2)_{0-3}$O$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, —C(=O)NHNH$_2$, heteroaryl, non-aromatic heterocycle, hydroxy, alkoxy, aryloxy, mercapto, alkylthio, arylthio, cyano, halo, oxo, O-carbamyl, N-carbamyl, O-thiocarbamyl, N-thiocarbamyl, C-amido, N-amido, S-sulfonamido, N-sulfonamido, C-carboxy, O-carboxy, nitro, and amino.

In some embodiments, the cytotoxic GCFR modulator is a GCFR agonist. In other embodiments, one or more chemotherapeutic agents is a GCFR partial agonist. In some embodiments, the cytotoxic GCFR modulator is administered as a pharmaceutically acceptable salt. In other embodiments, the cytotoxic GCFR modulator is administered as a pharmaceutical composition comprising a pharmaceutically acceptable excipient.

In some embodiments, the cytotoxic GCFR modulator is selected from:

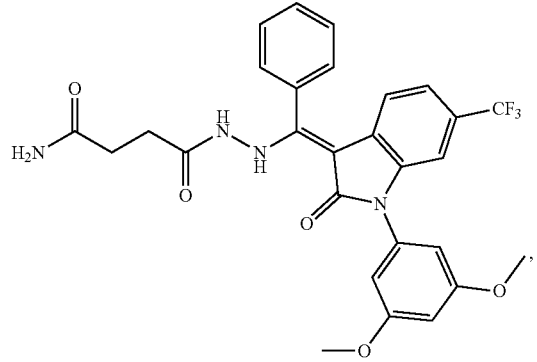

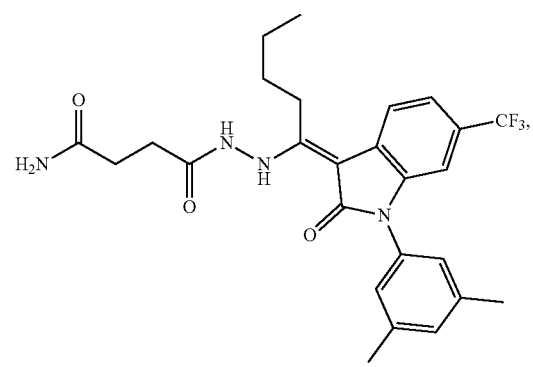

-continued

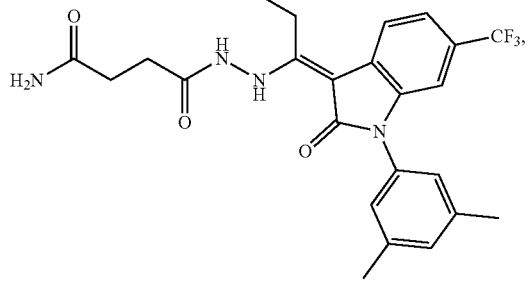

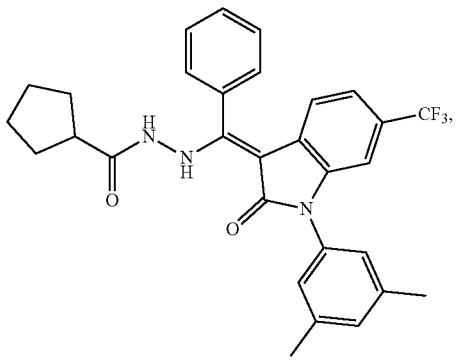

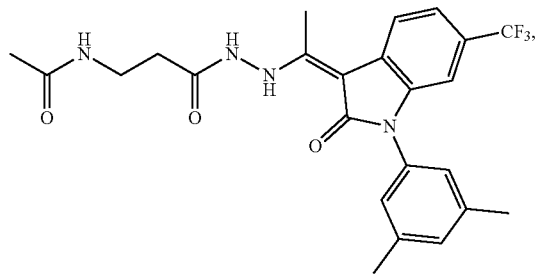

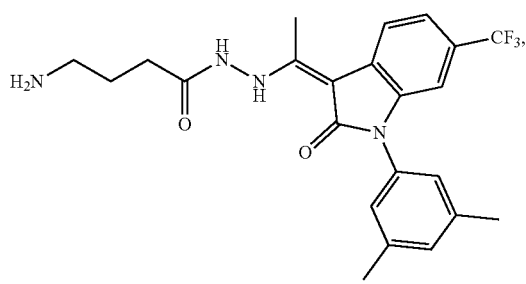

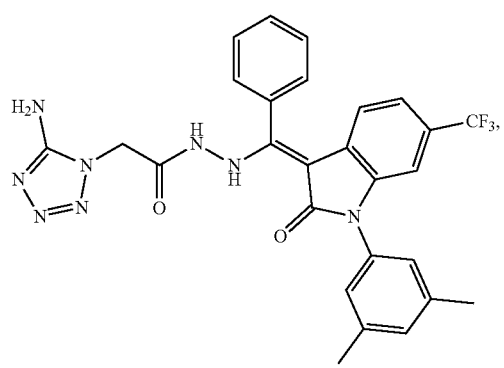

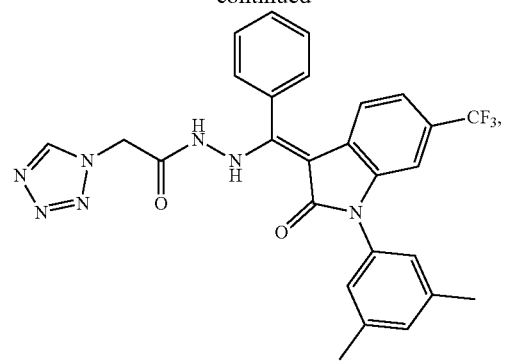
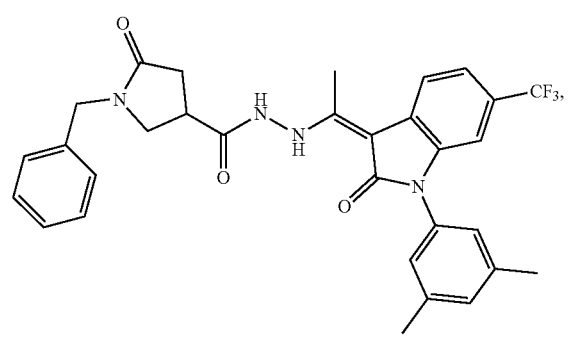
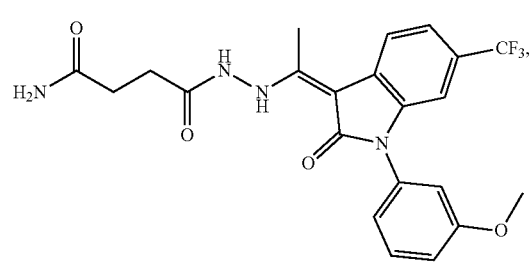
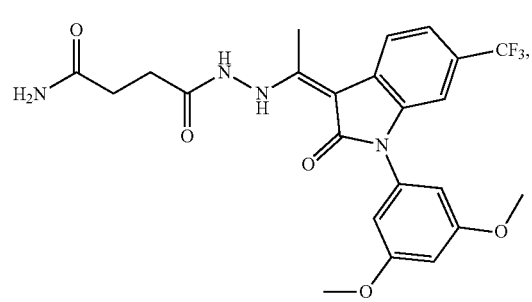
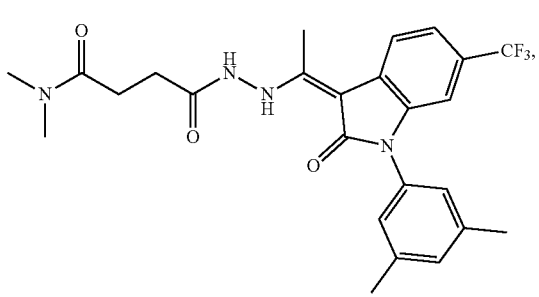
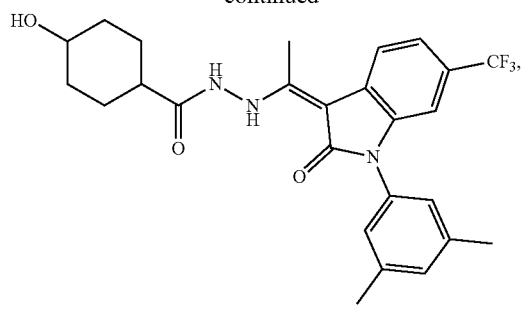
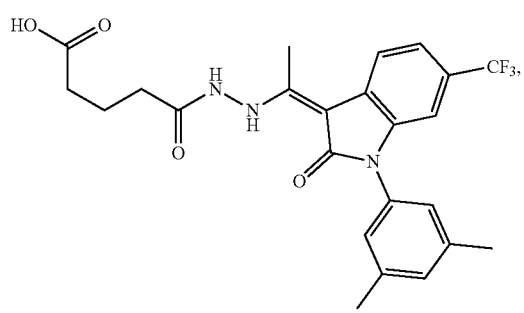
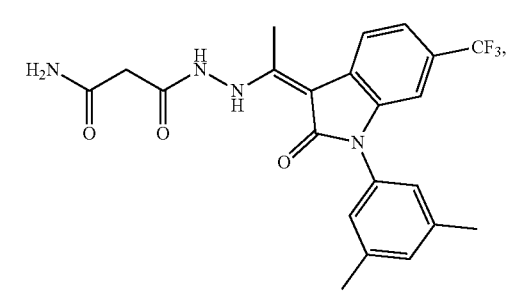
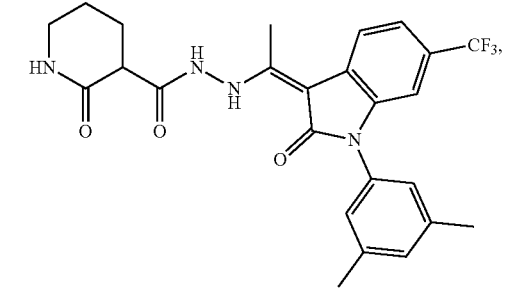
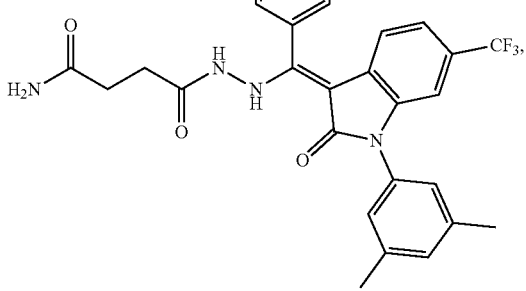

-continued
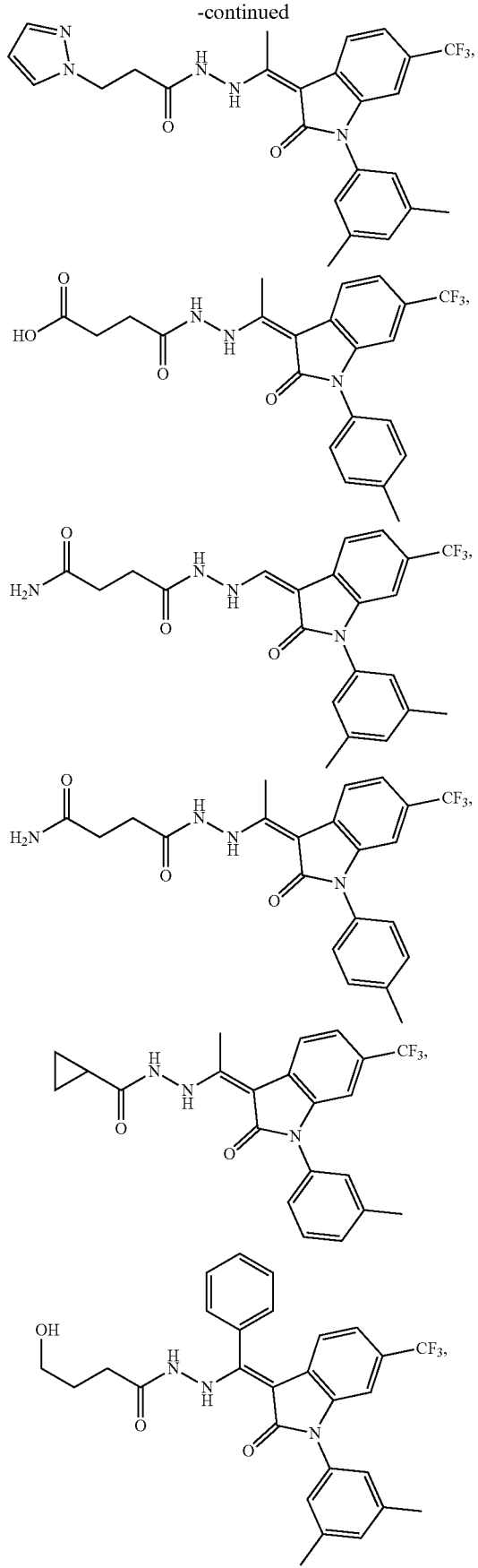
-continued
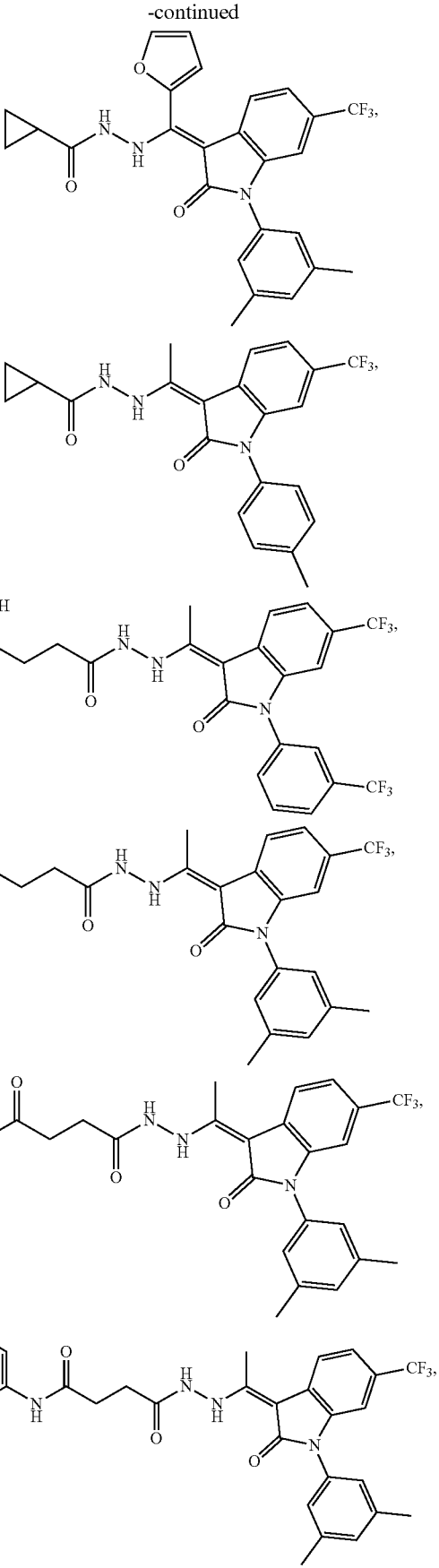

17
-continued
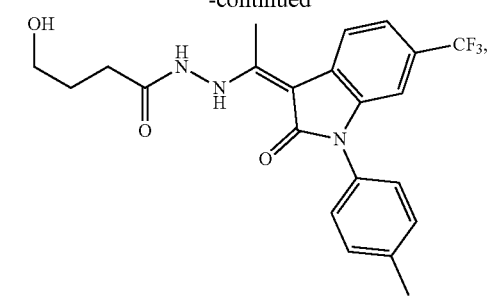
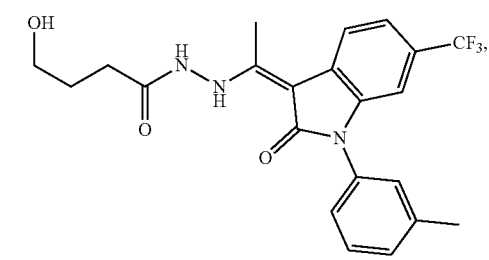
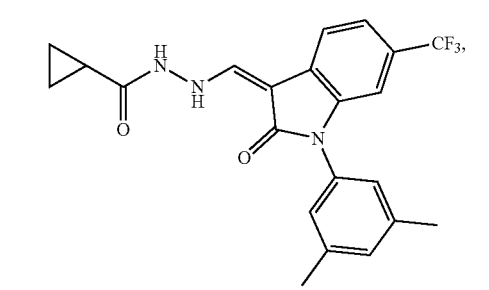
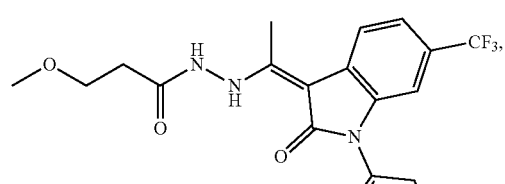
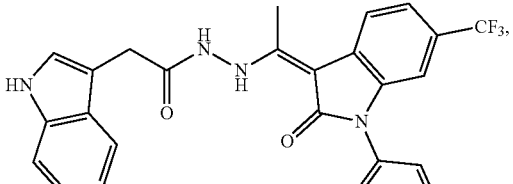
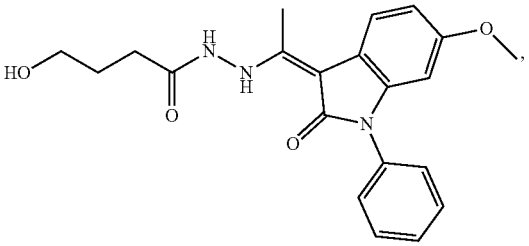
18
-continued
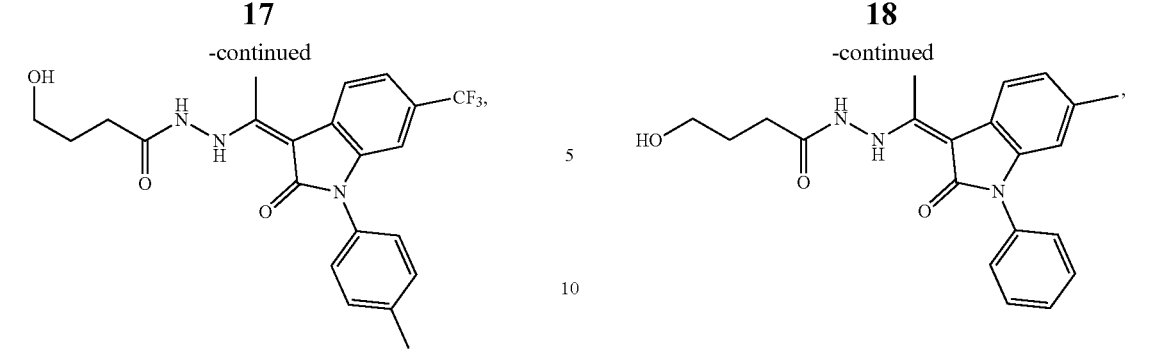
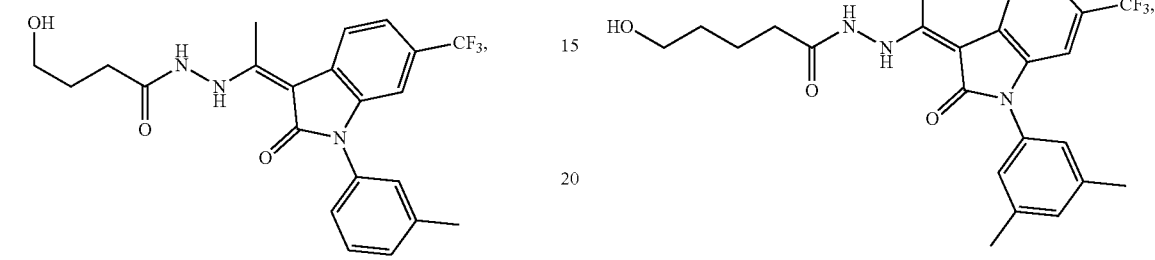
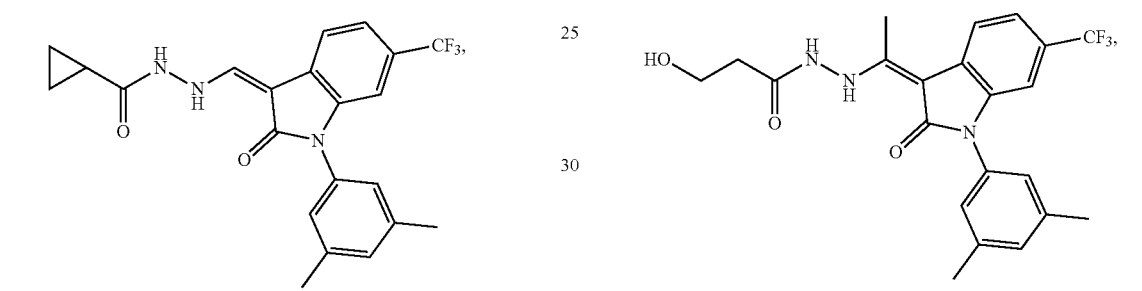
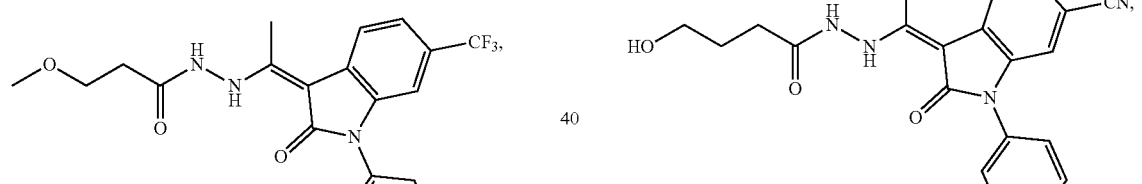
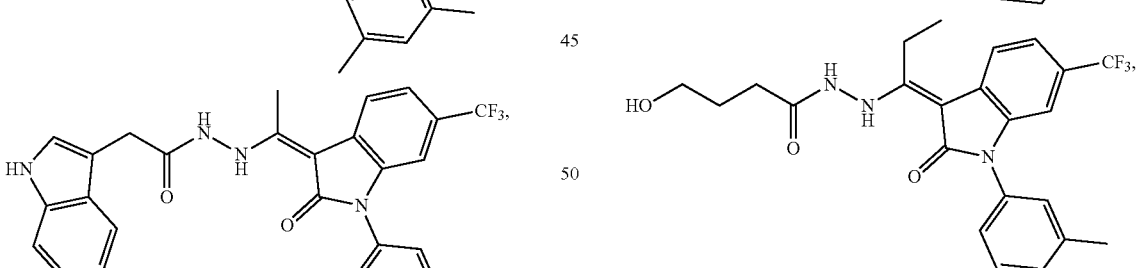
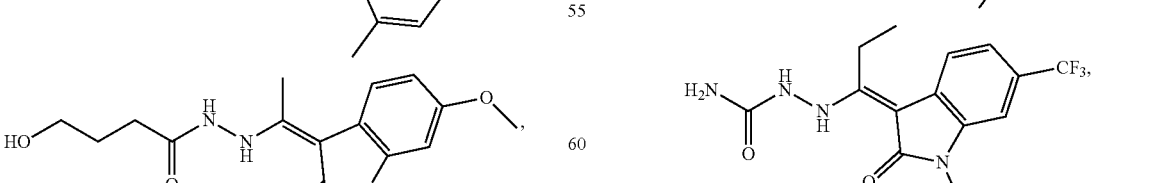

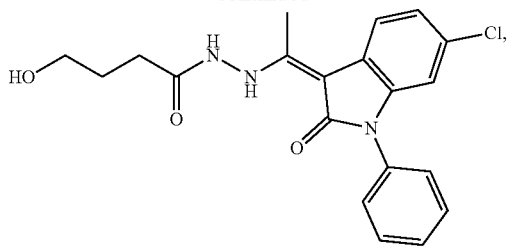
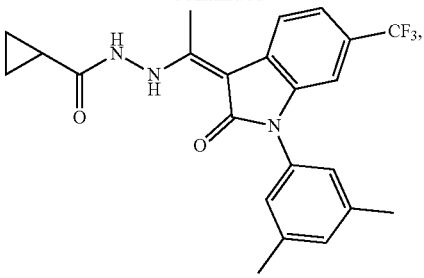
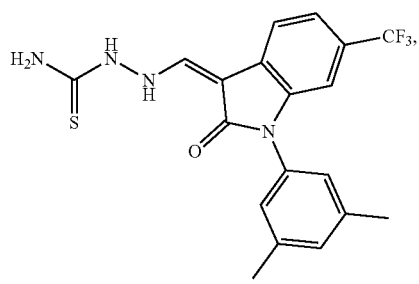
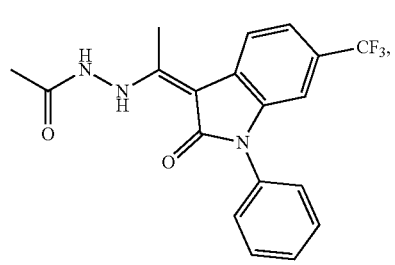
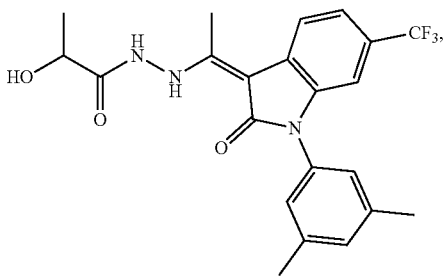
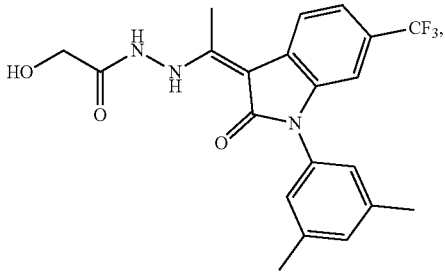
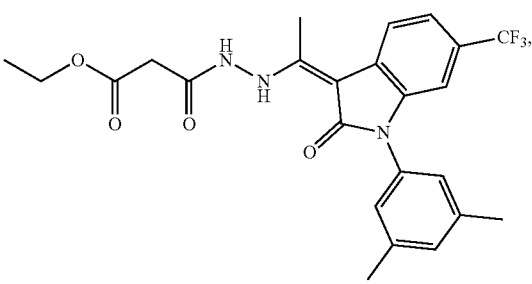

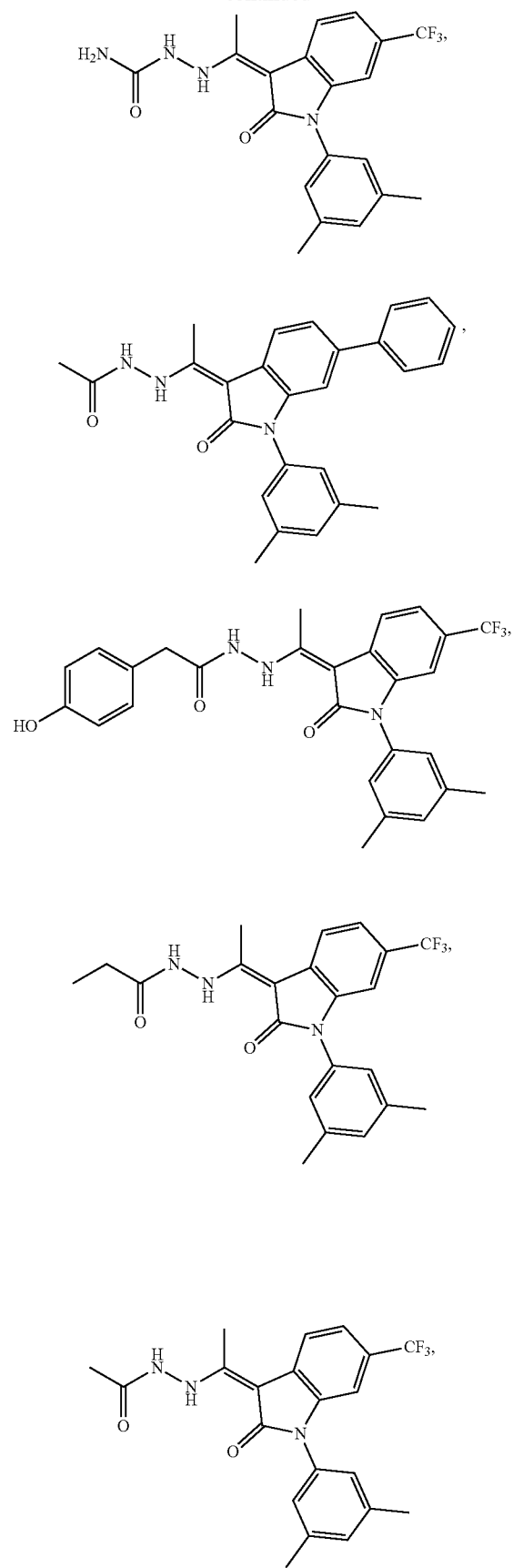

-continued
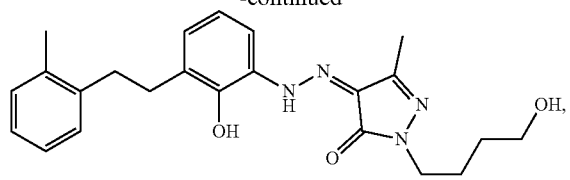
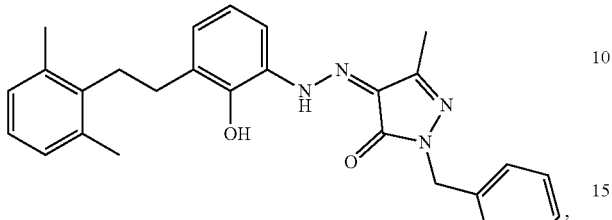
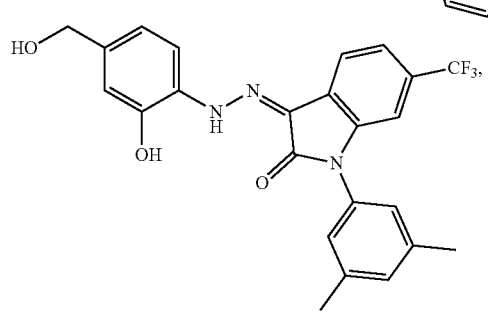
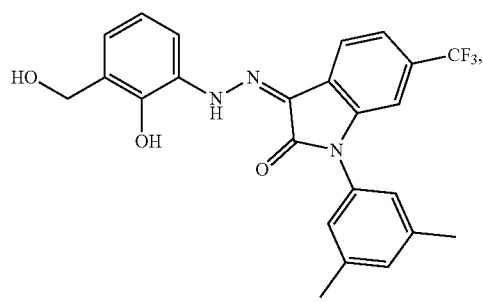
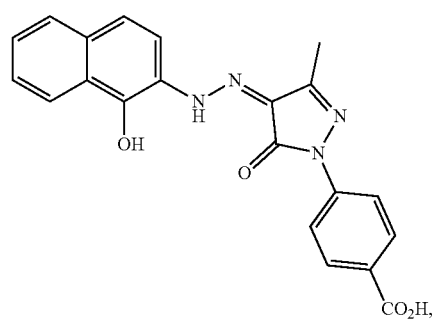
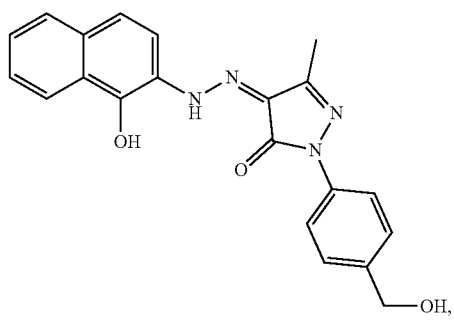
-continued
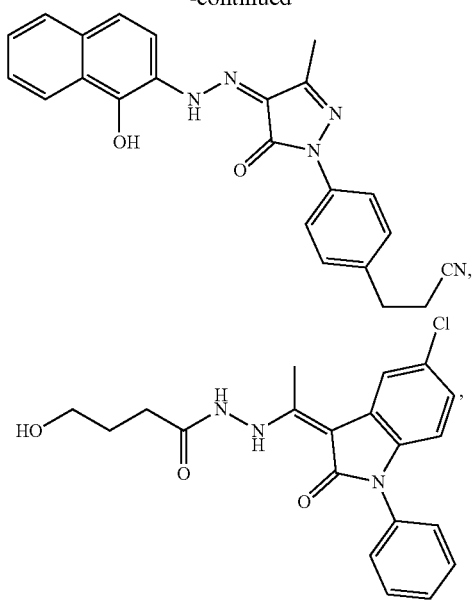
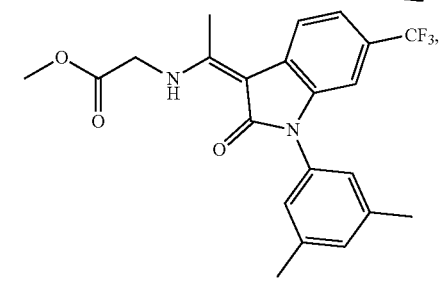
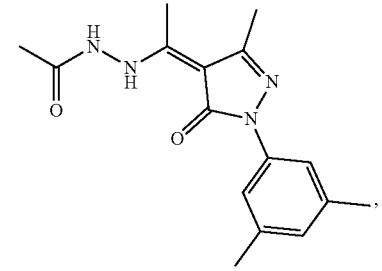
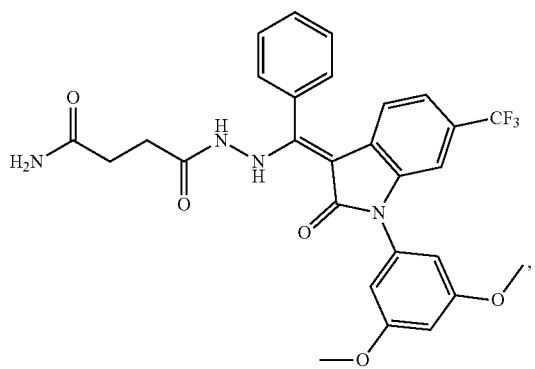
a tautomer thereof, or pharmaceutically acceptable salt thereof.
In some embodiments, the cytotoxic GCFR modulator is selected from:

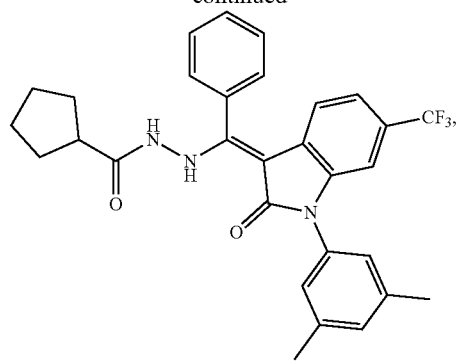
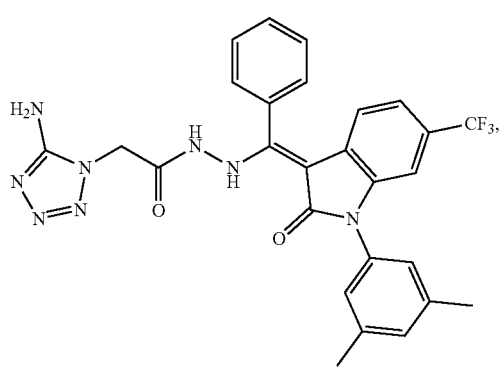
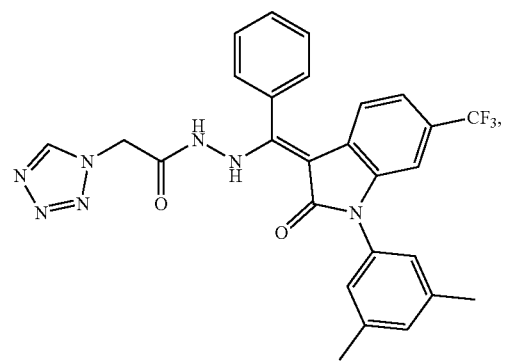
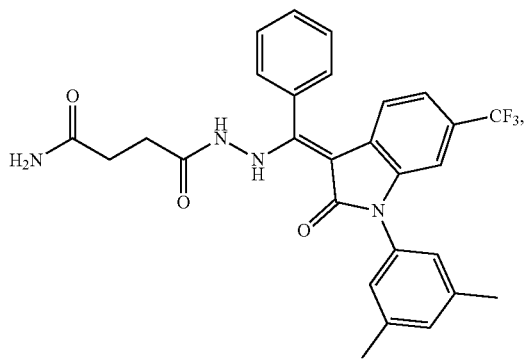
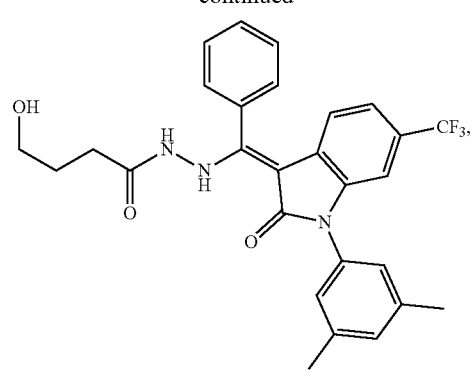
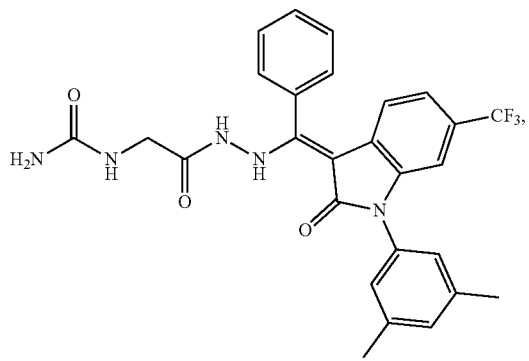
a tautomer thereof, or pharmaceutically acceptable salt thereof.
In some embodiments, the cytotoxic GCFR modulator is selected from:
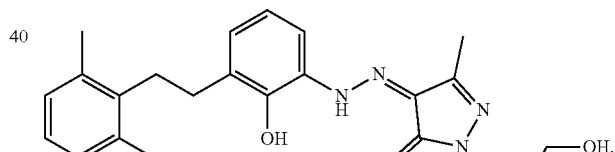
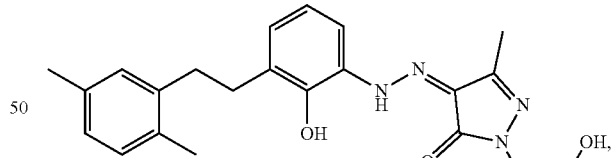
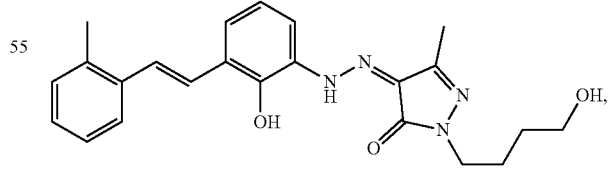
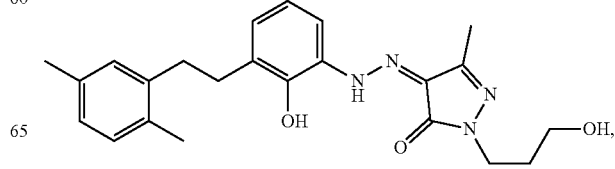

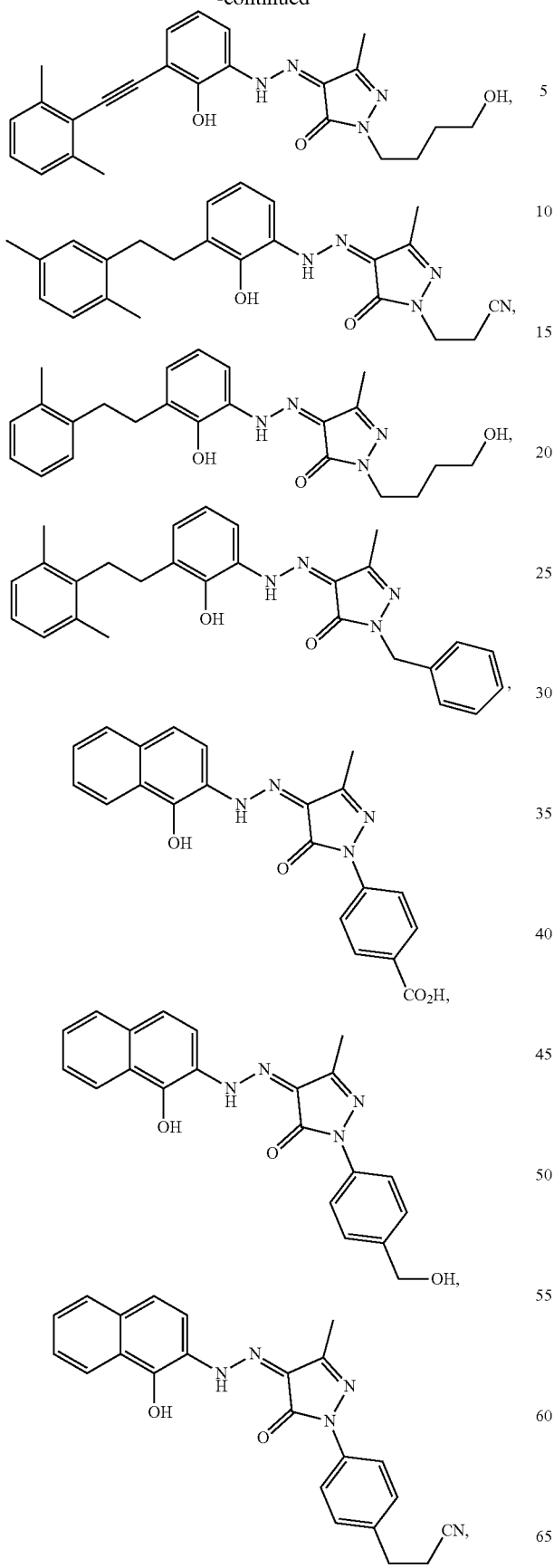
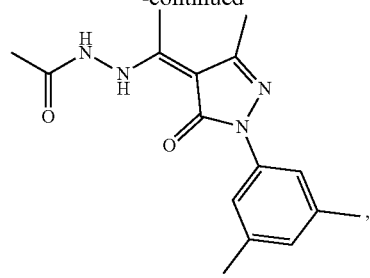
a tautomer thereof, or pharmaceutically acceptable salt thereof.
In some embodiments, the cytotoxic GCFR modulator is selected from:
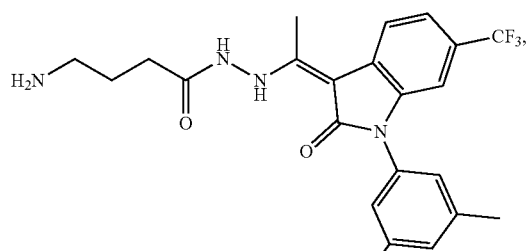
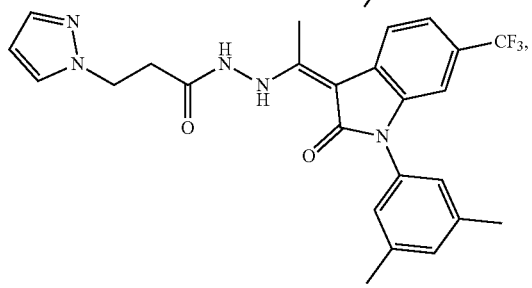
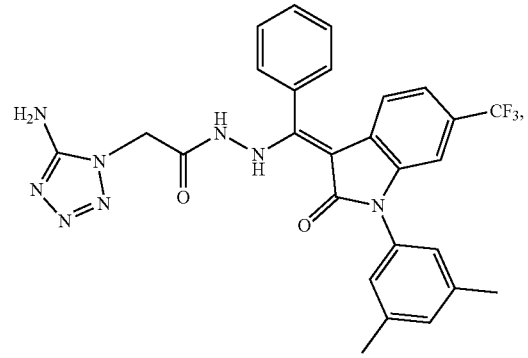
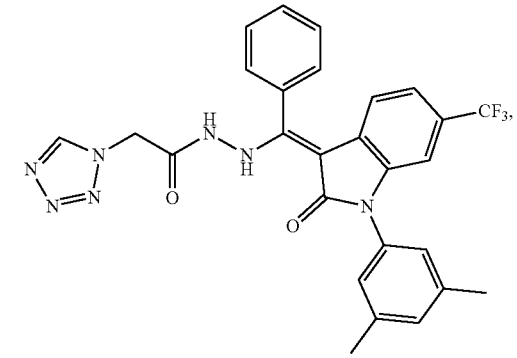

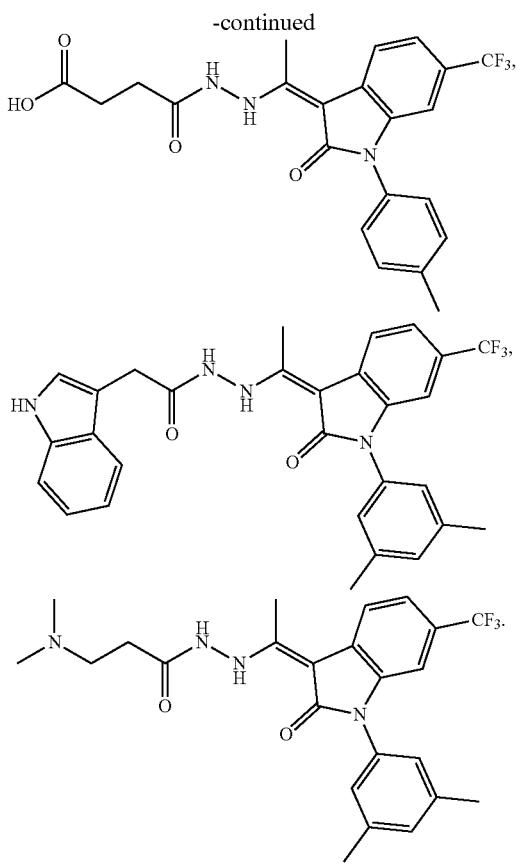

a tautomer thereof, or pharmaceutically acceptable salt thereof.

Other embodiments are directed to a method of reducing cellular proliferation, comprising: contacting a GCFR modulator with a cell selected from the group consisting of HL-60, Kasumi-1, A549, HEK293, and HEPG2. In some embodiments, the method utilizes a GCFR modulator as described above.

DETAILED DESCRIPTION

Definitions

Figure 1:
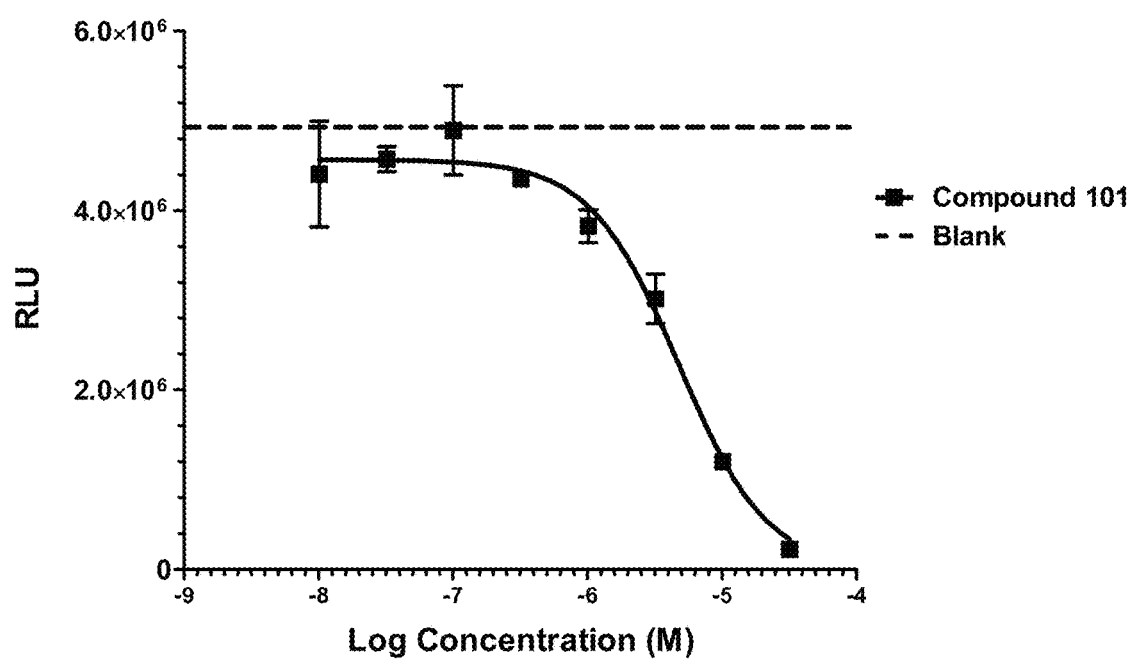
FIG. 1 is a dose-response curve illustrating the antiproliferative effect of Compound 101 on HL-60 cell growth.

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference in its entirety for any purpose.

The term "selective binding compound" refers to a compound that selectively binds to any portion of one or more target.

The term "binding-site selective hGCSFR activators" refers to a compound that selectively binds to a hGCSF receptor at or near TM domain.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a hGCSF receptor.

The term "modulator" refers to a compound that alters an activity. For example, a modulator may cause an increase or decrease in the magnitude of a certain activity compared to the magnitude of the activity in the absence of the modulator. In certain embodiments, a modulator is an inhibitor, which decreases the magnitude of one or more activities. In certain embodiments, an inhibitor completely prevents one or more biological activities. In certain embodiments, a modulator is an activator, which increases the magnitude of at least one activity. In certain embodiments the presence of a modulator results in an activity that does not occur in the absence of the modulator.

The term "selective modulator" refers to a compound that selectively modulates a target activity.

The term "selective hGCSFR modulator" refers to a compound that selectively modulates hGCSFR activity. The term selective hGCSFR modulator includes, but is not limited to "hGCSF mimic" which refers to a compound, the presence of which results in similar GCSF activity.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity, signal transduction, enzymatic activity, the proliferation and/or differentiation of progenitor cells, generation of white blood cells, and alleviation of symptoms of a disease or condition.

The term "GCSF activity" refers to a biological activity that results, either directly or indirectly from the presence of GCSF. Example GCSF activities include, but are not limited to, proliferation and or differentiation of progenitor cells to produce white blood cells; hematopoiesis; growth and/or development of glial cells; repair of nerve cells; and alleviation of granulocytopenia.

The term "receptor mediated activity" refers to any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound, the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "alkyl" refers to a branched or unbranched fully saturated acyclic aliphatic hydrocarbon group. An alkyl may be branched or straight chain. Alkyls may be substituted or unsubstituted. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "alkenyl" used herein refers to a monovalent straight or branched chain aliphatic hydrocarbon radical of from two to twenty carbon atoms containing at least one carbon-carbon double bond including, but not limited to, 1-propenyl, 2-propenyl, 2-methyl-1-propenyl, 1-butenyl, 2-butenyl, and the like. In certain embodiments, an alkenyl comprises 2 to 20 carbon atoms (whenever it appears herein, a numerical range such as "2 to 20" refers to each integer in the given range; e.g., "2 to 20 carbon atoms" means that an alkenyl group may comprise only 2 carbon atoms, 3 carbon atoms, etc., up to and including 20 carbon atoms, although the term "alkenyl" also includes instances where no numerical range of carbon atoms is designated). An alkenyl may be designated as "$C_2$-$C_6$ alkenyl" or similar designations. By way of example only, "$C_2$-$C_4$ alkenyl" indicates an alkenyl having two, three, or four carbon atoms, e.g., the alkenyl is selected from ethenyl, propenyl, and butenyl.

The term "alkynyl" used herein refers to a monovalent straight or branched chain aliphatic hydrocarbon radical of from two to twenty carbon atoms containing at least one carbon-carbon triple bond including, but not limited to, 1-propynyl, 1-butynyl, 2-butynyl, and the like. In certain embodiments, an alkynyl comprises 2 to 20 carbon atoms (whenever it appears herein, a numerical range such as "2 to 20" refers to each integer in the given range; e.g., "2 to 20 carbon atoms" means that an alkynyl group may comprise only 2 carbon atoms, 3 carbon atoms, etc., up to and including 20 carbon atoms, although the term "alkynyl" also includes instances where no numerical range of carbon atoms is designated). An alkynyl may be designated as "$C_2$-$C_6$ alkynyl" or similar designations. By way of example only, "$C_2$-$C_4$ alkynyl" indicates an alkenyl having two, three, or four carbon atoms, e.g., the alkenyl is selected from ethynyl, propynyl, and butynyl.

The term "cycloalkyl" used herein refers to saturated aliphatic ring system radical having three to twenty carbon atoms. A cycloalkyl refers to monocyclic and polycyclic saturated aliphatic ring system including, but not limited to, cyclopropyl, cyclopentyl, cyclohexyl, cycloheptyl, bicyclo[4.4.0]decanyl, bicyclo[2.2.1]heptanyl, adamantyl, norbomyl, and the like. In certain embodiments, a cycloalkyl comprises 3 to 20 carbon atoms (whenever it appears herein, a numerical range such as "3 to 20" refers to each integer in the given range; e.g., "3 to 20 carbon atoms" means that a cycloalkyl group may comprise only 3 carbon atoms, etc., up to and including 20 carbon atoms, although the term "cycloalkyl" also includes instances where no numerical range of carbon atoms is designated). A cycloalkyl may be designated as "$C_3$-$C_7$ cycloalkyl" or similar designations. By way of example only, "$C_3$-$C_6$ cycloalkyl" indicates an alkenyl having two, three, four, five or six carbon atoms, e.g., the cycloalkyl is selected from cyclopropyl, cyclobutyl, cyclopentyl, and cyclohexyl.

The term "cycloalkenyl" used herein refers to aliphatic ring system radical having three to twenty carbon atoms having at least one carbon-carbon double bond in the ring. A cycloalkenyl refers to monocyclic and polycyclic unsaturated aliphatic ring system including, but are not limited to, cyclopropenyl, cyclopentenyl, cyclohexenyl, cycloheptenyl, bicyclo[3.1.0]hexyl, norbomylenyl, 1,1'-bicyclopentenyl, and the like. In certain embodiments, a cycloalkenyl comprises 3 to 20 carbon atoms (whenever it appears herein, a numerical range such as "3 to 20" refers to each integer in the given range; e.g., "3 to 20 carbon atoms" means that a cycloalkenyl group may comprise only 3 carbon atoms, etc., up to and including 20 carbon atoms, although the term "cycloalkenyl" also includes instances where no numerical range of carbon atoms is designated). A cycloalkenyl may be designated as "$C_3$-$C_7$ cycloalkenyl" or similar designations. By way of example only, "$C_3$-$C_6$ cycloalkenyl" indicates an alkenyl having two, three, four, five or six carbon atoms, e.g., the cycloalkyl is selected from cyclopropenyl, cyclobutenyl, cyclopentenyl, and cyclohexenyl.

The term "heteroalkyl" refers to a group comprising an alkyl and one or more heteroatoms. Certain heteroalkyls are acylalkyls, in which the one or more heteroatoms are within an alkyl chain. Examples of heteroalkyls include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like. An alkoxy may be designated as "$C_1$-$C_6$ alkoxy" or similar designations. By way of example only, "$C_1$-$C_4$ alkoxy" indicates an alkyl having one, two, three, or four carbon atoms, e.g., the alkoxy is selected from methoxy, ethoxy, propoxy, iso-propoxy, butoxy, iso-butoxy, sec-butoxy, and tert-butoxy.

The term "olefin" refers to a C=C bond.

The term "alkylideneamino" used herein refers to a moiety of from one to twenty carbon atoms containing at least one carbon-nitrogen double bond where the moiety is connected to the main group through the nitrogen, including, but not limited to, methylideneamino, ethylideneamino, methylethylideneamino, propylideneamino, 1-methylpropylideneaminyl, 2-methylpropylideneamino, butylideneamino, 1-methylbutylideneamino, 2-methylbutylideneamino, cyclopropylideneamino, cyclobutylideneamino, cyclopentylideneamino, cyclohexylideneamino and the like.

The term "carbocycle" refers to a group comprising a covalently closed ring, wherein each of the atoms forming the ring is a carbon atom. Carbocylic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

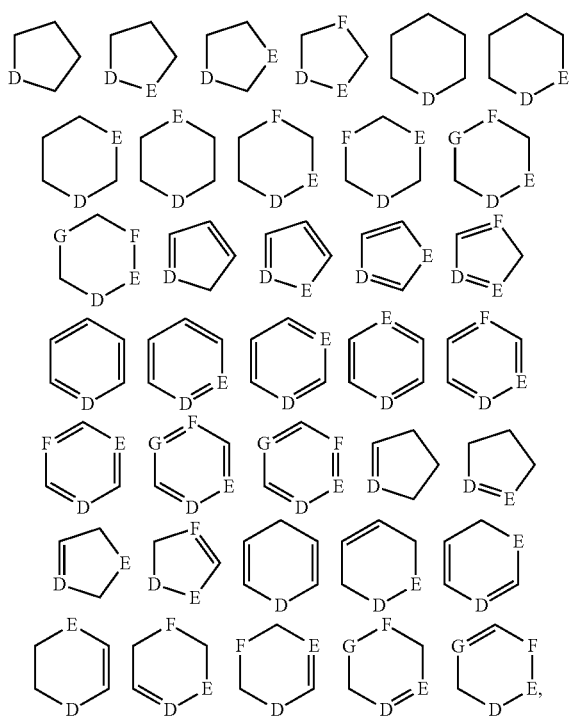

wherein D, E, F, and G independently represent a heteroatom. Each of D, E, F, and G may be the same or different from one another.

The term "heteroatom" refers to an atom other than carbon or hydrogen.

Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_3$-8 heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that does not have a delocalized π-electron system.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "arylalkenyl" refers to a group comprising an aryl group bound to an alkenyl group.

The term "arylalkynyl" refers to a group comprising an aryl group bound to an alkynyl group.

The term "heteroarylalkyl" refers to a group comprising a heteroaryl group bound to an alkyl group.

The term "heteroarylalkenyl" refers to a group comprising a heteroaryl group bound to an alkenyl group.

The term "heteroarylalkynyl" refers to a group comprising a heteroaryl group bound to an alkynyl group.

The term "carbocycloalkyl" refers to a group comprising a carbocyclic cycloalkyl ring. Carbocycloalkyl rings may be formed by three, four, five, six, seven, eight, nine, or more than nine carbon atoms. Carbocycloalkyl groups may be optionally substituted.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings may be optionally substituted. Rings may form part of a ring system.

The term "ring system" refers to a either a single ring or two or more rings, wherein, if two or more rings are present, the two or more of the rings are fused. The term "fused" refers to structures in which two or more rings share one or more bonds.

As used herein, the term "linked to form a ring" refers to instances where two atoms that are bound either to a single atom or to atoms that are themselves ultimately bound, are each bound to a linking group, such that the resulting structure forms a ring. That resulting ring comprises the two atoms that are linked to form a ring, the atom (or atoms) that previously linked those atoms, and the linker. For example, if A and E below are "linked to form a ring"

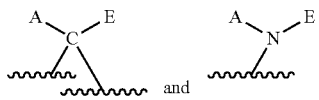

the resulting ring includes A, E, the C (carbon) or N (nitrogen) to which they are attached, and a linking group. Unless otherwise indicated, that linking group may be of any length and may be optionally substituted. Referring to the above example, resulting structures include, but are not limited to:

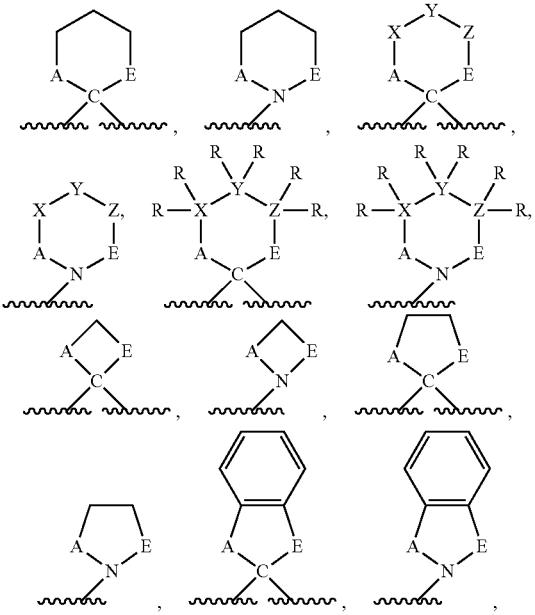

and the like.

In certain embodiments, the two substituents that together form a ring are not immediately bound to the same atom. For example, if A and E, below, are linked to form a ring:

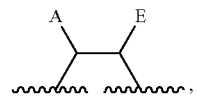

the resulting ring comprises A, E, the two atoms that already link A and E and a linking group. Examples of resulting structures include, but are not limited to:

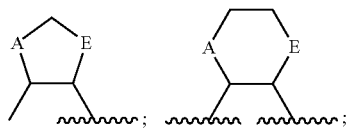

and the like.

In certain embodiments, the atoms that together form a ring are separated by three or more atoms. For example, if A and E, below, are linked to form a ring:

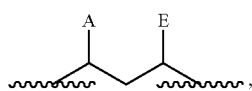

the resulting ring comprises A, E, the 3 atoms that already link A and E, and a linking group. Examples of resulting structures include, but are not limited to:

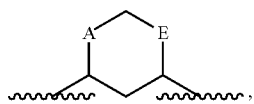

and the like.

As used herein, the term "together form a bond" refers to the instance in which two substituents to neighboring atoms are null such that the bond between the neighboring atoms becomes a double bond. For example, if A and E below "together form a bond"

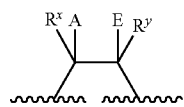

the resulting structure is:

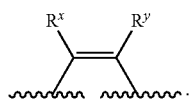

The term "null" refers to a group being absent from a structure. For example, in the structure

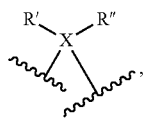

where in certain instances X is N (nitrogen), if X is N (nitrogen), one of R' or R" is null, meaning that only three groups are bound to the N (nitrogen).

The substituent "R" appearing by itself and without a number designation refers to a substituent selected from alkyl, cycloalkyl, aryl, heteroaryl (bonded through a ring carbon) and non-aromatic heterocycle (bonded through a ring carbon).

The term "O-carboxy" refers to the group consisting of formula RC(=O)O—.

The term "C-carboxy" refers to the group consisting of formula —C(=O)OR.

The term "acetyl" refers to the group consisting of formula —C(=O)CH$_3$.

The term "trihalomethanesulfonyl" refers to the group consisting of formula X$_3$CS(=O)$_2$— where X is a halogen.

The term "cyano" refers to the group consisting of formula —CN.

The term "isocyanato" refers to the group consisting of formula —NCO.

The term "thiocyanato" refers to the group consisting of formula —CNS.

The term "isothiocyanato" refers to the group consisting of formula —NCS.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "trihalomethanesulfonamido" refers to the group consisting of formula X$_3$CS(=O)$_2$NR—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "keto" and "carbonyl" used herein refers to C=O.

The term "thiocarbonyl" used herein refers to C=S.

The term "ester" refers to a chemical moiety with formula —(R)$_n$—C(=O)OR', where R and R' are independently selected from alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(=O)NHR' or —(R)$_n$—NHC(=O)R', where R is selected from alkyl, cycloalkyl, aryl, heteroaryl (bonded through a ring carbon) and heteroalicyclic (bonded through a ring carbon), where n is 0 or 1 and R' is selected from hydrogen, alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The term "amino" refers to a chemical moiety with formula —NHR'R", where R' and R" are each independently selected from hydrogen, alkyl, cycloalkyl, aryl, heteroaryl (bonded through a ring carbon) and heteroalicyclic (bonded through a ring carbon).

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) individually and independently selected from: alkyl, alkenyl, cycloalkenyl, alkynyl, heteroalkyl, haloalkyl, cycloalkyl, aryl, arylalkyl, alkenylO—, arylalkylO—, arylalkylNH—, alkenylO—, cycloalkylC(=O)—, arylC(=O)—, arylC(=O)NH—, arylNHC(=O)—, aryl (CH$_2$)$_{0-3}$O(CH$_2$)$_{0-3}$—, —COOH, HO(CH$_2$)$_{1-3}$NH—, HO(CH$_2$)$_{1-3}$O—, HO(CH$_2$)$_{1-3}$—, HO(CH$_2$)$_{1-3}$O(CH$_2$)$_{1-3}$—, —C(=O)NHNH$_2$, heteroaryl, non-aromatic heterocycle, hydroxy, alkoxy, aryloxy, mercapto, alkylthio, arylthio, cyano, halo, carbonyl, oxo, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives of amino groups. Such protective derivatives (and protecting groups that may form such protective derivatives) are known to those of skill in the art and may be found in references such as Greene and Wuts, above. When the group contains a nitrogen, or a sulfur, an oxo as a substituent also includes oxides, for example pyridine-N-oxide, thiopyran sulfoxide and thiopyran-S,S-dioxide. In embodiments in which two or more hydrogen atoms have been substituted, the substituent groups may together form a ring.

The term "isomer" includes but is not limited to stereoic isomers, geometric isomers, enantiomeric isomers, tautomeric isomers, and atromeric isomers.

Throughout the specification, groups and substituents thereof can be chosen by one skilled in the field to provide stable moieties and compounds.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to a pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" or "subject" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate receptor mediated biological activity in one tissue and fail to modulate, or modulate to a lesser degree, receptor mediated biological activity in another tissue type.

The term "monitoring" refers to observing an effect or absence of any effect. In certain embodiments, one monitors cells after contacting those cells with a compound of the present embodiments. Examples of effects that may be monitored include, but are not limited to, changes in cell phenotype, cell proliferation, receptor activity, or the interaction between a receptor and a compound known to bind to the receptor.

The term "cell phenotype" refers to physical or biological characteristics. Examples of characteristics that constitute phenotype include, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. In certain embodiments, cells are in situ in an organism. In certain embodiments, cell are grown in vitro in a vessel. The number of cells growing in a vessel can be quantified by a person skilled in the art (e.g., by counting cells in a defined area using a microscope or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Methods:

Some embodiments include methods for treating, preventing, reversing, halting, or slowing the progression of cancer, comprising administering to a subject in need thereof an effective amount of one or more chemotherapeutic agents, or a pharmaceutically acceptable salt thereof, or a pharmaceutical composition, wherein at least one of the chemotherapeutic agents is a cytotoxic granulocyte colony-stimulating factor receptor (GCFR) modulator.

Some embodiments include a method of treating a hematopoietic disorder, comprising administered a therapeutically effective cytotoxic amount of a GCFR modulator to a subject in need thereof. In some embodiments, the GCFR modulator is administered to a subject in need thereof at an interval that achieves a therapeutically effective plasma concentration of the modulator in the subject's bloodstream over a period of time.

Some embodiments include a method of treating a hematopoietic disorder, comprising administering a therapeutically effective amount of a GCFR modulator to a subject in need thereof at an interval that achieves a therapeutically effective plasma concentration of the modulator in the subject's bloodstream over a period of time.

In some embodiments, the hematopoietic disorder is a granulocytopenia. In some embodiments, the hematopoietic disorder is neutropenia.

In some embodiments, the subject is diagnosed as having cancer. In some embodiments, the subject is undergoing cancer treatment. In some embodiments, the subject is in need of both hematopoietic disorder treatment and cancer treatment.

In some embodiments, the cytotoxic GCFR modulator is a GCFR agonist or partial agonist. In some embodiments, the cytotoxic GCFR modulator is a GCFR agonist. In other embodiments, the one or more chemotherapeutic agents is a cytotoxic GCFR partial agonist. In some embodiments, the cytotoxic GCFR modulator is administered as a pharmaceutically acceptable salt. In other embodiments, the cytotoxic GCFR modulator is administered as a pharmaceutical composition comprising a pharmaceutically acceptable excipient.

In some embodiments, the cancer is a cancer of the blood, such as leukemia. In some embodiments, the leukemia is collectively or individually selected from the following group: chronic lymphocytic leukemia (CLL), chronic myeloid leukemia (CML), acute lymphocytic leukemia (ALL), acute myeloid leukemia (AML), T-cell prolymphocytic leukemia, large granular lymphocytic leukemia, adult T-cell leukemia, juvenile myelomonocytic leukemia, and hairy cell leukemia. In some embodiments, the leukemia is chronic leukemia and/or acute leukemia. In some embodiments, the leukemia is lymphocytic leukemia and/or myelogenous leukemia.

In some embodiments, the cancer is collectively or individually selected from the following: a cancer of the blood, lung, kidney, liver, breast, skin, or plasma cells, leukemia, non-small cell lung cancer, colon cancer, CNS cancer, skin cancer, melanoma, ovarian cancer, renal cancer, prostate cancer, a myeloma, multiple myeloma, chronic lymphocytic leukemia (CLL), chronic myeloid leukemia (CML), acute lymphocytic leukemia (ALL), acute myeloid leukemia (AML), T-cell prolymphocytic leukemia, large granular lymphocytic leukemia, adult T-cell leukemia, juvenile myelomonocytic leukemia, hairy cell leukemia; chronic leukemia; acute leukemia; acute myeloid leukemia; lymphocytic leukemia; and/or myelogenous leukemia.

In some embodiments, the cytotoxic GCFR modulator, or a pharmaceutically acceptable salt thereof, or a pharmaceutical composition thereof is administered in combination with one or more additional therapeutic regimens. In some embodiments, the additional therapeutic regimen is selected from the group consisting of chemotherapy, bone marrow transplantation, and radiation therapy. In some embodiments, the additional therapeutic regimen is chemotherapy. In some embodiments, the chemotherapy comprises administering an agent selected from the group consisting of alkylating agents, anthracyclines, cytoskeletal disruptors, epothilones, histone deacetylase inhibitors, topoisomerase inhibitors, kinase inhibitors, monoclonal antibodies, nucleotide analogs, peptide antibiotics, platinum-based agents, retinoids, and vinca alkaloids. In some embodiments, the chemotherapy comprises administering one or more agents selected from the group consisting of gemcitabine, cytarabine, cisplatin, methotrexate, 6-mercaptopurine, chlorambucil, cyclophosphamide, fludarabine, pentostatin, cladribine, imatinib, rituximab, interferon-alpha, doxorubicin, vincristine, prednisone, etoposide, bleomycin, or Alemtuzumab. In some embodiments, the chemotherapy comprises administering one or more agents selected from the group consisting of gemcitabine, cytarabine, and cisplatin.

In some embodiments, the cytotoxic GCFR modulator is selected by measuring a biomarker in the patient. In some embodiments, the biomarker is a cellular response to the cytotoxic GCFR agonist or partial agonist. In some embodiments, the cellular response is cytotoxicity. In other embodiments, the cellular response is gene regulation. In other embodiments, the cellular response is a change in mRNA levels. In some embodiments, the change in gene regulation or mRNA levels is up-regulation. In other embodiments, the change in gene regulation or mRNA levels is down-regulation. In some embodiments, the method further comprises selecting one or more chemotherapeutic agents by subjecting a sample from the patient to a companion diagnostic device. In some embodiments, the companion diagnostic device measures a biomarker in the patient.

In some embodiments, the cytotoxic GCFR modulator is a compound of Formula (I), (II), (III), or (IV):

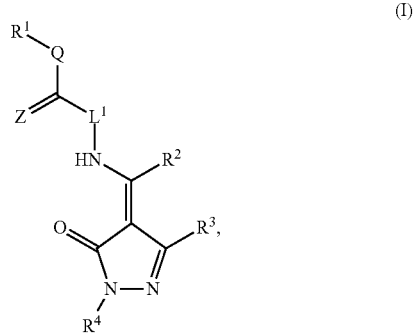

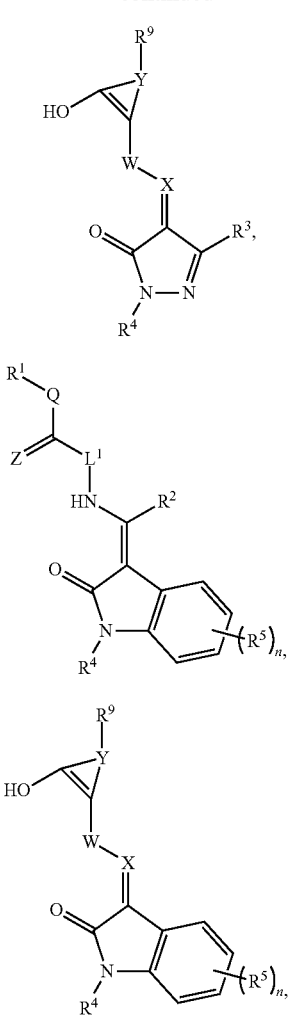

a tautomer thereof, or a pharmaceutically acceptable salt thereof, wherein:

$R^1$ is selected from hydrogen, $OR^6$, $NO_2$, CN, $NR^6R^7$, $CO_2R^6$, $C(=O)NR^6R^7$, $SO_3R^6$, $SO_2NR^6R^8$, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted arylalkyl, an optionally substituted aryl, and an optionally substituted heteroaryl;

$R^2$ and $R^3$ are independently selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, an optionally substituted heteroaryl, an optionally substituted arylalkyl, an optionally substituted arylalkenyl, an optionally substituted arylalkynyl, and an optionally substituted heteroarylalkyl;

$R^5$ is selected from hydrogen, halogen, $NO_2$, CN, $CF_3$, $OR^6$, $CO_2R^6$, $C(=O)NR^6R^7$, $SO_3R^6$, and $SO_2NR^6R^8$, an optionally substituted aryl, an optionally substituted $C_1$-$C_6$ alkyl, and an optionally substituted $C_1$-$C_6$ heteroalkyl;

$R^6$ is selected from hydrogen, an optionally substituted $C_1$-$C_6$ alkyl, a $C_1$-$C_6$ heteroalkyl, an optionally substituted aryl, and an optionally substituted heteroaryl;

$R^7$ is selected from hydrogen, $C(=O)R^8$, $C(=O)NHR^8$, an optionally substituted $C_1$-$C_6$ alkyl, and an optionally substituted $C_1$-$C_6$ heteroalkyl; or $-NR^6R^7$ is an optionally substituted non-aromatic heterocycle linked through a ring nitrogen;

$R^8$ is selected from hydrogen, an optionally substituted $C_1$-$C_6$ alkyl, and an optionally substituted $C_1$-$C_6$ heteroalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

Q is selected from the group consisting of $NR^6$, an optionally substituted $C_1$-$C_6$ alkyl, an optionally substituted $C_3$-$C_8$ cycloalkyl, an optionally substituted $C_1$-$C_6$ heteroalkyl, and an optionally substituted non-aromatic heterocycle;

$L^1$ is selected from NH and $CHR^2$;

W is selected from O (oxygen) and NH;

X is N (nitrogen) or $CR^2$;

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl;

Z is O (oxygen) or S (sulfur); and n is 1, 2 or 3.

In some embodiments, the cytotoxic GCFR modulator is a compound of Formula (I), (II), (III), or (IV) as defined above, with the proviso that if $R^2$ is methyl, $R^4$ is phenyl, $L^1$ is NH, and Q is N-Ph-$R^1$ in Formula I and III, $R^1$ of Formula I and III is not selected from the group of halogen, alkyl, substituted alkyl, carboxylic acid, and carboxylic esters.

In some embodiments, the cytotoxic GCFR modulator has the structure of Formula (Ia):

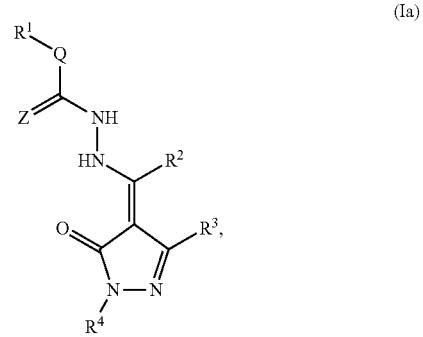

a tautomer thereof, or a pharmaceutically acceptable salt thereof, wherein:

$R^1$ is selected from hydrogen, an optionally substituted $C_1$-$C_6$ alkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted aryl, and an optionally substituted heteroaryl;

$R^2$ and $R^3$ are independently selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

Q is selected from an optionally substituted $C_1$-$C_6$ alkyl, an optionally substituted $C_3$-$C_8$ cycloalkyl, and an optionally substituted non-aromatic heterocycle; and Z is O (oxygen) or S (sulfur).

In some embodiments, the cytotoxic GCFR modulator has the structure of Formula (Ia) and $R^1$ is selected from hydrogen, and an optionally substituted $C_1$-$C_6$ alkyl; $R^2$ and $R^3$ are independently selected from hydrogen, and an optionally substituted $C_1$-$C_6$ alkyl; $R^4$ is selected from hydrogen, an optionally substituted $C_1$-$C_6$ alkyl, an optionally substituted aryl, and an optionally substituted heteroaryl; Q is selected from an optionally substituted $C_1$-$C_6$ alkyl, and an optionally substituted $C_3$-$C_8$ cycloalkyl; and Z is O (oxygen).

In some embodiments, the cytotoxic GCFR modulator has the structure of Formula (Ia) and $R^1$ is selected from hydrogen, and an optionally substituted $C_1$-$C_3$ alkyl; $R^2$ and $R^3$ are independently selected from hydrogen, and an optionally substituted $C_1$-$C_3$ alkyl; $R^4$ is selected from optionally substituted $C_1$-$C_6$ alkyl, and an optionally substituted aryl; and Q is selected from an optionally substituted $C_1$-$C_3$ alkyl, and an optionally substituted $C_3$-$C_3$ cycloalkyl and the remaining variables are as previously defined.

In some embodiments, the cytotoxic GCFR modulator has the structure of Formula (Ia) and $R^1$ is hydrogen; $R^2$ and $R^3$ are independently an optionally substituted $C_1$-$C_3$ alkyl; $R^4$ is an optionally substituted phenyl; and Q is an optionally substituted $C_1$-$C_3$ alkyl and the remaining variables are as previously defined.

In some embodiments, the cytotoxic GCFR modulator has the structure of Formula (IIa) or (IIb):

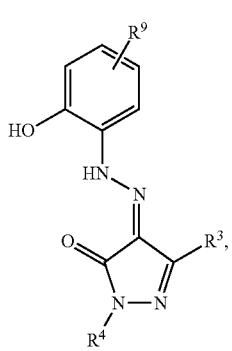

(IIa)

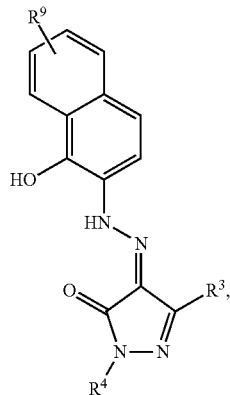

(IIb)

a tautomer thereof, or a pharmaceutically acceptable salt thereof, wherein:

$R^3$ is selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;

$R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

In some embodiments, the cytotoxic GCFR modulator has the structure of Formula (IIa) or (IIb) and $R^3$ is selected from hydrogen, and an optionally substituted $C_1$-$C_3$ alkyl; $R^4$ is selected from an optionally substituted $C_1$-$C_6$ alkyl, an optionally substituted $C_3$-$C_8$ cycloalkyl, and an optionally substituted aryl; and $R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl and all other variables are as previously defined.

In some embodiments, the cytotoxic GCFR modulator has the structure of Formula (IIa) or (IIb) and $R^3$ is an optionally substituted $C_1$-$C_3$ alkyl; $R^4$ is selected from an optionally substituted $C_1$-$C_4$ alkyl, and an optionally substituted aryl; and $R^9$ is selected from an optionally substituted $C_1$-$C_3$ alkyl, an optionally substituted arylalkyl, an optionally substituted arylalkenyl, and an optionally substituted arylalkynyl and all other variables are as previously defined.

In some embodiments, the cytotoxic GCFR modulator has the structure of Formula (IIIa):

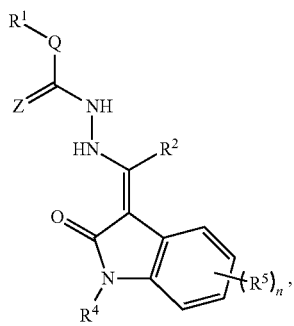

(IIIa)

a tautomer thereof, or a pharmaceutically acceptable salt thereof, wherein:

$R^1$ is selected from hydrogen, $OR^6$, $NR^6R^7$, $CO_2R^6$, $C(=O)NR^6R^7$, an optionally substituted $C_2$-$C_6$ heterocyclyl, an optionally substituted arylalkyl, an optionally substituted aryl, and an optionally substituted heteroaryl;

$R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl;

$R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl;

$R^5$ is selected from hydrogen, halogen, CN, $CF_3$, $OR^6$, an optionally substituted aryl, and an optionally substituted $C_1$-$C_6$ alkyl;

$R^6$ is selected from hydrogen, an optionally substituted $C_1$-$C_6$ alkyl, an optionally substituted aryl, and an optionally substituted heteroaryl;

$R^7$ is selected from hydrogen, $C(=O)R^8$, $C(=O)NHR^8$, and an optionally substituted $C_1$-$C_6$ alkyl; or —$NR^6R^7$ is an optionally substituted non-aromatic heterocycle linked through a ring nitrogen;

$R^8$ is selected from hydrogen, and an optionally substituted $C_1$-$C_6$ alkyl;

Q is selected from $NR^6$, an optionally substituted $C_1$-$C_6$ alkyl, an optionally substituted $C_3$-$C_8$ cycloalkyl, and an optionally substituted non-aromatic heterocyclyl;

Z is O (oxygen) or S (sulfur); and n is 1, or 2.

In some embodiments, the cytotoxic GCFR modulator has the structure of Formula (IIIa) and $R^1$ is selected from hydrogen, $OR^6$, $NR^6R^7$, $CO_2R^6$, $C(=O)NR^6R^7$, an optionally substituted $C_2$-$C_6$ heterocyclyl, an optionally substituted arylalkyl, an optionally substituted aryl, and an optionally substituted heteroaryl; $R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl; $R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl; $R^5$ is selected from hydrogen, halogen, CN, $CF_3$, $OR^6$, an optionally substituted aryl, and an optionally substituted $C_1$-$C_6$ alkyl; $R^6$ is selected from hydrogen, and an optionally substituted $C_1$-$C_6$ alkyl; $R^7$ is selected from hydrogen, $C(=O)R^8$, $C(=O)NHR^8$, and an optionally substituted $C_1$-$C_6$ alkyl; $R^8$ is selected from hydrogen, and an optionally substituted $C_1$-$C_6$ alkyl; Q is selected from $NR^6$, an optionally substituted $C_1$-$C_4$ alkyl, an optionally substituted $C_3$-$C_6$ cycloalkyl, and an optionally substituted non-aromatic heterocyclyl; Z is O (oxygen); and n is 1 and all other variables are as previously defined.

In some embodiments, the cytotoxic GCFR modulator has the structure of Formula (IIIa) and $R^1$ is selected from hydrogen, $OR^6$, $NR^6R^7$, $C(=O)NR^6R^7$, an optionally substituted arylalkyl, and an optionally substituted heteroaryl; $R^2$ is selected from hydrogen, an optionally substituted $C_1$-$C_6$ alkyl, an optionally substituted aryl, and an optionally substituted heteroaryl; $R^4$ is an optionally substituted aryl; $R^5$ is selected from hydrogen, chloro, CN, $CF_3$, $OR^6$, an optionally substituted aryl, and an optionally substituted $C_1$-$C_6$ alkyl; $R^6$ is selected from hydrogen, and an optionally substituted $C_1$-$C_3$ alkyl; $R^7$ is selected from hydrogen, $C(=O)R^8$, $C(=O)NHR^8$, and an optionally substituted $C_1$-$C_3$ alkyl; $R^8$ is selected from hydrogen, and an optionally substituted $C_1$-$C_3$ alkyl; and Q is selected from optionally substituted $C_1$-$C_3$ alkyl, an optionally substituted $C_3$-$C_6$ cycloalkyl, and an optionally substituted non-aromatic heterocyclyl and all other variables are as previously defined.

In some embodiments, the cytotoxic GCFR modulator has the structure of Formula (IIIa) and $R^1$ is $C(=O)NR^6R^7$. In some embodiments, $R^2$ is an optionally substituted aryl. In other embodiments, $R^2$ is aryl. In some embodiments, $R^4$ is an optionally substituted aryl. In some embodiments, $R^4$ is an aryl optionally substituted with $C_1$-$C_3$alkyl, or $C_1$-$C_3$alkoxy. In other embodiments, $R^4$ is 3,5-di($C_1$-$C_3$alkyl)phenyl, 3,5-di($C_1$-$C_3$alkoxy)phenyl, 3-($C_1$-$C_3$alkyl)phenyl, 4-($C_1$-$C_3$alkyl)phenyl, or 3-($C_1$-$C_3$alkoxy)phenyl. In some embodiments, $R^4$ is 3,5-dimethylphenyl, 3,5-dimethoxyphenyl, 3-methylphenyl, 4-methylphenyl, or 3-methoxyphenyl. In other embodiments, $R^5$ is $CF_3$. In some embodiments, $R^6$ is hydrogen. In other embodiments, $R^7$ is hydrogen. In some embodiments, Q is optionally substituted $C_1$-$C_3$ alkyl. In other embodiments, Z is oxygen.

In some embodiments, the cytotoxic GCFR modulator has the structure of Formula (IVa) or (IVb):

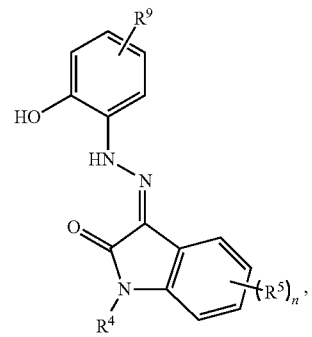

(IVa)

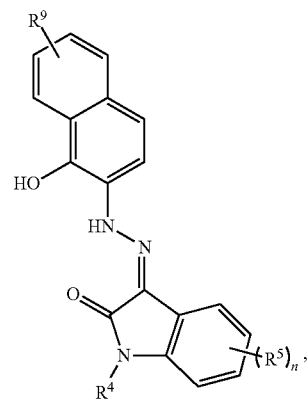

(IVb)

a tautomer thereof, or a pharmaceutically acceptable salt thereof, wherein:

$R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl;

$R^5$ is selected from halogen, CN, $CF_3$, $OR^6$, an optionally substituted aryl, and an optionally substituted $C_1$-$C_6$ alkyl;

$R^6$ is selected from hydrogen, an optionally substituted $C_1$-$C_6$ alkyl, an optionally substituted aryl, and an optionally substituted heteroaryl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl; and n is 1, 2 or 3.

In some embodiments, the cytotoxic GCFR modulator has the structure of Formula (IVa) or (IVb) and $R^4$ is selected from an optionally substituted $C_1$-$C_6$ alkyl, an optionally substituted $C_3$-$C_8$ cycloalkyl, and an optionally substituted aryl; $R^5$ is selected from chloro, CN, $CF_3$, $OR^6$, an optionally substituted aryl, and an optionally substituted $C_1$-$C_6$ alkyl; $R^6$ is selected from hydrogen, and an optionally substituted $C_1$-$C_3$ alkyl; $R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl, and n is 1, or 2.

In some embodiments, the cytotoxic GCFR modulator has the structure of Formula (IVa) or (IVb) and $R^4$ is selected from an optionally substituted $C_1$-$C_4$ alkyl, and an optionally substituted aryl; $R^5$ is selected from chloro, CN, $CF_3$, and an optionally substituted $C_1$-$C_3$ alkyl; $R^9$ is selected from an optionally substituted $C_1$-$C_3$ alkyl, an optionally substituted arylalkyl, an optionally substituted arylalkenyl, and an optionally substituted arylalkynyl; and n is 1.

In some embodiments, unless otherwise specified, groups indicated as "optionally substituted" are optionally substituted with one or more group(s) individually and independently selected from the group consisting of $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, $C_3$-$C_6$ cycloalkyl, aryl, arylalkyl, alkenylO—, arylalkylO—, arylalkylNH—, alkenylO—, cycloalkylC(=O)—, arylC(=O)—, arylC(=O)NH—, arylNHC(=O)—, aryl$(CH_2)_{0-3}$O$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, —C(=O)NHNH$_2$, heteroaryl, non-aromatic heterocycle, hydroxy, alkoxy, aryloxy, mercapto, alkylthio, arylthio, cyano, halo, oxo, O-carbamyl, N-carbamyl, O-thiocarbamyl, N-thiocarbamyl, C-amido, N-amido, S-sulfonamido, N-sulfonamido, C-carboxy, O-carboxy, nitro, and amino.

In some embodiments, the cytotoxic GCFR modulator is selected from:

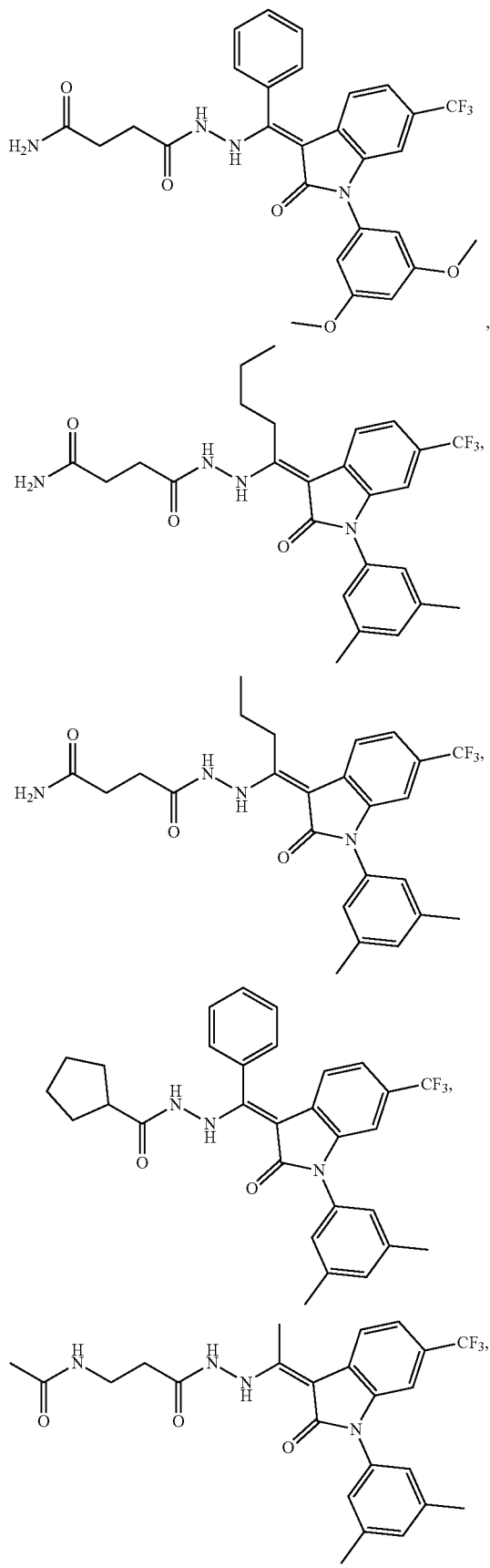

51
-continued
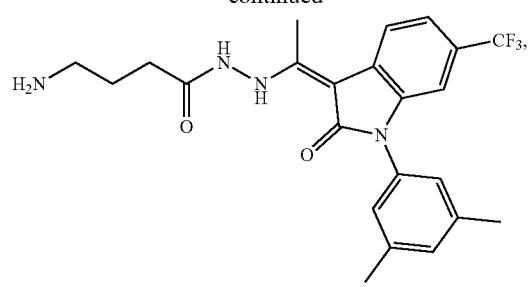
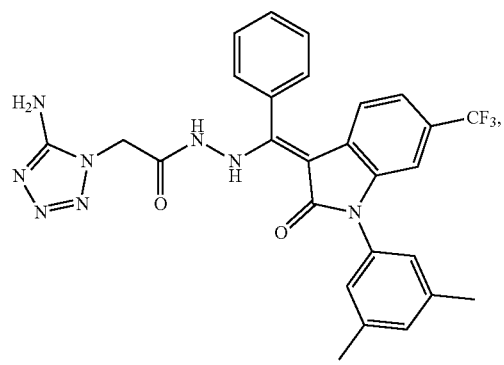
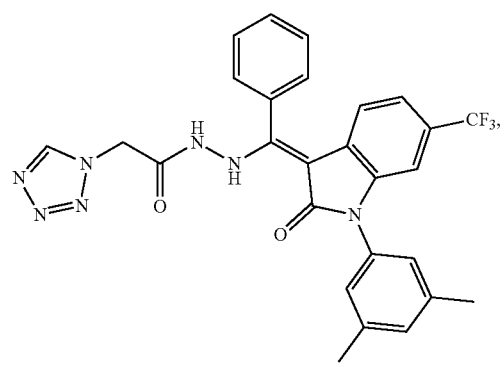
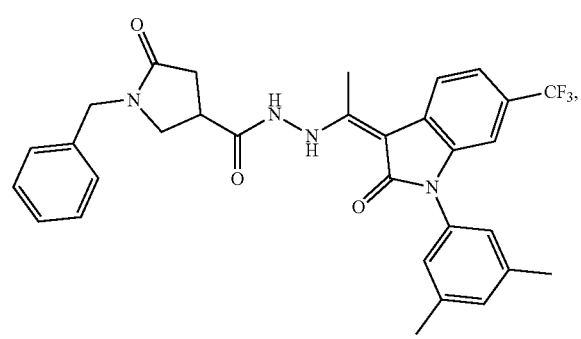
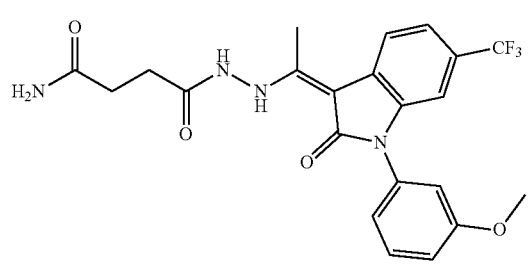
52
-continued
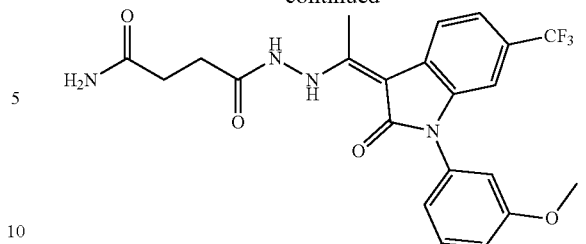
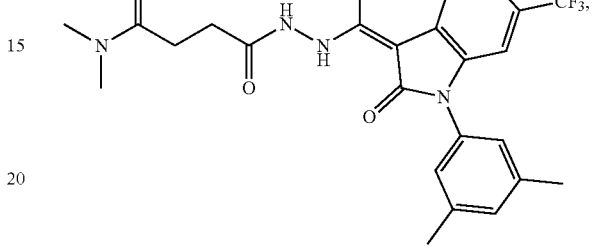
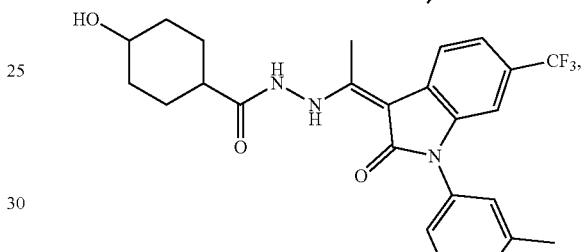
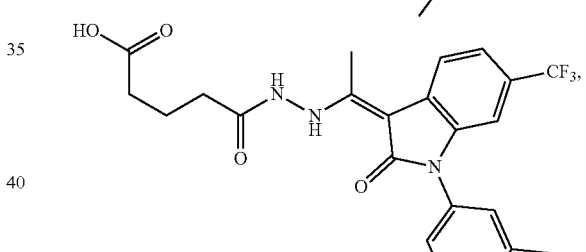
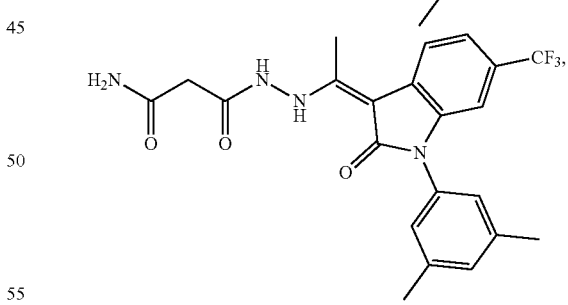
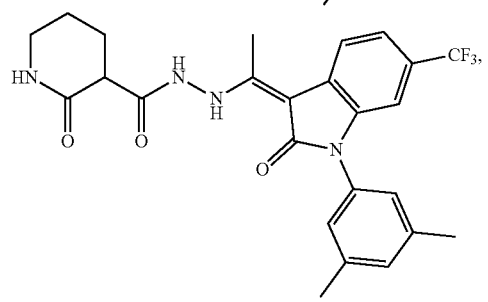

53
-continued
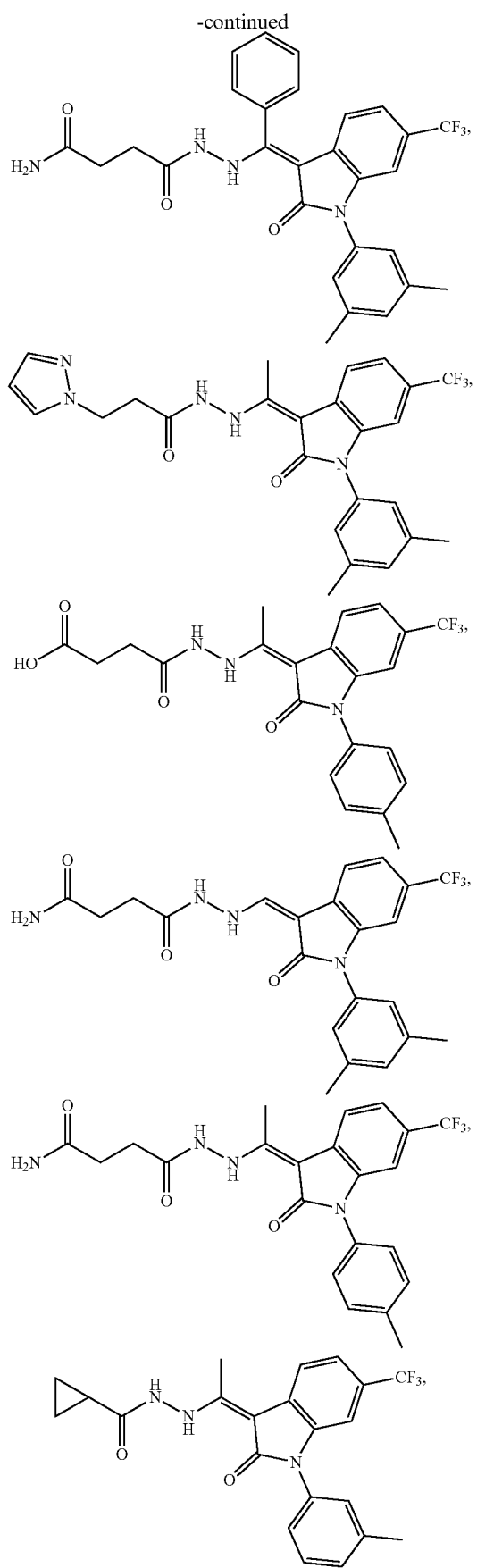
54
-continued
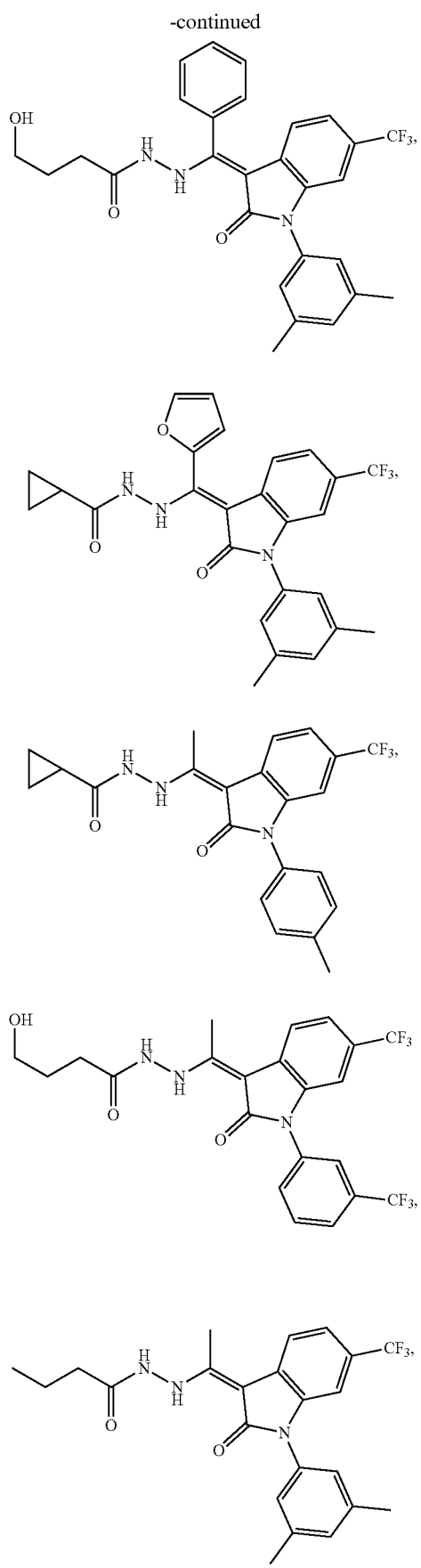

55
-continued
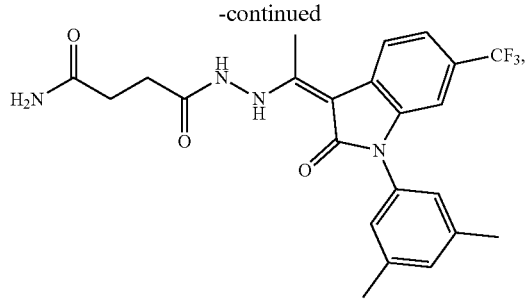
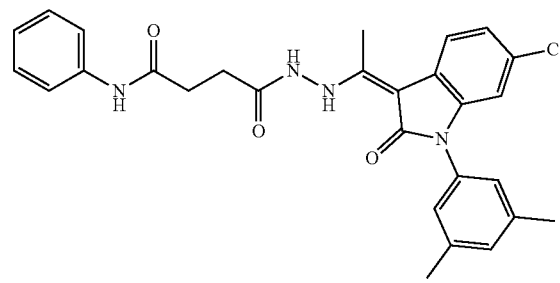
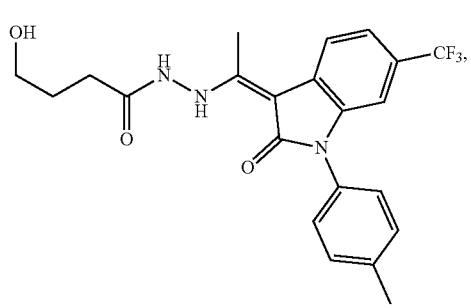
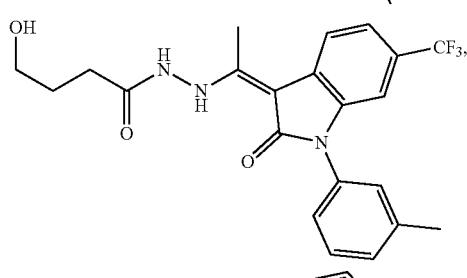
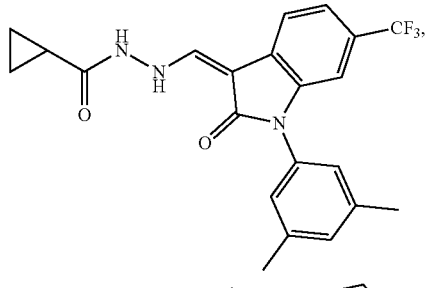
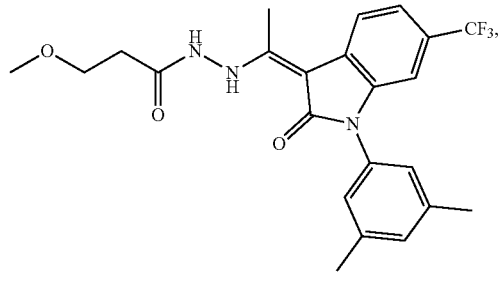
56
-continued
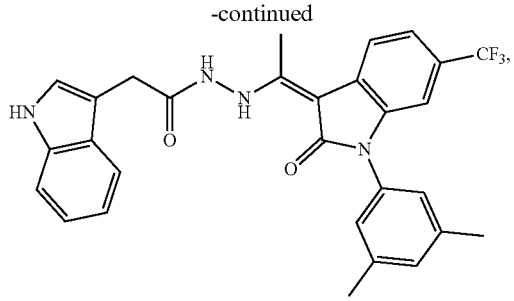
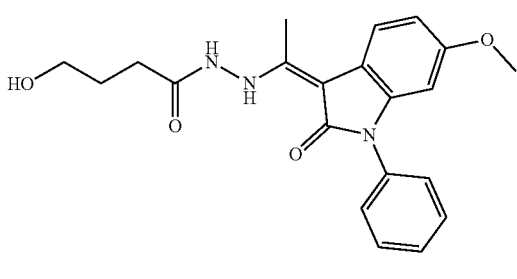
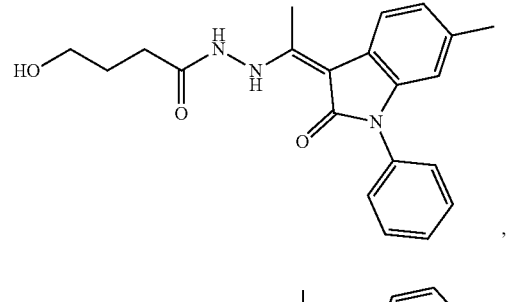
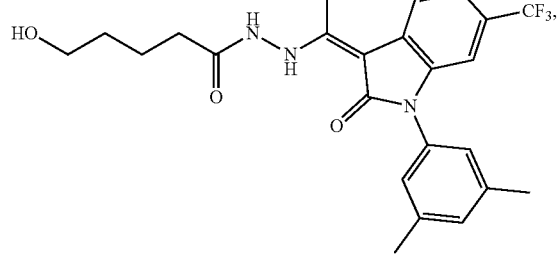
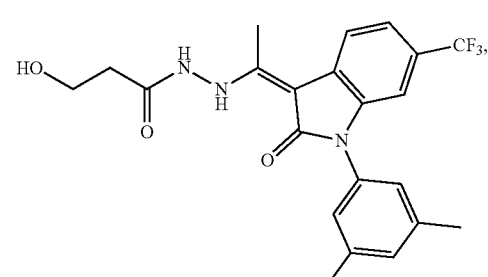
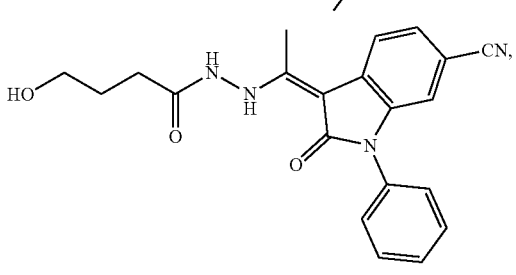

57
-continued
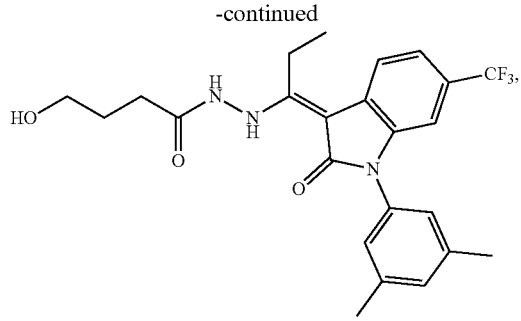
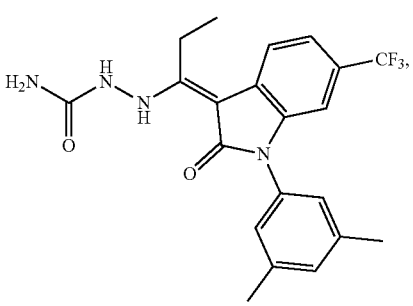
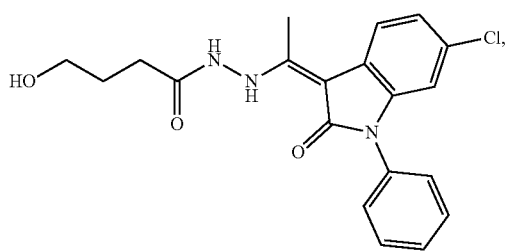
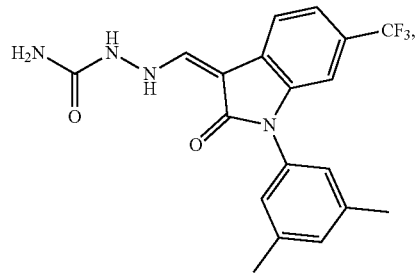
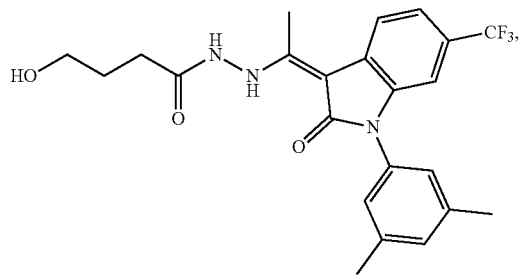
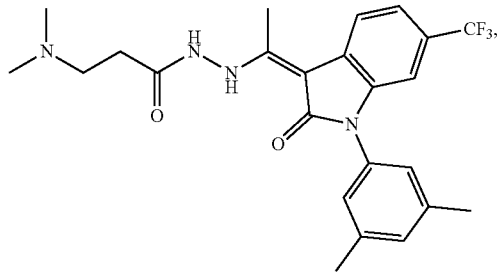
58
-continued
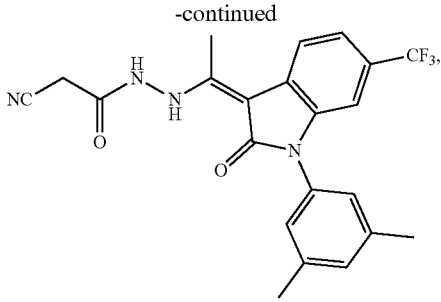
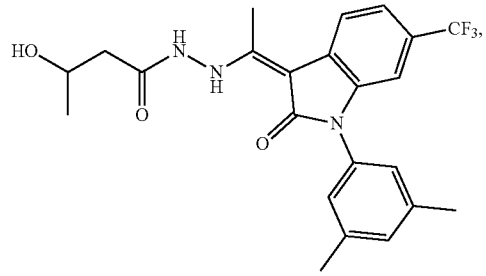
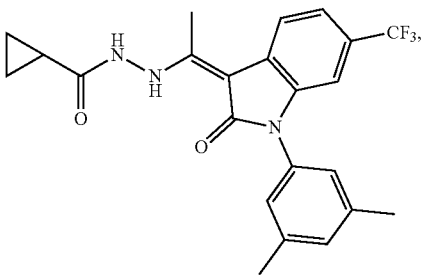
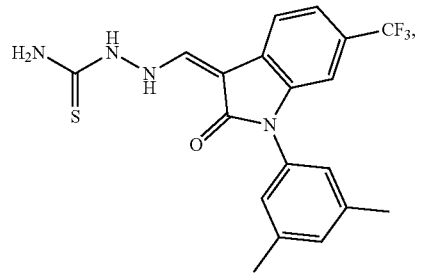
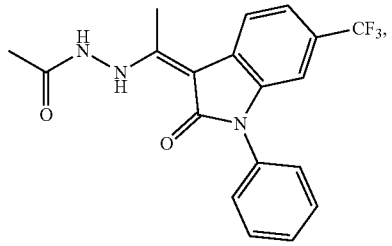
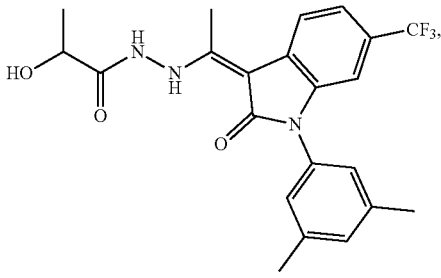

-continued
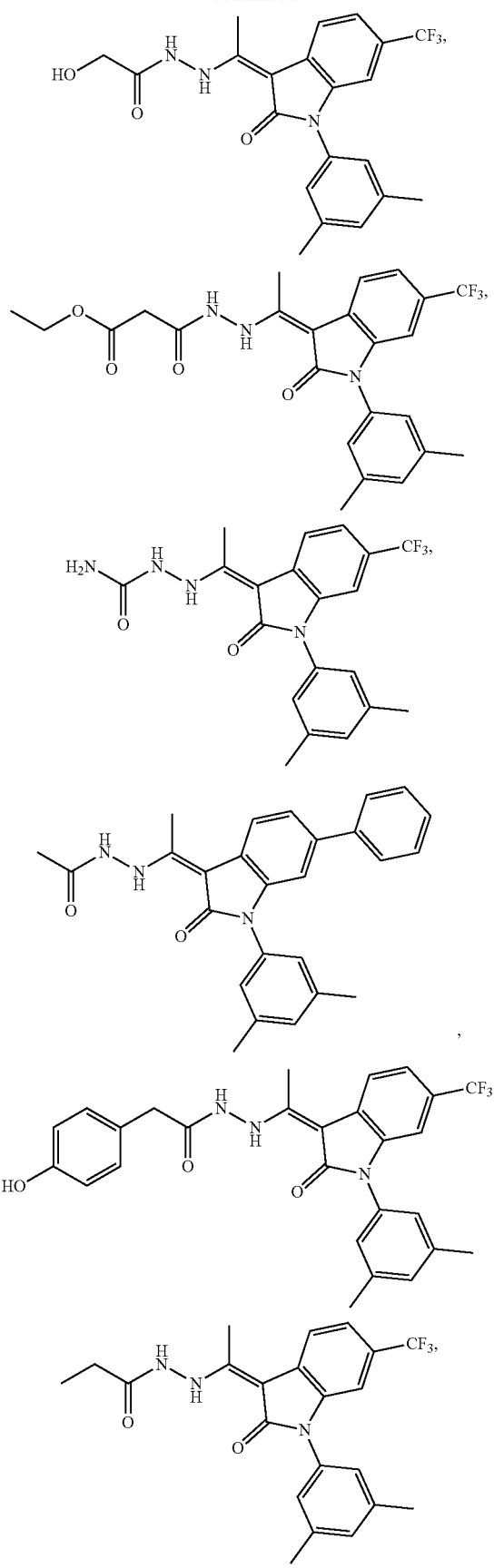
-continued
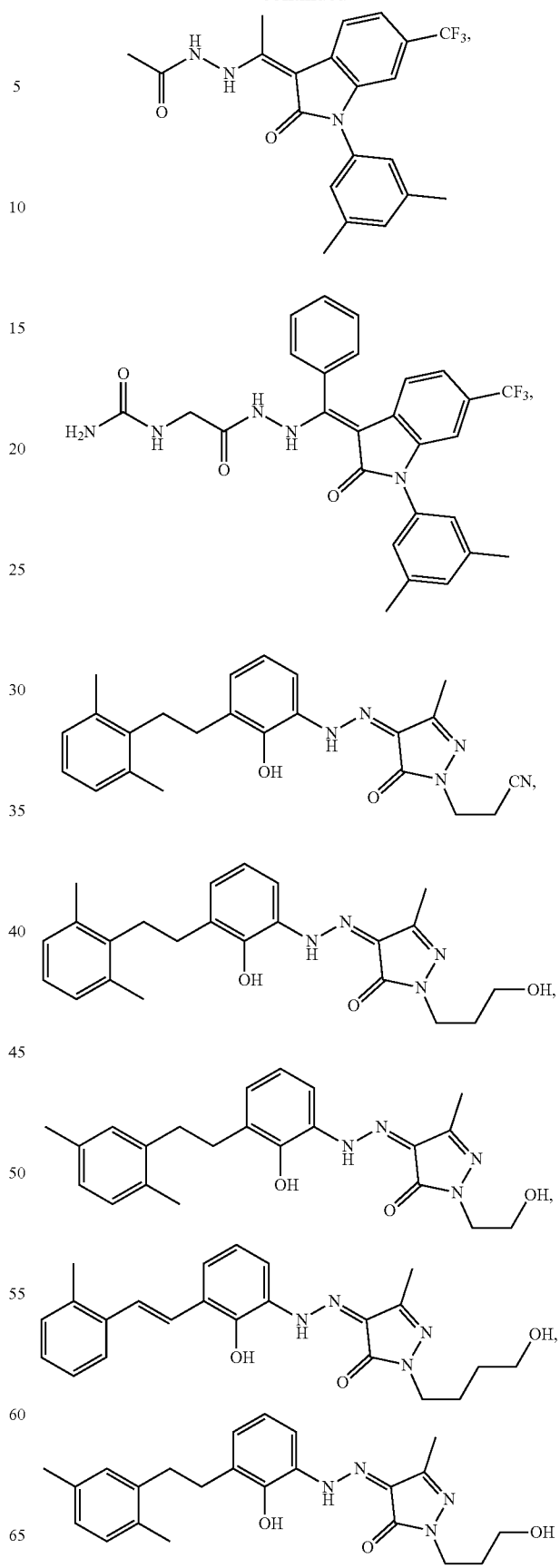

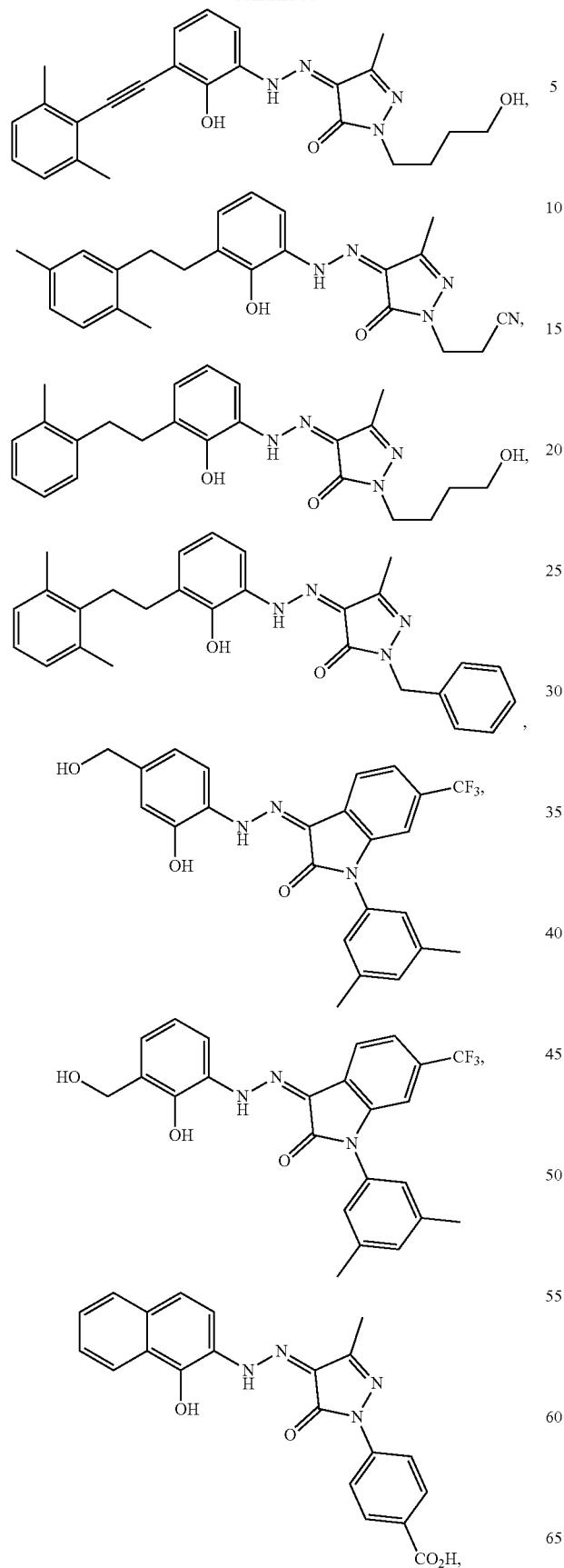
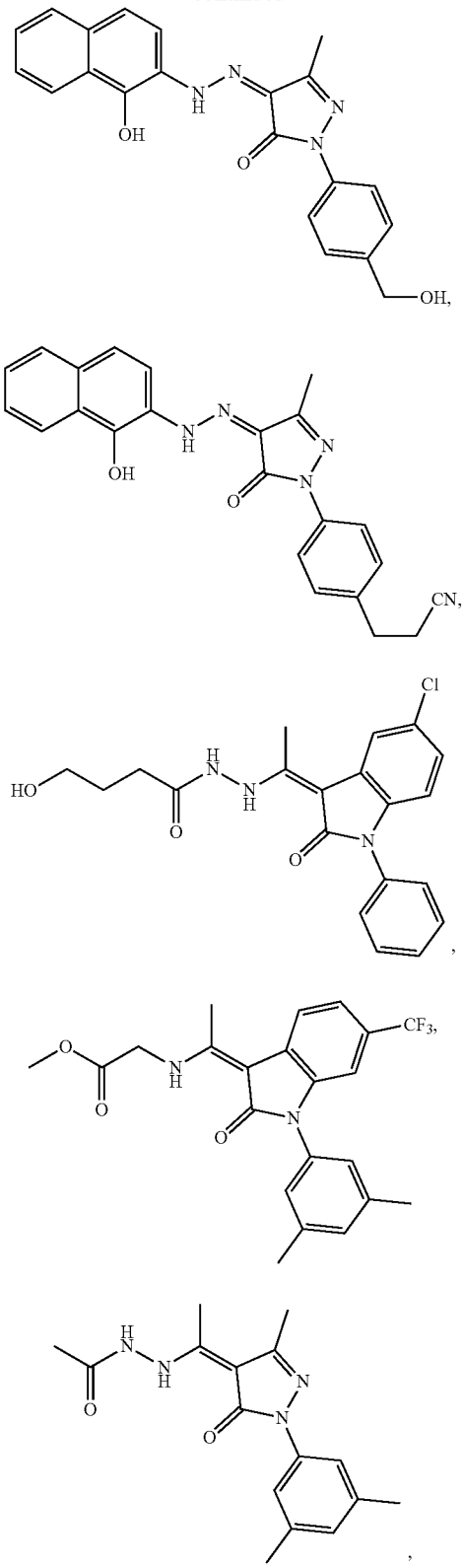
a tautomer thereof, or pharmaceutically acceptable salt thereof.
In some embodiments, the cytotoxic GCFR modulator is selected from:

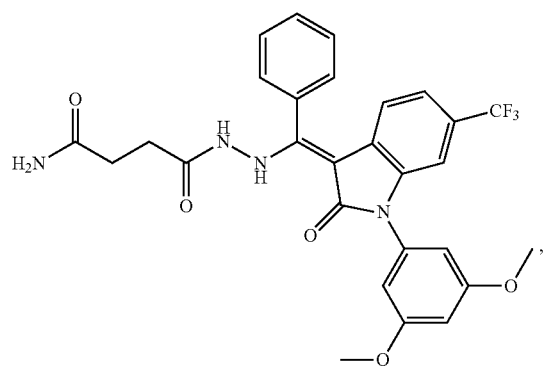
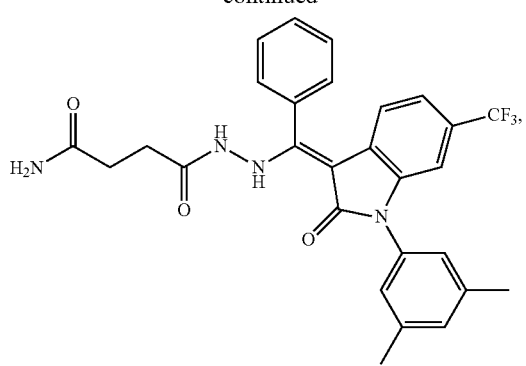
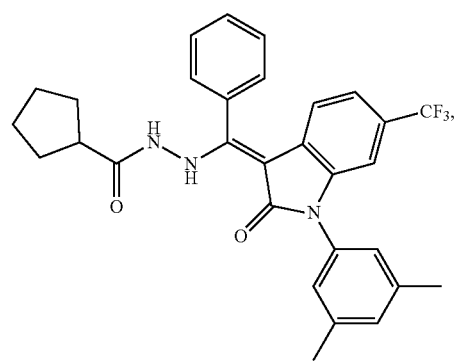
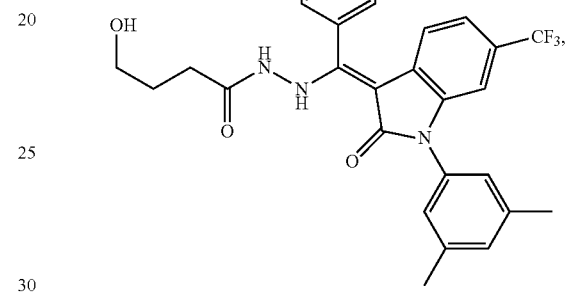
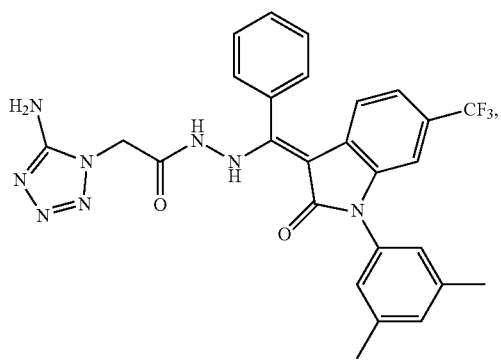
a tautomer thereof, or pharmaceutically acceptable salt thereof.
In some embodiments, the cytotoxic GCFR modulator is selected from:
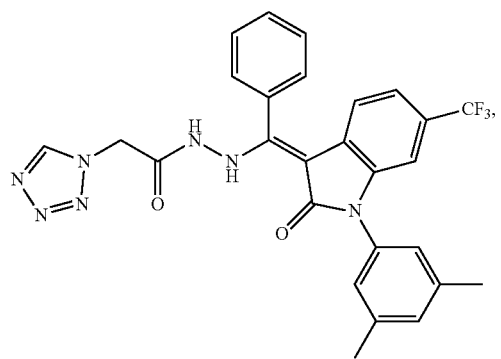
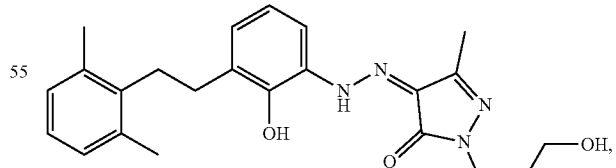
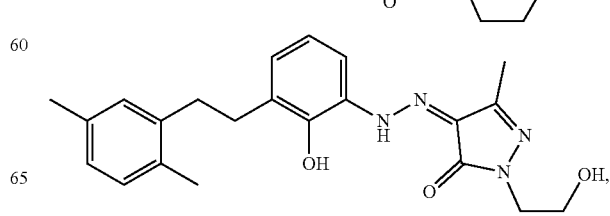

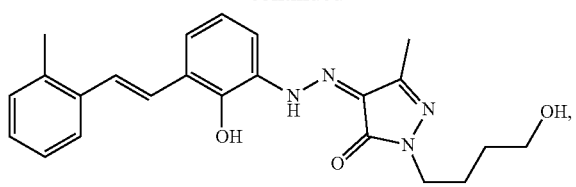
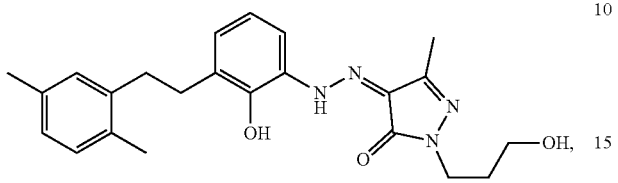
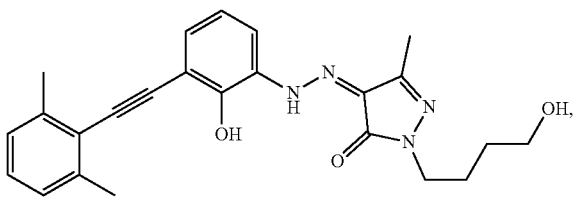
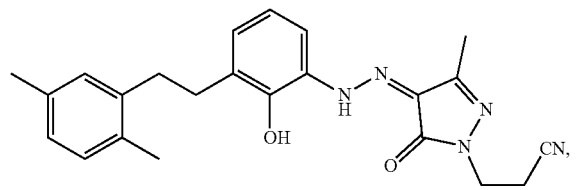
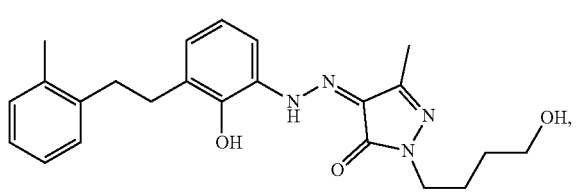
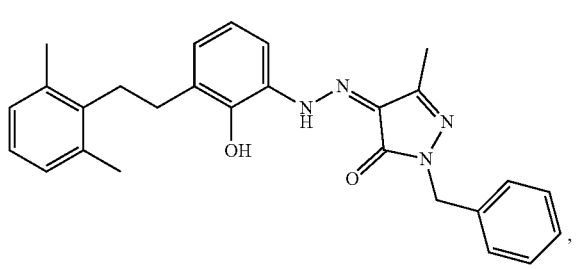
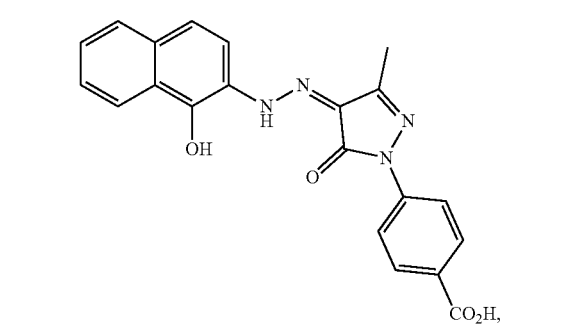
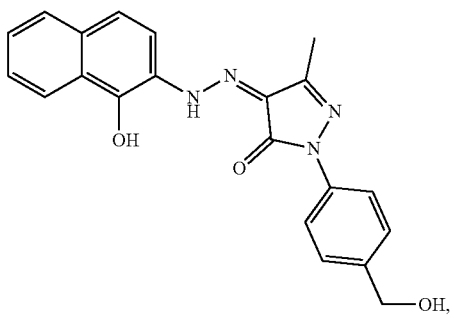
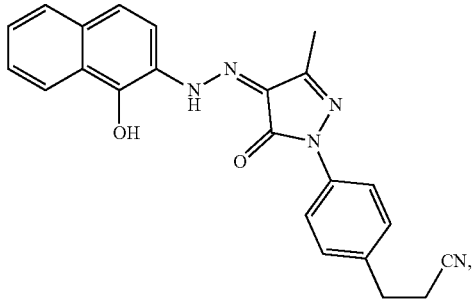
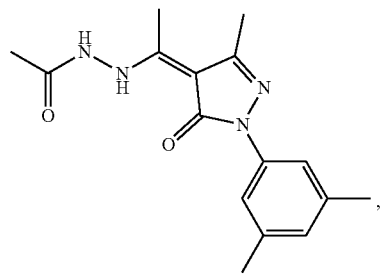
a tautomer thereof, or pharmaceutically acceptable salt thereof.
In some embodiments, the cytotoxic GCFR modulator is selected from
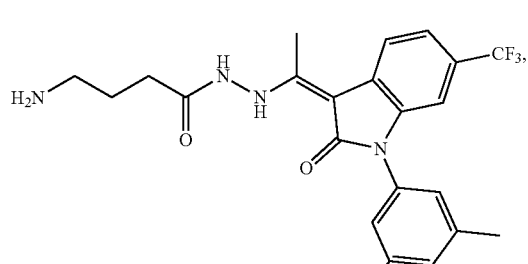
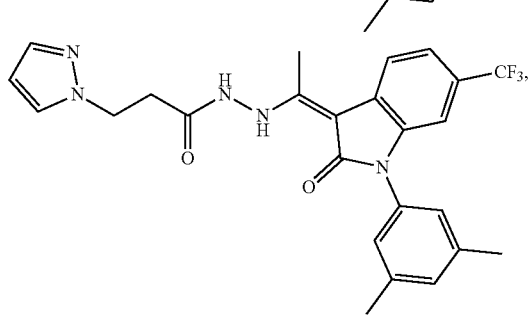

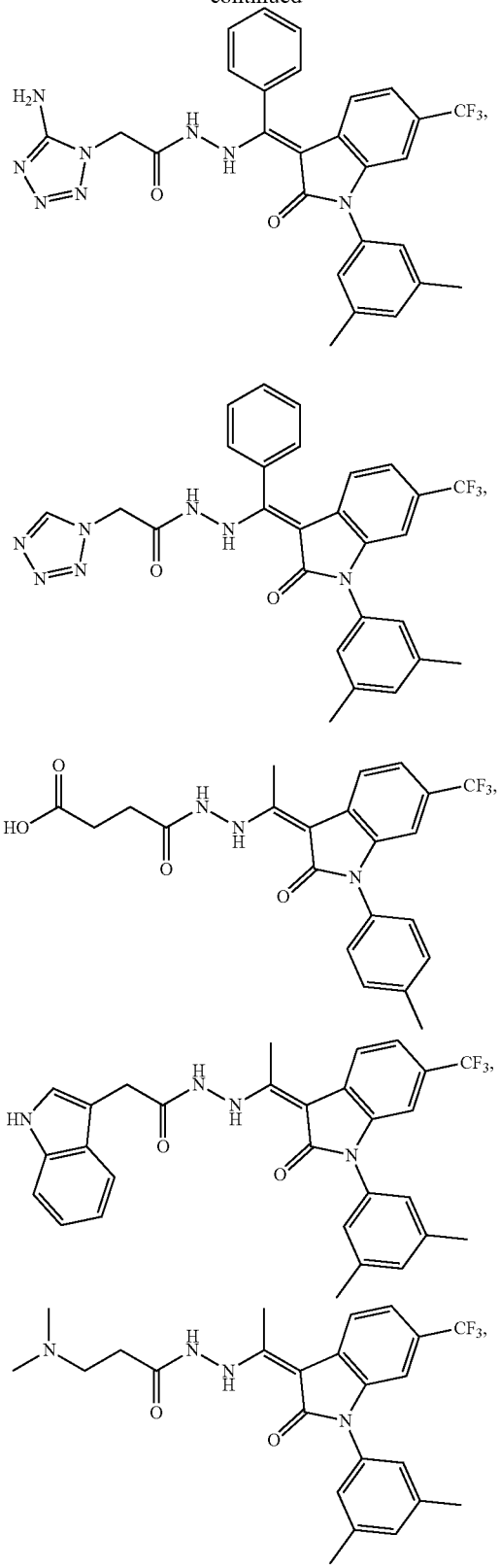

a tautomer thereof, or pharmaceutically acceptable salt thereof.

In certain embodiments, a salt corresponding to any of the compounds provided herein is provided. In certain embodiments, a salt corresponding to a selective cytotoxic GCFR modulator is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, tartaric acid and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a GCFR modulator with multiple molar equivalents of a base, such as bis-sodium, bis-ethanolamine, and the like. In certain embodiments, a salt is obtained by reacting a free base form of a GCFR modulator with multiple molar equivalents of an acid to afford a bis, tris, tetra, etc. salt.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

In certain embodiments, one or more carbon atoms of a compound of the present embodiments are replaced with silicon. See e.g., WO 03/037905A1; Tacke and Zilch, Endeavour, New Series, 10, 191-197 (1986); Bains and Tacke, Curr. Opin. Drug Discov Devel. July: 6(4):526-43 (2003), all of which are incorporated herein by reference in their entirety. In certain embodiments, compounds comprising one or more silicon atoms possess certain desired properties, including, but not limited to, greater stability and/or longer half-life in a patient, when compared to the same compound in which none of the carbon atoms have been replaced with a silicon atom.

In certain embodiments, compounds as disclosed herein can exist in tautomeric forms. All tautomeric forms are intended to be included in the scope of the compounds as disclosed herein. Likewise, when compounds contain a double bond, there exists the possibility of cis- and trans-type isomeric forms of the compounds. Both cis- and trans-isomers, both in pure form as well as mixtures of cis- and trans-isomers, are contemplated. Thus, reference herein to a compound includes all of the aforementioned isomeric forms unless the context clearly dictates otherwise.

In certain embodiments, a compound of Formula (I) can reside in one or more of the tautomeric forms. For example, the compound of Formula (I) can reside in the tautomeric forms shown below:

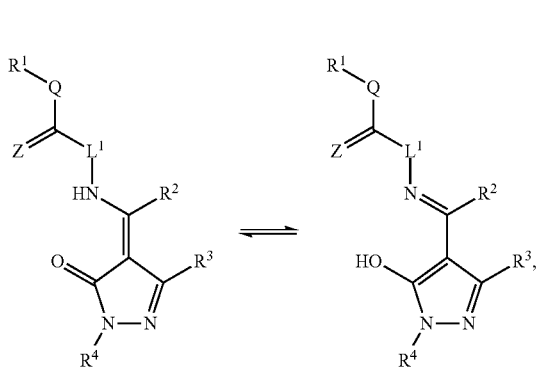
(I)

or their pharmaceutically acceptable salts.

In certain embodiments, a compound of Formula (II) can reside in one or more of the tautomeric forms. For example, the compound of Formula (II) can reside in the tautomeric forms shown below:

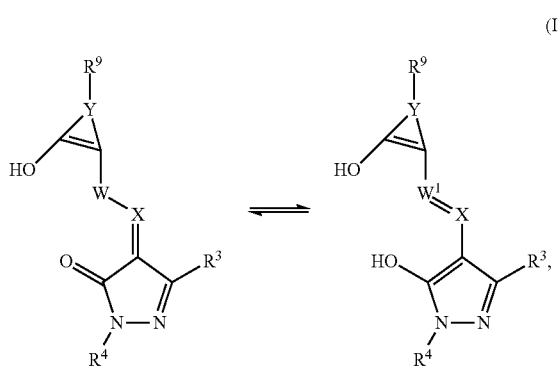
(II)

or their pharmaceutically acceptable salts, wherein W can be NH; and $W^1$ can be N (nitrogen).

In certain embodiments, a compound of Formula (III) can reside in one or more of the tautomeric forms. For example, the compound of Formula (III) can reside in the tautomeric forms shown below:

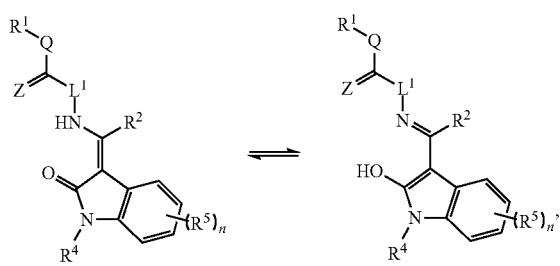
(III)

or their pharmaceutically acceptable salts.

In certain embodiments, a compound of Formula (IV) can reside in one or more of the tautomeric forms. For example, the compound of Formula (IV) can reside in the tautomeric forms shown below:

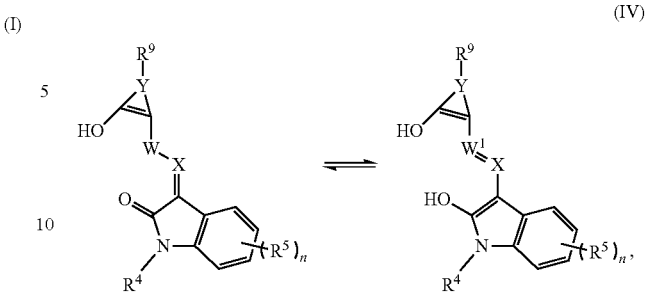
(IV)

or their pharmaceutically acceptable salts, wherein W can be NH; and $W^1$ can be N (nitrogen).

Certain Synthesis Methods

GCFR modulating compounds can be prepared and evaluated as described in International Application No. PCT/US2012/064706, which is incorporated herein by reference in its entirety for any purpose. One of skill in the art will recognize that analogous synthesis schemes may be used to prepare GCFR modulating compounds. One of skill will also recognize that GCFR modulating compounds may be synthesized using other synthesis schemes.

Certain Pharmaceutical Agents

In certain embodiments, a selective GCFR modulator, or pharmaceutically acceptable salt, ester, amide, and/or prodrug thereof, either alone or combined with one or more pharmaceutically acceptable carriers, forms a pharmaceutical agent. Techniques for formulation and administration of compounds of the present embodiments may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc. Pharmaceutically compatible salts may be formed with many bases, including but not limited to carbonates, sulfates, sulfites, phosphates, phosphites, hydroxides, ammonia, ammonium hydroxide, methylamine, etc. Several lists of pharmaceutically approved salts are widely available. See Bighley et al., Salt forms of drugs and absorption. 1996 In: Swarbrick J. et al. eds. *Encyclopaedia of pharmaceutical technology*, Vol. 13 New York: Marcel Dekker, Inc. pp 453-499; Gould, P. L., *Int. J. Pharm.* 1986, 33, 201-217; Berge, *J. Pharm. Sci.* 1977, 66, 1-19; Heinrich Stahl P., Wermuch C. G. (editors), Handbook of Pharmaceutical Salts, IUPAC, 2002; Stahl et al., Handbook of pharmaceutical salts: Properties, selection and use (2002) Weinheim/Zurich: Wiley-VCH/VHCA.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present embodiments is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a GCFR modulator in a dose from about 1 µg/kg of body weight to about 50 mg/kg of body weight. In certain embodiments, such dosage units comprise a GCFR modulator in a dose from about 2 µg/kg of body weight to about 25 mg/kg of body weight. In certain embodiments, such dosage units comprise a GCFR modulator in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present embodiments can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses. In some embodiments, a daily dosage regimen is characterized by the interval at which dosages are administered to achieve a therapeutically effective plasma concentration. In certain of such embodiments, the such an interval is achieved by dosing more than once daily, more than twice daily, more than three time daily, more than four times daily, more than five times daily, or dosing 2, 3, 4, 5, or 6 times daily, or daily dosing at a range bounded by any two of the aforementioned numbers. In some embodiments, more than one interval is combined to provide a dosage regimen that achieves a therapeutically effective plasma concentration. In certain of such embodiments, a first interval for dosing is followed by a second interval and optionally a third interval and/or a fourth interval, and/or additional intervals. The intervals for dosing may be utilized for 1, 2, 3, 4, 5, 6, or 7 days, or a range bounded by any two of the aforementioned numbers. In certain of such embodiments, two or more intervals are different from one of the other intervals.

In certain embodiments, a pharmaceutical agent of the present embodiments is administered by continuous intravenous infusion. In certain of such embodiments, from 0.1 mg to 500 mg of a composition of the present embodiments is administered per day. In certain of such embodiments 0.1 mg to 500 mg of a compound or composition of the present embodiments is administered to the subject per kg of the subject's body weight. In certain of such embodiments 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, or about any of the aforementioned numbers, or a range bounded by any two of the aforementioned numbers of a compound or composition of the present embodiments is administered to the subject per kg of the subject's body weight.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time. In some embodiments, the compound or composition is administered to a subject at an interval that achieves a therapeutically effective plasma concentration of the modulator in the subject's bloodstream over a period of time. In certain of such embodiments, the period of time that a therapeutically effective plasma concentration is achieved is 1 hour, or greater than 1, 2, 3, 4, 5, 6, 7, 8, 9, 10, 11, or twelve hours, or greater than 1 day, 2 days, 3 days, 4 days, 5 days, 6 days, or greater than 1 week, or about any of the aforementioned time periods, or a range bounded by any two of the aforementioned time periods. In some embodiments, the period of time that a therapeutically effective plasma concentration is achieved is less than 1, 2, 3, 4, 5, 6, 7, 8, 9, 10, 11, or twelve hours, or less than 1 day, 2 days, 3 days, 4 days, 5 days, 6 days, or less than 1 week, or about any of the aforementioned time periods, or a range bounded by any two of the aforementioned time periods.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Combination Therapies

In certain embodiments, one or more pharmaceutical agents of the present embodiments are co-administered with one or more other pharmaceutical agents. In certain embodiments, such one or more other pharmaceutical agents are designed to treat the same disease or condition as the one or more pharmaceutical agents of the present embodiments. In certain embodiments, such one or more other pharmaceutical agents are designed to treat a different disease or condition as the one or more pharmaceutical agents of the present embodiments. In certain embodiments, such one or more other pharmaceutical agents are designed to treat an undesired effect of one or more pharmaceutical agents of the present embodiments. In certain embodiments, one or more pharmaceutical agents of the present embodiments are co-administered with another pharmaceutical agent to treat an undesired effect of that other pharmaceutical agent. In certain embodiments, one or more pharmaceutical agents of the present embodiments and one or more other pharmaceutical agents are administered at the same time. In certain embodiments, one or more pharmaceutical agents of the present embodiments and one or more other pharmaceutical agents are administered at the different times. In certain embodiments, one or more pharmaceutical agents of the present embodiments and one or more other pharmaceutical agents are prepared together in a single formulation. In certain embodiments, one or more pharmaceutical agents of the present embodiments and one or more other pharmaceutical agents are prepared separately.

Examples of pharmaceutical agents that may be co-administered with a pharmaceutical agent of the present embodiments include, but are not limited to, anti-cancer treatments, including, but not limited to, chemotherapy and radiation treatment; corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors);

salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In some embodiments, the compounds provided herein can be administered in combination with an additional therapeutic regimen. In some such embodiments, the additional therapeutic regimen can include chemotherapy, bone marrow transplantation, and radiation therapy. In certain embodiments, a compound provided herein can be administered to a subject in combination with harvesting peripheral blood progenitor cells and/or in conjunction with hematopietic stem cell transplantation. Such administration may be done before, during, and/or after such harvesting.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA is selected by measuring a biomarker in the patient. The term biomarker includes, but is not limited to, genetic regulation, protein levels, RNA levels, and cellular responses such as cytotoxicity. In some embodiments, one or more chemotherapeutic agents are selected by subjecting a sample from the patient to a companion diagnostic device. In some embodiments, the sample is a tissue sample, such as blood. In other embodiments, the tissue sample is representative of the cancer to be treated. In some embodiments, the tissue sample contains a portion of the cancer to be treated. In some embodiments, the tissue sample is not cancerous.

Additional Embodiments

Some embodiments describe a method of treating a hematopoietic disorder, comprising: administering a therapeutically effective cytotoxic amount of a GCFR modulator to a subject in need thereof.

With respect to the above-described method, in some embodiments the GCFR modulator is administered to a subject in need thereof at an interval that achieves a therapeutically effective plasma concentration of the modulator in the subject's bloodstream over a period of time.

With respect to the above-described methods, some embodiments describe a method of treating a hematopoietic disorder, comprising: administering a therapeutically effective amount of a GCFR modulator to a subject in need thereof at an interval that achieves a therapeutically effective plasma concentration of the modulator in the subject's bloodstream over a period of time.

With respect to the above-described methods, some embodiments describe a method wherein the period of time is greater than 1 hour.

With respect to the above-described methods, some embodiments describe a method wherein the period of time is greater than 3 hours.

With respect to the above-described methods, some embodiments describe a method wherein the period of time is greater than 6 hours.

With respect to the above-described methods, some embodiments describe a method wherein the period of time is greater than 9 hours.

With respect to the above-described methods, some embodiments describe a method wherein the period of time is greater than 1 day.

With respect to the above-described methods, some embodiments describe a method wherein the period of time is greater than 2 days.

With respect to the above-described methods, some embodiments describe a method wherein the period of time is greater than 3 days.

With respect to the above-described methods, some embodiments describe a method wherein the period of time is greater than 1 week.

With respect to the above-described methods, some embodiments describe a method wherein the period of time is less than 1 week.

With respect to the above-described methods, some embodiments describe a method wherein the hematopoietic disorder is a granulocytopenia.

With respect to the above-described methods, some embodiments describe a method wherein the hematopoietic disorder is neutropenia.

With respect to the above-described methods, some embodiments describe a method wherein the interval that achieves a therapeutically effective plasma concentration of the modulator is dosing more than one time daily.

With respect to the above-described methods, some embodiments describe a method wherein the interval that achieves a therapeutically effective plasma concentration of the modulator is dosing more than two times daily.

With respect to the above-described methods, some embodiments describe a method wherein the interval that achieves a therapeutically effective plasma concentration of the modulator is dosing 2-6 times daily.

With respect to the above-described methods, some embodiments describe a method wherein the interval that achieves a therapeutically effective plasma concentration of the modulator is dosing 2-5 times daily.

With respect to the above-described methods, some embodiments describe a method wherein the interval that achieves a therapeutically effective plasma concentration of the modulator is dosing 2-4 times daily.

With respect to the above-described methods, some embodiments describe a method wherein the interval that achieves a therapeutically effective plasma concentration of the modulator is dosing two, three, four, five, or six times daily.

With respect to the above-described methods, some embodiments describe a method wherein the interval that achieves a therapeutically effective plasma concentration of the modulator is dosing three times daily.

With respect to the above-described methods, some embodiments describe a method wherein the GCFR modulator is administered at a first interval for 1-5 days, wherein the first interval is the interval described herein, followed by administration at a second interval that is different from the first interval.

With respect to the above-described methods, some embodiments describe a method wherein the GCFR modulator is administered at the first interval for 2, 3, 4, or 5 days, and the administration at the second interval is once daily dosing.

With respect to the above-described methods, some embodiments describe a method wherein the GCFR modulator is administered at the first interval for three days, and the administration at the second interval is once daily dosing.

With respect to the above-described methods, some embodiments describe a method wherein the therapeutically effective plasma concentration of the modulator is the in vitro $EC_{50}$ of the modulator.

With respect to the above-described methods, some embodiments describe a method wherein about 0.5-4 mg of the GCFR modulator per kg of the subject's body weight is administered to the subject at each interval.

With respect to the above-described methods, some embodiments describe a method wherein about 1-3 mg of the GCFR modulator per kg of the subject's body weight is administered to the subject at each interval.

With respect to the above-described methods, some embodiments describe a method wherein about 2 mg of the GCFR modulator per kg of the subject's body weight is administered to the subject at each interval.

With respect to the above-described methods, some embodiments describe a method wherein the GCFR modulator, or a pharmaceutically acceptable salt thereof, or a pharmaceutical composition thereof is administered in combination with one or more additional therapeutic regimens.

With respect to the above-described methods, some embodiments describe a method wherein the additional therapeutic regimen is selected from the group consisting of chemotherapy, bone marrow transplantation, and radiation therapy.

With respect to the above-described methods, some embodiments describe a method wherein the additional therapeutic regimen is chemotherapy.

With respect to the above-described methods, some embodiments describe a method wherein the chemotherapy comprises administering an agent selected from the group consisting of alkylating agents, anthracyclines, cytoskeletal disruptors, epothilones, histone deacetylase inhibitors, topoisomerase inhibitors, kinase inhibitors, monoclonal antibodies, nucleotide analogs, peptide antibiotics, platinum-based agents, retinoids, and vinca alkaloids.

With respect to the above-described methods, some embodiments describe a method wherein the chemotherapy comprises administering one or more agents selected from the group consisting of gemcitabine, cytarabine, cisplatin, methotrexate, 6-mercaptopurine, chlorambucil, cyclophosphamide, fludarabine, pentostatin, cladribine, imatinib, rituximab, interferon-alpha, doxorubicin, vincristine, prednisone, etoposide, bleomycin, or Alemtuzumab.

With respect to the above-described methods, some embodiments describe a method wherein the GCFR modulator is selected by measuring a biomarker in the patient.

With respect to the above-described methods, some embodiments describe a method wherein the biomarker is a cellular response to the GCFR agonist or partial agonist.

With respect to the above-described methods, some embodiments describe a method wherein the cellular response is cytotoxicity.

With respect to the above-described methods, some embodiments describe a method further comprising selecting one or more chemotherapeutic agents by subjecting a sample from the patient to a companion diagnostic device.

With respect to the above-described methods, some embodiments describe a method wherein the companion diagnostic device measures a biomarker in the patient.

With respect to the above-described methods, some embodiments describe a method wherein the biomarker is a cellular response to one or more chemotherapeutic agents.

With respect to the above-described methods, some embodiments describe a method wherein the cellular response is cytotoxicity.

With respect to the above-described methods, some embodiments describe a method wherein the subject is diagnosed as having cancer.

With respect to the above-described methods, some embodiments describe a method wherein the subject is undergoing cancer treatment.

With respect to the above-described methods, some embodiments describe a method wherein the subject is in need of both hematopoietic disorder treatment and cancer treatment.

With respect to the above-described methods, some embodiments describe a method wherein the subject has a cancer as described herein.

With respect to the above-described methods, some embodiments describe a method wherein the cytotoxic GCFR modulator is as described herein.

EXAMPLES

Certain Methods of Identifying GCFR Modulators

Methods for identifying GCFR modulators are described in detail in International Application No. PCT/US2012/064706.

Certain Assays

In certain embodiments, assays may be used to determine the level of GCFR modulating activity of compounds useful for the present embodiments. Assays containing selectively mutated GCSFR may be used to determine the interaction of the compounds with the TM domain. Assays containing GCSFR from species different than human may be used to measure the activity of the compounds (e.g. mouse or monkey). Such assays are described in International Application No. PCT/US2012/064706.

Cell Proliferation Assay

In some embodiments, compounds are tested in an in vitro proliferation assay to determine anti-proliferative activity. See, e.g., Drug. Dev. Res. 1995, 34, 91-109; *J. Natl. Cancer Inst.* 1990, 82, 1107-1112; Drug Dev. Res. 1995, 34, 91-109. As an illustration, cells of approximately 60 different human cancer cell lines are incubated for 48 hours with five 10-fold dilutions of the investigated compound, starting from 100 µM concentrations, and then treating with sulforhodamine B dye. The ratios of recorded optical densities relative to that of a control are plotted as a function of the common logarithm of the investigated compound concentrations. The interpolation between the points located above and below the 50% percentage growth provide 50% growth inhibition ($GI_{50}$) values. Total growth inhibition (TGI) and 50% lethal concentrations ($LC_{50}$) are also amenable to calculation using reported methods.

Cell Growth Inhibition

The human acute promyelocytic leukemia cell line HL-60, the acute myeloid leukemia cell line Kasumi-1, the lung carcinoma cell line A549, the embryonic kidney cell line HEK293, and the hepatocellular carcinoma cell line HepG2 were purchased from ATCC. HL-60 and A549 cells were grown in RPMI-1640 media containing 10% fetal bovine serum (FBS). Kasumi-1 cells were grown in RPMI-1640 media containing 20% FBS. HEK293 and HepG2 cells were grown in Eagles Minimal Essential Media containing 10% FBS. Cells were plated in 96-well microtiter plates at a density of either 2000 cells/well (A549 cells) or 5000 cells/well and incubated overnight at 37° C. Cell growth was measured by the ATPlite™ istep Kit (PerkinElmer, Waltham, Mass.) according to the manufacturer's instructions. ATPlite™ uses firefly luciferase to indirectly quantify the level of adenosine triphosphate (ATP) as a measure of proliferation and cytotoxicity of cultured mammalian cells. Compounds were diluted in the appropriate cell culture media for each cell type at incremental concentrations ranging from 0.1 nM to 100 tiM. Diluted compounds were added to the various cell types, and the cells were incubated for 72 hours at 37° C. ATPlite™ reagent was added to the cells, and the cells were incubated for 4 minutes on a plate shaker. Luminescence, quantified as relative luciferase units (RLU), was measured on an Envision plate reader (PerkinElmer). For each replicate, the mean and standard deviation of the RLU at each concentration of compound was calculated. The data was plotted graphically as the mean RLU of the compound over the range of the concentration-response curve. For cell growth inhibition, the concentration of test compound that resulted in 50% of the maximum inhibition observed ($IC_{50}$) was determined for each compound by 4-parameter fit of the concentration-response curve.

Results of the above described assay utilizing Compound 101 are provided in Table 1:

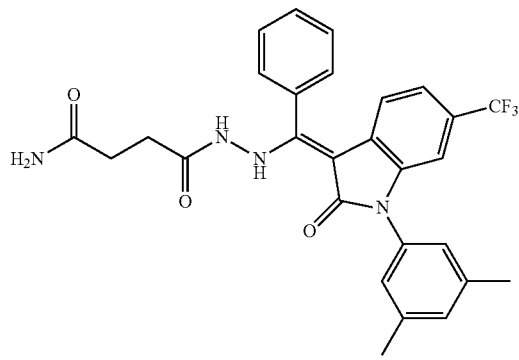

Compound 101

TABLE 1

The anti-proliferative potency ($IC_{50}$) of Compound 101 on various tumor cell lines of diverse origin
Inhibition of Tumor Cell Growth ($IC_{50}$, µM)

| | HL-60 (n = 5) | Kasumi-1 (n = 3) | A549 (n = 3) | HEK293 (n = 3) | HEPG2 (n = 3) |
|---|---|---|---|---|---|
| Compound 101 | 5.0 ± 2.8 | 12.1 ± 2.4 | 6.1 ± 2.5 | 1.4 ± 0.04 | 0.9 ± 0.1 |

To arrive at the information in Table 1, the indicated cells were plated in 96-well microtiter plates in media containing 10% FBS at a density of 2000 cells/well for A549 and 5000 cells/well for the other cell lines. The next day, increasing concentrations of the test compound, diluted in cell plating media, were added to the cells. Cells were incubated with compound for 72 hours. Cell growth was measured using the ATPlite™ 1 step Kit. Relative light units (RLU) are the mean±SD of 2 replicates at each concentration. The anti-proliferative potency ($IC_{50}$) of the test compound was calculated in the cell growth assays. Values shown are the mean±SEM $IC_{50}$ (µM) calculated from the indicated number (n) of independent experiments. The results indicate that Compound 101 has low micromolar to sub-micromolar (high nanomolar) cellular inhibition against a variety of diverse cancer cell lines.

The dose response curve for Compound 101 against HL-60 cancer cells is provided in FIG. 1. HL-60 cells were plated in 96-well microtiter plates in RPMI-1640 media containing 10% FBS at a density of 5000 cells/well. The next day, increasing concentrations of the test compound, 101, were diluted in cell plating media, and were added to the cells. Cells were incubated in the presence or absence of compound for 72 hours. Cell growth was measured using the ATPlite™ istep Kit. Relative light units (RLU) are the mean±SD of 2 replicates at each concentration. Blank represents the response in the absence of test compound. As indicated in FIG. 1, Compound 101 exhibited a dose-dependent effect on cancer (i.e. HL-60) cell growth. Thus, Compound 101 was substantially more effective than no dose, illustrated in FIG. 1 by the dotted line (denoted as "Blank").

Induction of Apoptosis

Figure 2:
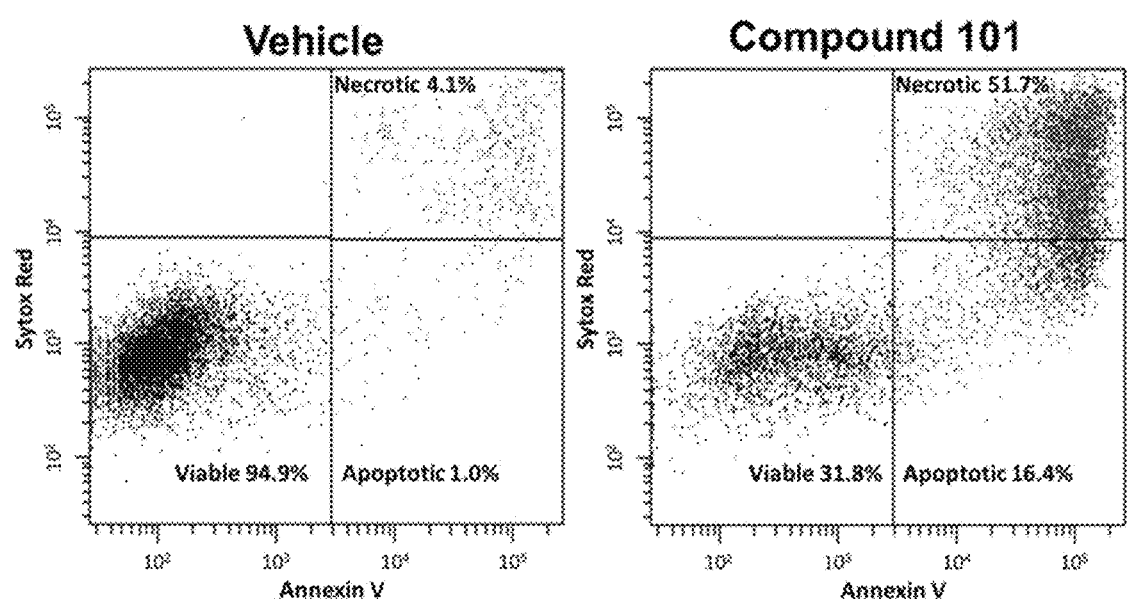
FIG. 2 describes the increase in apoptosis resulting from treatment of HL-60 cells with Compound 101.

HL-60 cells were incubated under similar conditions to the cell growth assay described above (i.e. 50,000 cell/well of a 24-well plate, incubated in cell culture media in the presence of vehicle or compound for 48 hours at 37° C. in an incubator with 5% $CO_2$). Apoptosis was determined by using Annexin V/Sytox Red staining (Life Technologies/Invitrogen) followed by assaying with fluorescence-activated cell sorting (FACS) according to standard protocols. In this assay, vehicle constituted DMSO and the test compound (Compound 101) was diluted to 10 µM with cell culture media from a 10 mM stock solution of Compound 101 in DMSO. The results of the apoptosis assay are described in FIG. 2. From FIG. 2, it is evident that as compared to the vehicle, Compound 101 dramatically increased the percentage of HL-60 cells classified as either apoptotic or necrotic in the assay. Compound 101 decreased the number of viable cells in the assay by over 60% and produced nearly a 50% increase in necrotic cells and over a 15% increase in apoptotic cells. Accordingly, the results indicate that Compound 101 is a potent inductor of apoptosis and necrosis in cancer cells.

Blood Cell Induction

Figure 3:
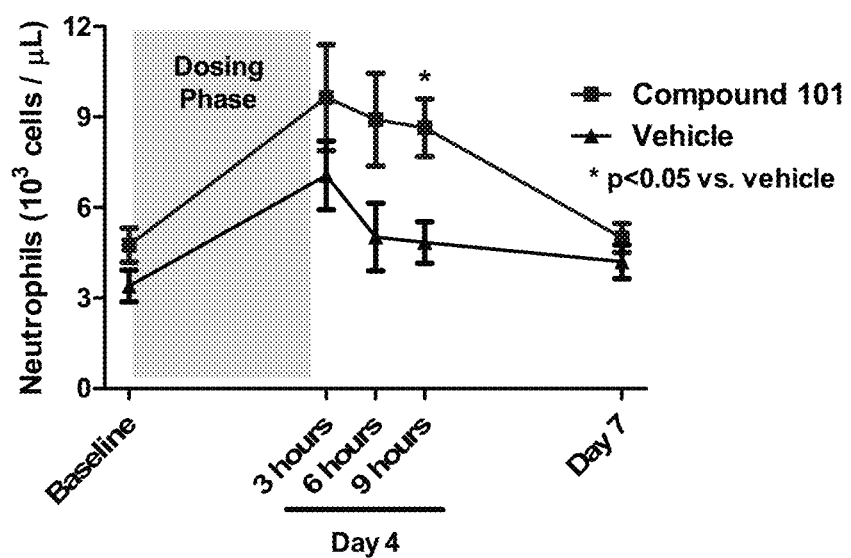
FIG. 3 illustrates the effect of TID dosing of Compound 101 on neutrophil count in an animal model.

Test compound was evaluated in an animal model for the ability to increase blood cell count, and particularly peripheral blood neutrophils, according to the following protocol. A test compound (Compound 101) was formulated in DMSO:PEG400:PBS at a concentration of 2 mg/mL. Cynomolgus monkeys where then dosed with either vehicle or the test compound via an IV injection for three days. Doses were administered in the morning and then at 5, and 10 hours later. On Day four, a single dose was administered. Blood samples were then collected at the start of the experiment, at Day 4 at 3 hours, 6 hours, and 9 hours after the single dose, and at Day 7. Blood samples were collected and analyzed on a commercial hematology system (ADVIA 2120). The results for neutrophil evaluation are graphically represented in FIG. 3 for both vehicle and Compound 101. After the three day dosing phase, Compound 101 induced a higher neutrophil count than vehicle, which was statistically significant at the 9 hour time point on Day 4. Following three days without dosing of Compound 101 (represented at the Day 7 time point), the neutrophil count returned to a level similar to the vehicle. According, the data indicates that Compound 101 provided a significant increase in neutrophil count.

Following the above-described protocols, growth inhibition, antiproliferative activity, apoptosis and necrosis induction, and neutrophil counts are measured for the disclosed class of GCFR modulators. Therefore, and in accordance with FIGS. 1-3 and Table 1, the disclosed GCFR modulators represent a novel class of compounds having cytotoxic activities across a variety of cancerous cell lines as well as the ability to stimulate blood cell induction.

What is claimed is:

1. A method for treating a cancer selected from the group consisting of a leukemia, non-small cell lung cancer, colon cancer, CNS cancer, skin cancer, ovarian cancer, renal cancer, prostate cancer, breast cancer, and myeloma, comprising administering to a subject in need thereof an effective amount of a pharmaceutical composition comprising a compound of Formula (I), (II), Ill, or (IV) in combination with an additional therapeutic agent selected from the group consisting of a chemotherapeutic agent, bone marrow transplant, and radiation therapy, wherein the compound of Formula (I), (II), Ill, or (IV) has the structure:

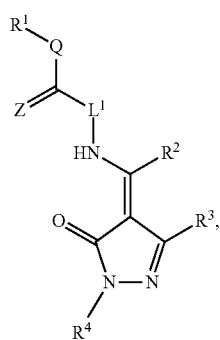

(I)

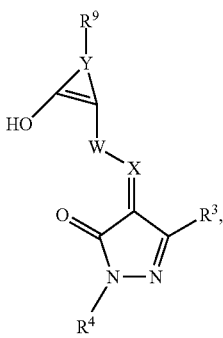

(II)

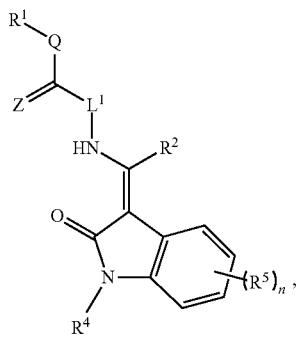

(III)

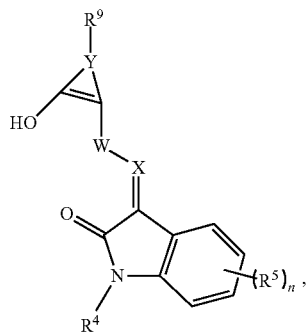

(IV)

a tautomer thereof, or a pharmaceutically acceptable salt thereof, wherein:

$R^1$ is selected from hydrogen, $OR^6$, $NO_2$, CN, $NR^6R^7$, $CO_2R^6$, $C(=O)NR^6R^7$, $SO_3R^6$, $SO_2NR^6R^8$, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted arylalkyl, an optionally substituted aryl, and an optionally substituted heteroaryl;

$R^2$ and $R^3$ are independently selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, an optionally substituted heteroaryl, an optionally substituted arylalkyl, an optionally substituted arylalkenyl, an optionally substituted arylalkynyl, and an optionally substituted heteroarylalkyl;

$R^5$ is selected from hydrogen, halogen, $NO_2$, CN, $CF_3$, $OR^6$, $CO_2R^6$, $C(=O)NR^6R^7$, $SO_3R^6$, and $SO_2NR^6R^8$, an optionally substituted aryl, an optionally substituted $C_1$-$C_6$ alkyl, and an optionally substituted $C_1$-$C_6$ heteroalkyl;

$R^6$ is selected from hydrogen, an optionally substituted $C_1$-$C_6$ alkyl, a $C_1C_6$ heteroalkyl, an optionally substituted aryl, and an optionally substituted heteroaryl;

$R^7$ is selected from hydrogen, $C(=O)R^8$, $C(=O)NHR^8$, an optionally substituted $C_1$-$C_6$ alkyl, and an optionally substituted $C_1$-$C_6$ heteroalkyl; or $-NR^6R^7$ is an optionally substituted non-aromatic heterocycle linked through a ring nitrogen;

$R^8$ is selected from hydrogen, an optionally substituted $C_1$-$C_6$ alkyl, and an optionally substituted $C_1$-$C_6$ heteroalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

Q is selected from the group consisting of $NR^6$, an optionally substituted $C_1$-$C_6$ alkyl, an optionally substituted $C_3$-$C_8$ cycloalkyl, an optionally substituted $C_1$-$C_6$ heteroalkyl, and an optionally substituted non-aromatic heterocycle;

$L^1$ is selected from NH and $CHR^2$;

W is selected from O (oxygen) and NH;

X is N (nitrogen) or $CR^2$;

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl;

Z is O (oxygen) or S (sulfur); and n is 1, 2 or 3.

2. The method of claim 1, wherein the chemotherapeutic agent is selected from the group consisting of an alkylating agent, anthracycline, cytoskeletal disruptor, epothilone, histone deacetylase inhibitor, topoisomerase inhibitor, kinase inhibitor, monoclonal antibody, nucleotide analog, peptide antibiotic, platinum-based agent, retinoid, and vinca alkaloid.

3. The method of claim 1, wherein the chemotherapeutic agent is selected from the group consisting of gemcitabine, cytarabine, cisplatin, methotrexate, 6-mercaptopurine, chlorambucil, cyclophosphamide, fludarabine, pentostatin, cladribine, imatinib, rituximab, interferon-alpha, doxorubicin, vincristine, prednisone, etoposide, bleomycin, and alemtuzumab.

4. The method of claim 1, wherein the pharmaceutical composition and the additional therapeutic agent are administered sequentially.

5. The method of claim 1, wherein the pharmaceutical composition and the additional therapeutic agent are administered concurrently.

6. The method of claim 1, wherein the pharmaceutical composition is administered intravenously.

7. The method of claim 1, wherein the pharmaceutical composition is administered orally.

8. The method of claim 1, wherein the pharmaceutical composition comprises a component selected from the group consisting of a polyethylene glycol, an organic solvent, and a surfactant.

9. The method of claim 1, wherein the leukemia is selected from the group consisting of chronic lymphocytic leukemia (CLL), chronic myeloid leukemia (CML), acute lymphocytic leukemia (ALL), acute myeloid leukemia (AML), T-cell prolymphocytic leukemia, large granular lymphocytic leukemia, adult T-cell leukemia, juvenile myelomonocytic leukemia, and hairy cell leukemia.

10. The method of claim 1, wherein the compound has the structure of Formula (Ia):

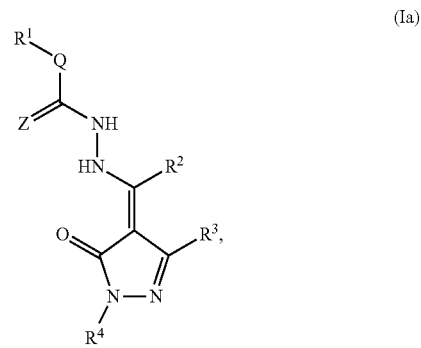

(Ia)

a tautomer thereof, or a pharmaceutically acceptable salt thereof, wherein:

$R^1$ is selected from hydrogen, an optionally substituted $C_1$-$C_6$ alkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted aryl, and an optionally substituted heteroaryl;

$R^2$ and $R^3$ are independently selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl; and Q is selected from an optionally substituted $C_1$-$C_6$ alkyl, an optionally substituted $C_3$-$C_8$ cycloalkyl, and an optionally substituted non-aromatic heterocycle.

11. The method of claim 1, wherein the compound has the structure of Formula (IIa) or (IIb):

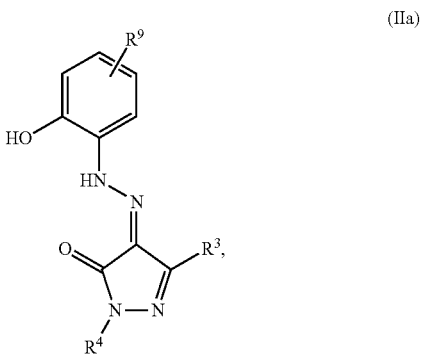

(IIa)

-continued (IIb)

a tautomer thereof, or a pharmaceutically acceptable salt thereof,
wherein:
$R^3$ is selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;
$R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl; and
$R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

12. The method of claim 1, wherein the compound has the structure of Formula (IIIa):

(IIIa)

a tautomer thereof, or a pharmaceutically acceptable salt thereof,
wherein:
$R^1$ is selected from hydrogen, $OR^6$, $NR^6R^7$, $CO_2R^6$, $C(\!=\!O)NR^6R^7$, an optionally substituted $C_2$-$C_6$ heterocyclyl, an optionally substituted arylalkyl, an optionally substituted aryl, and an optionally substituted heteroaryl;
$R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl;

$R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl;
$R^5$ is selected from hydrogen, halogen, CN, $CF_3$, $OR^6$, an optionally substituted aryl, and an optionally substituted $C_1$-$C_6$ alkyl;
$R^6$ is selected from hydrogen, an optionally substituted $C_1$-$C_6$ alkyl, an optionally substituted aryl, and an optionally substituted heteroaryl;
$R^7$ is selected from hydrogen, $C(\!=\!O)R^8$, $C(\!=\!O)NHR^8$, and an optionally substituted $C_1$-$C_6$ alkyl; or —$NR^6R^7$ is an optionally substituted non-aromatic heterocycle linked through a ring nitrogen;
$R^8$ is selected from hydrogen, and an optionally substituted $C_1$-$C_6$ alkyl;
Q is selected from $NR^6$, an optionally substituted $C_1$-$C_6$ alkyl, an optionally substituted $C_3$-$C_8$ cycloalkyl, and an optionally substituted non-aromatic heterocyclyl; and
n is 1, or 2.

13. The method of claim 1, wherein the compound has the structure of Formula (IVa) or (IVb):

(IVa)

(IVb)

a tautomer thereof, or a pharmaceutically acceptable salt thereof,
wherein:
$R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl;
$R^5$ is selected from halogen, CN, $CF_3$, $OR^6$, an optionally substituted aryl, and an optionally substituted $C_1$-$C_6$ alkyl;

R[6] is selected from hydrogen, an optionally substituted $C_1$-$C_6$ alkyl, an optionally substituted aryl, and an optionally substituted heteroaryl; and R[9] is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

14. The method of claim 1, wherein the compound is selected from the group consisting of:

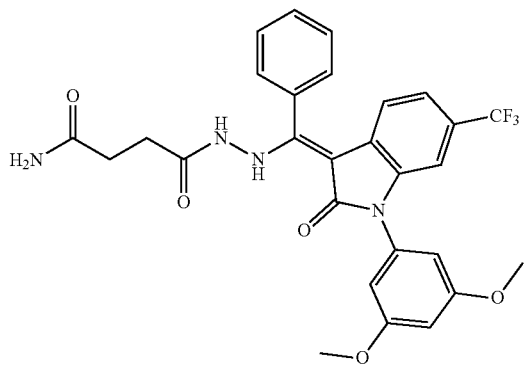

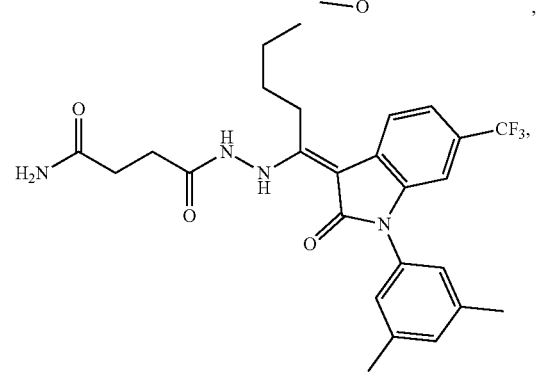

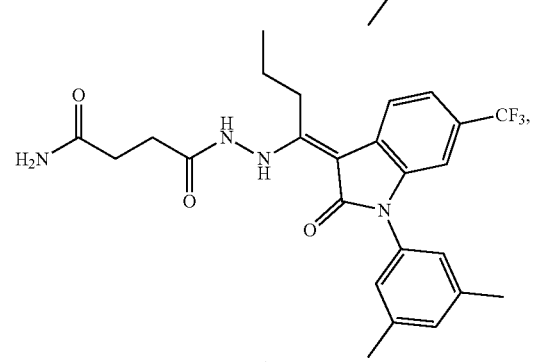

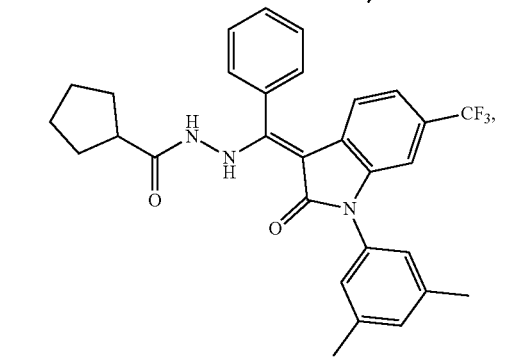

-continued

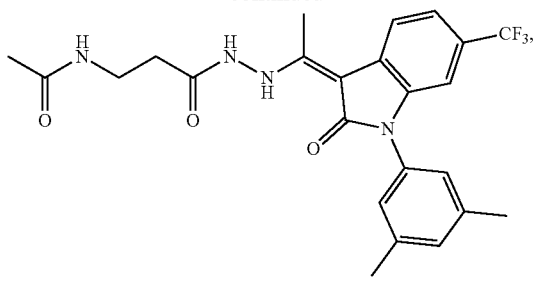

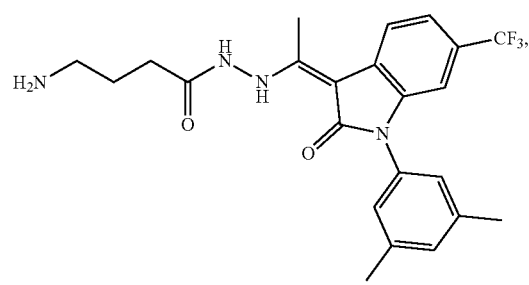

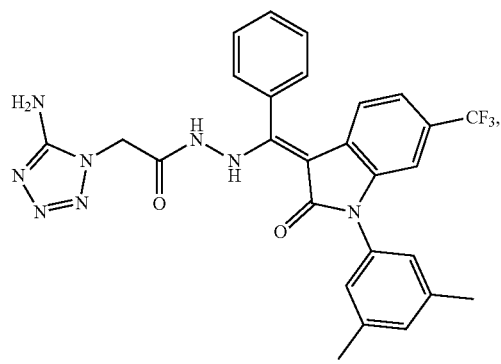

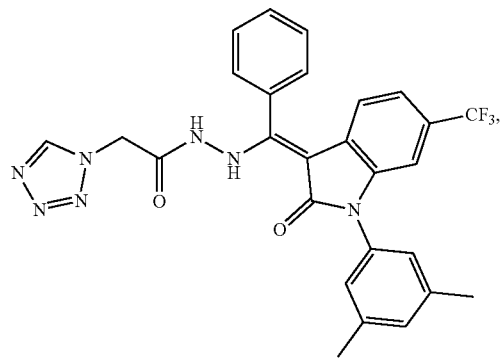

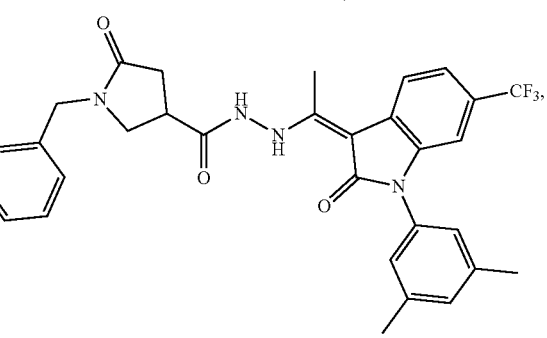

91
-continued
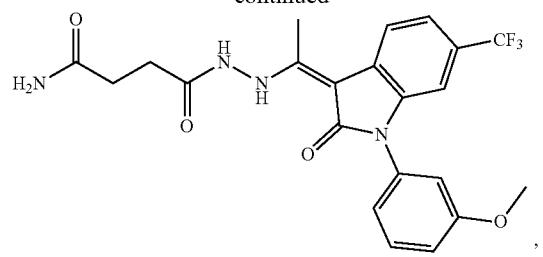
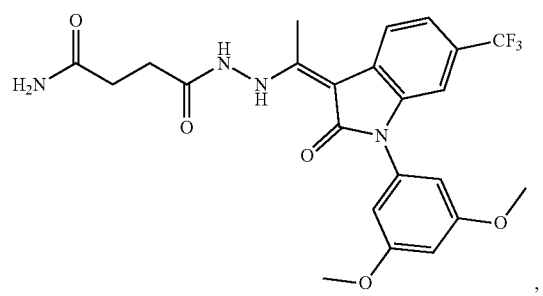
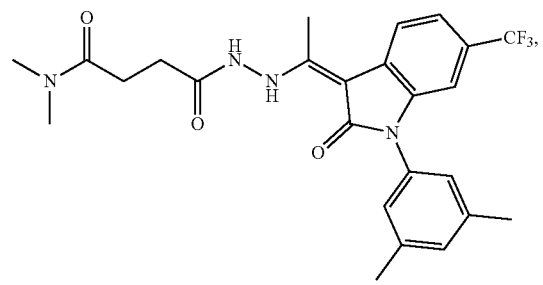
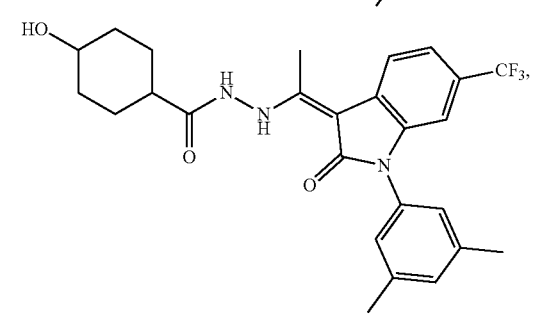
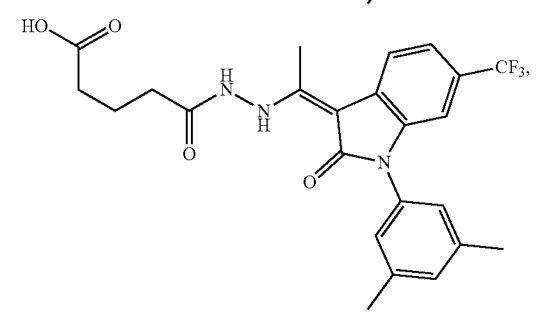
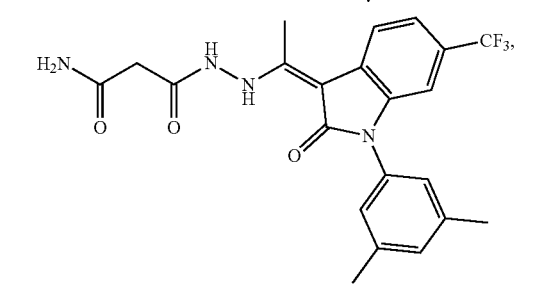
92
-continued
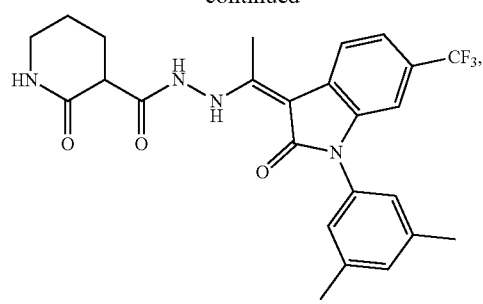
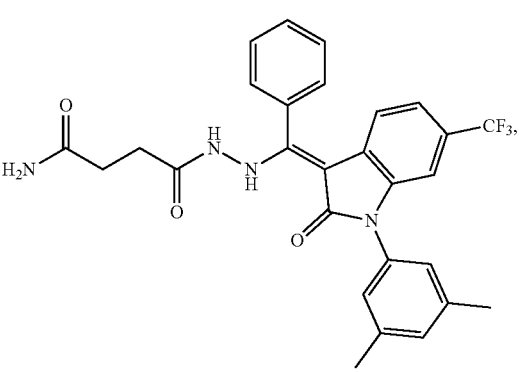
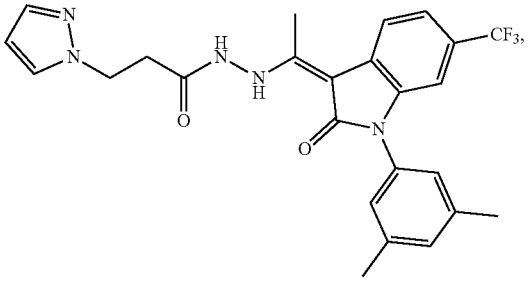
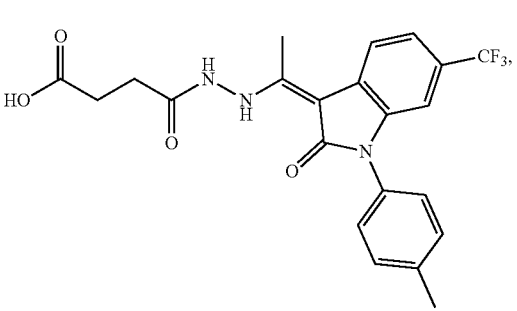
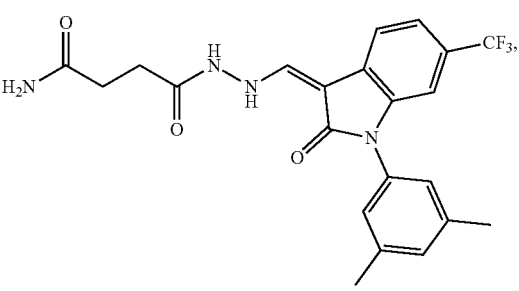

-continued
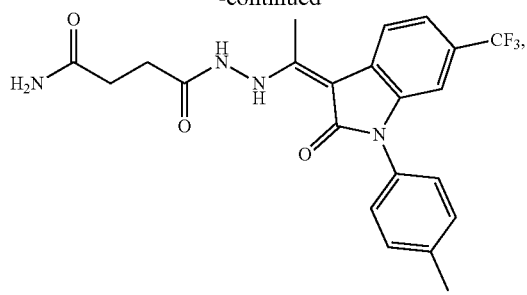
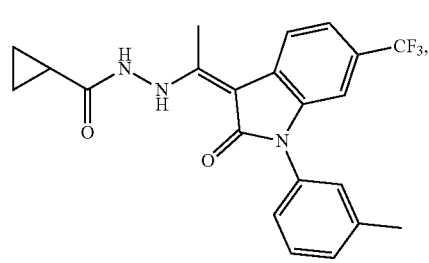
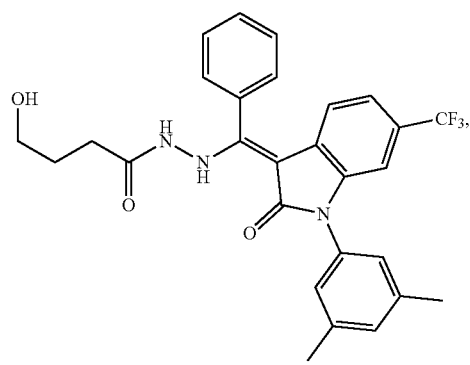
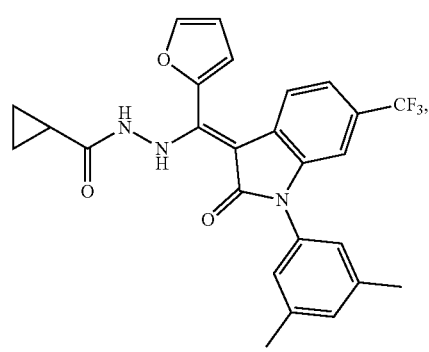
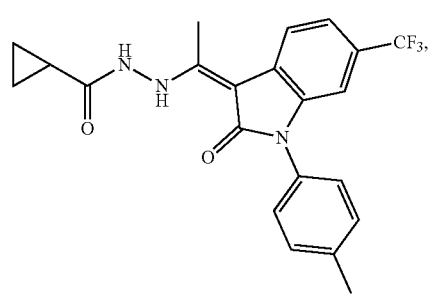
-continued
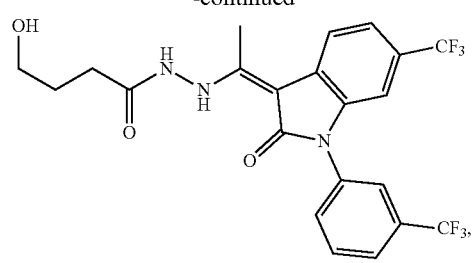
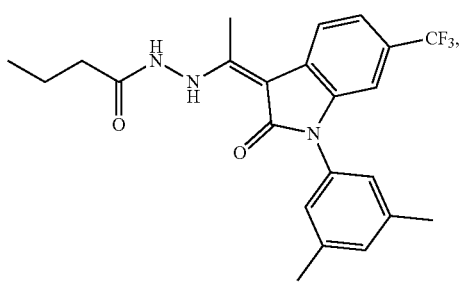
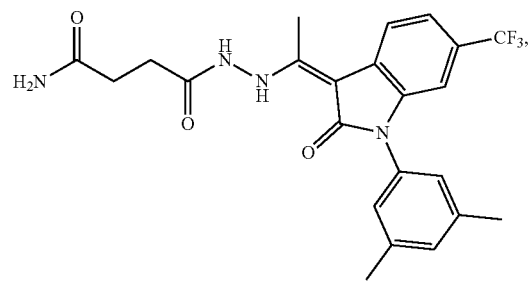
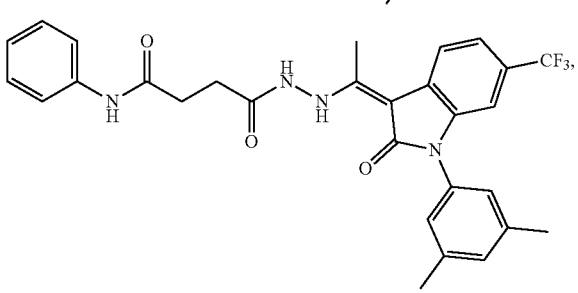
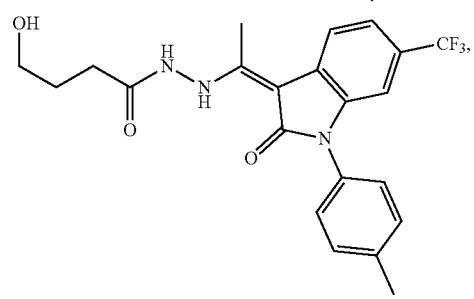
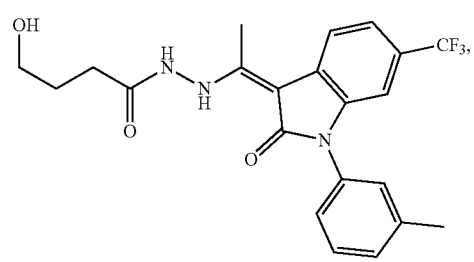

95
-continued
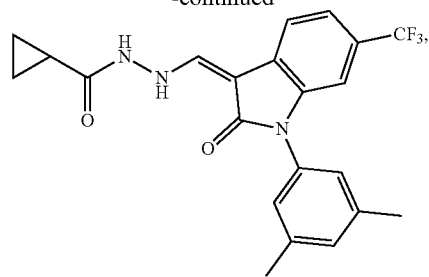
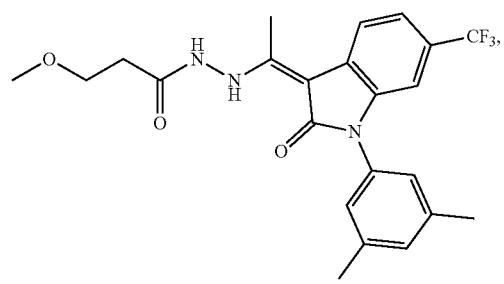
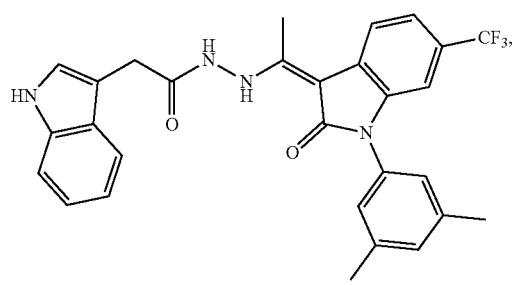
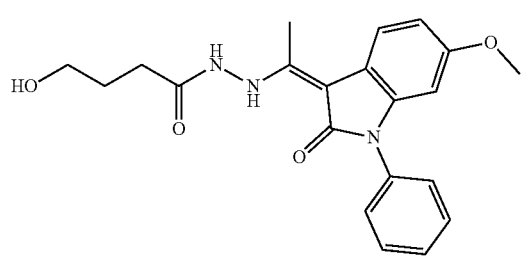
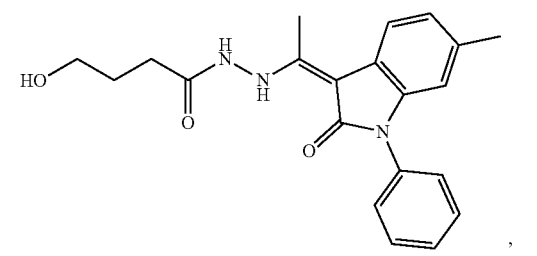
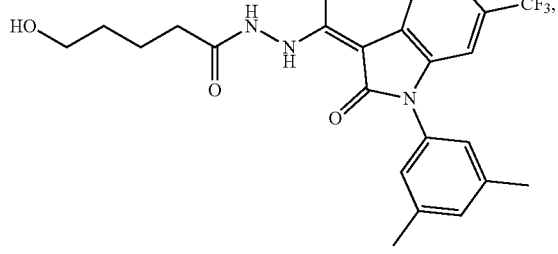
96
-continued
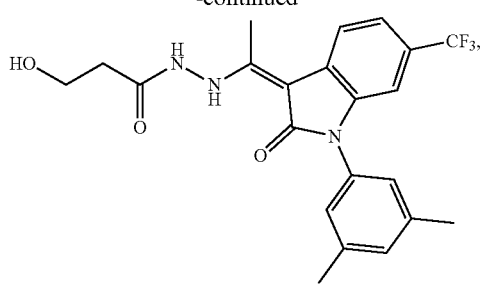
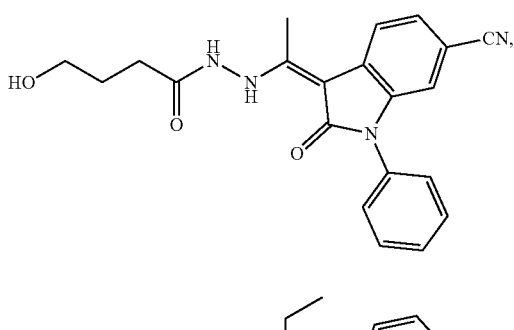
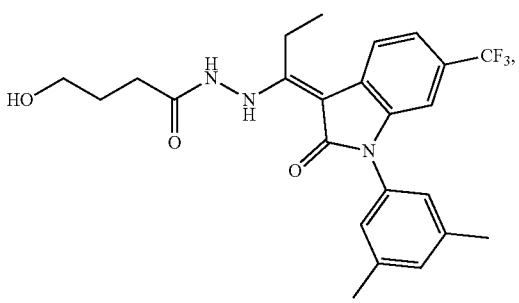
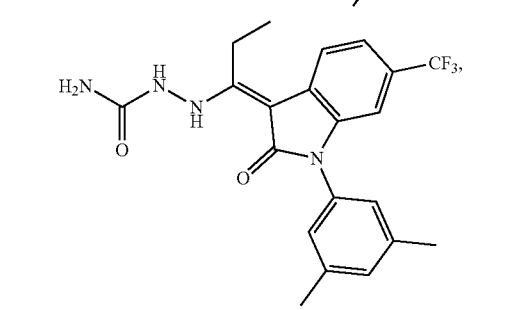
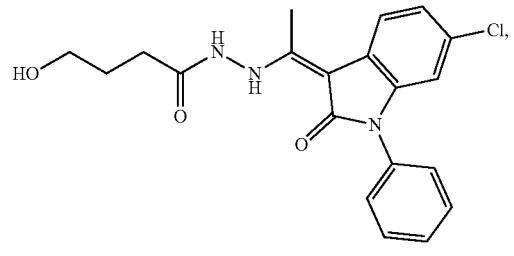
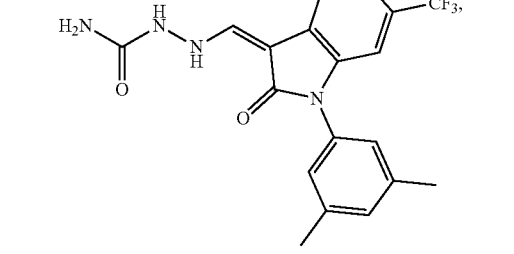

97
-continued
98
-continued
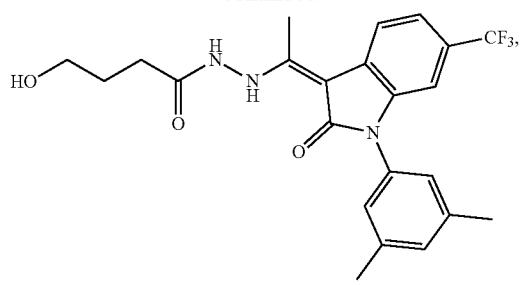
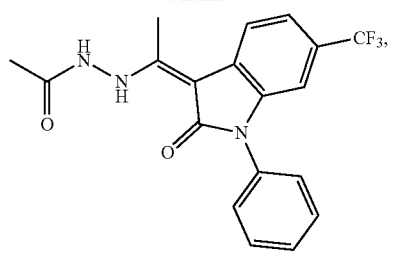
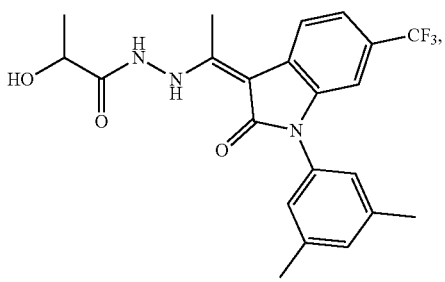
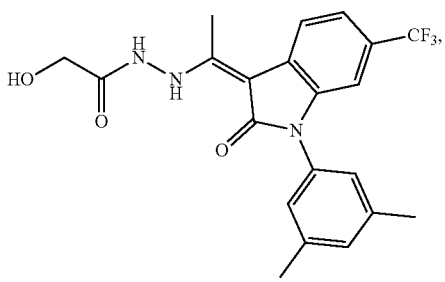
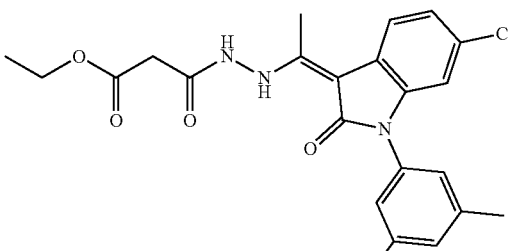
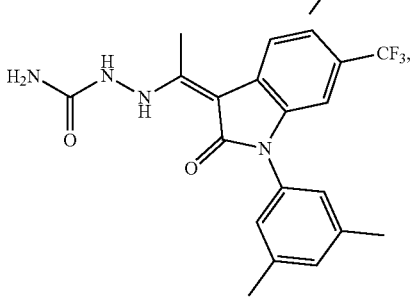
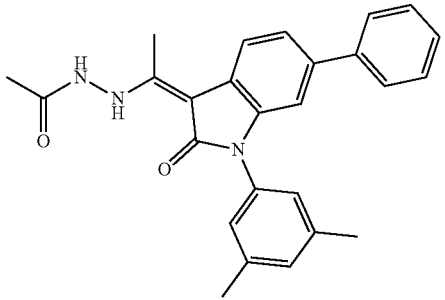

99
-continued
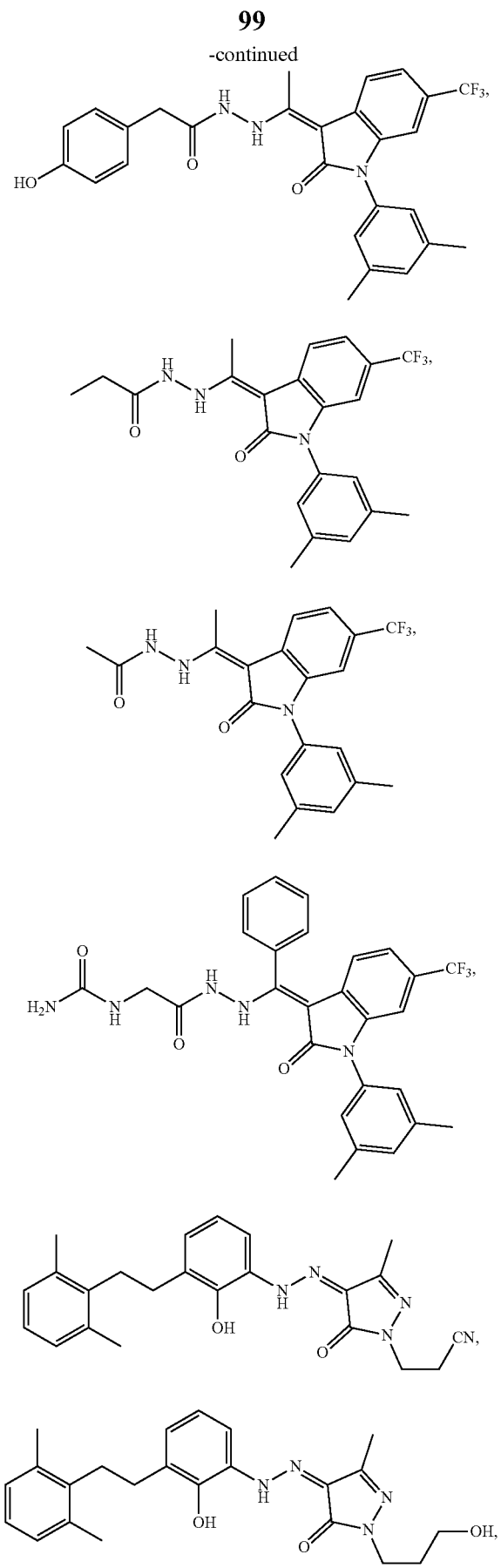
100
-continued
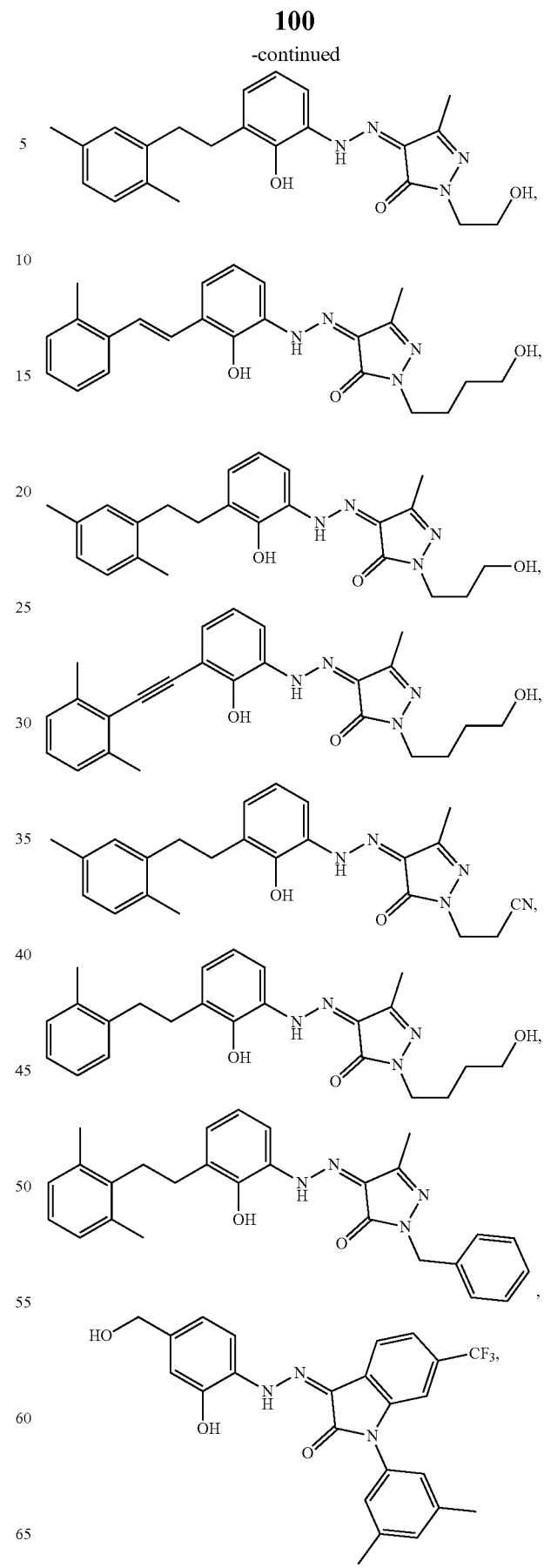

101
-continued
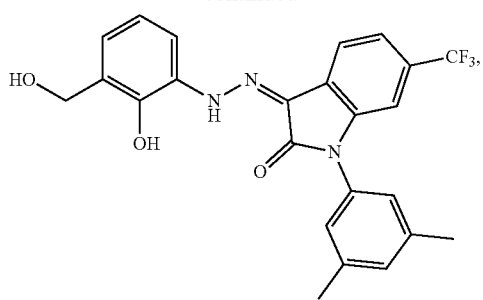
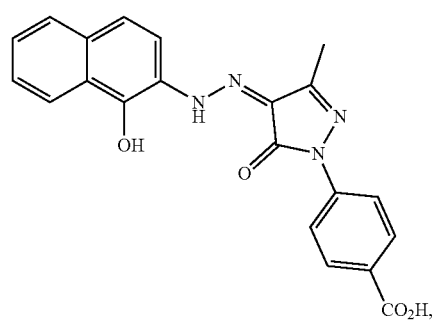
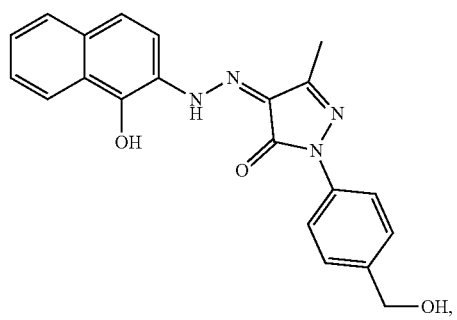
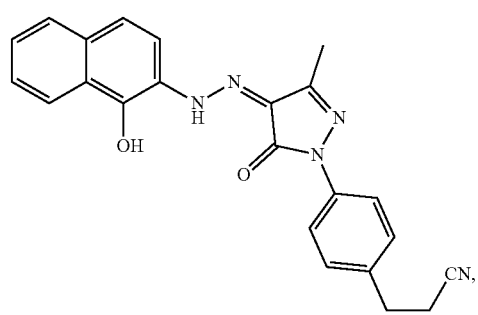
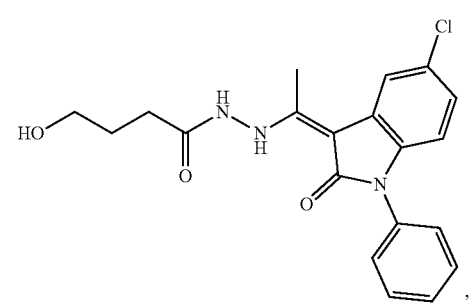
102
-continued
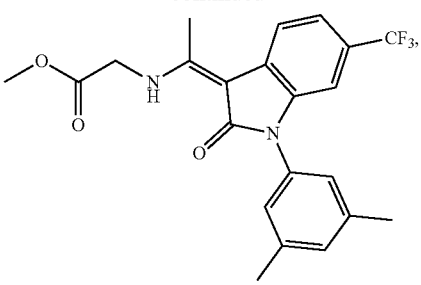
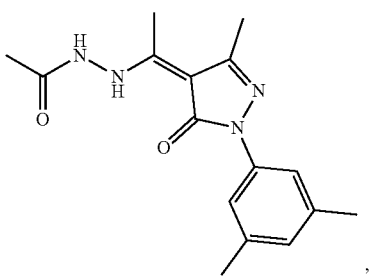
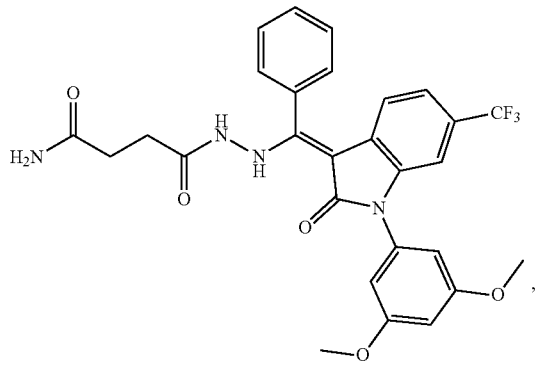
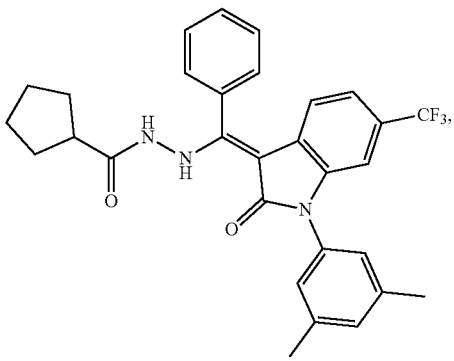
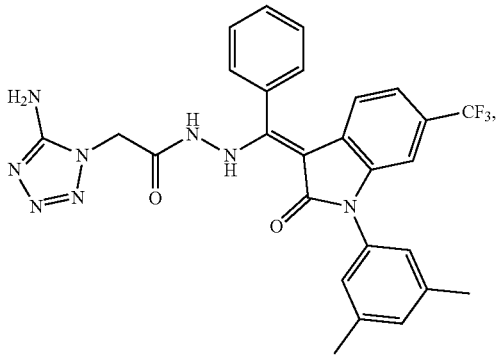

-continued
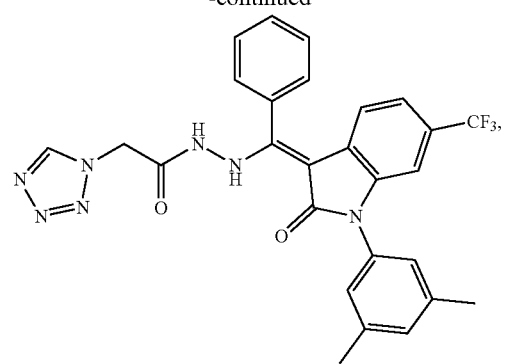
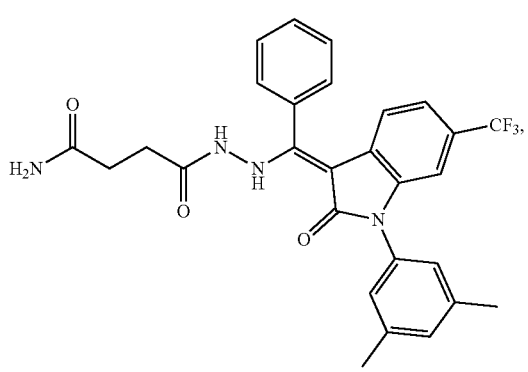
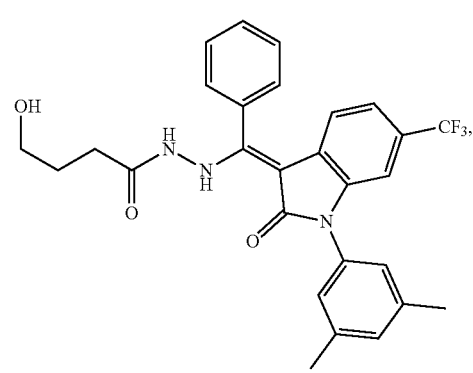
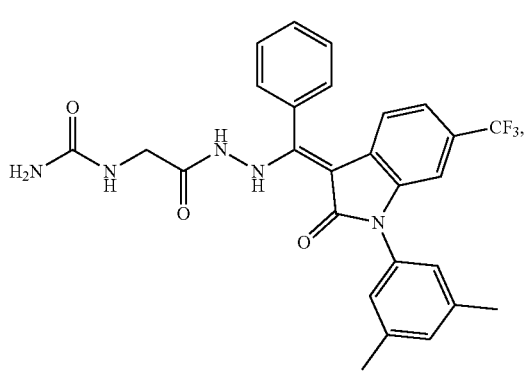
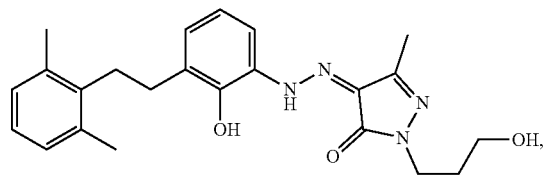
-continued
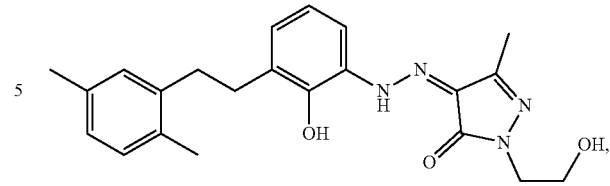
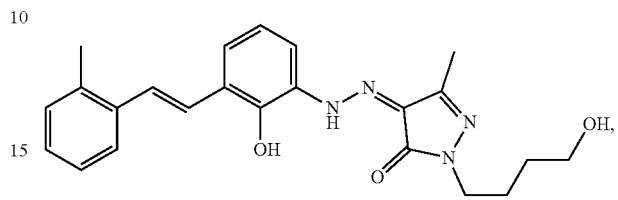
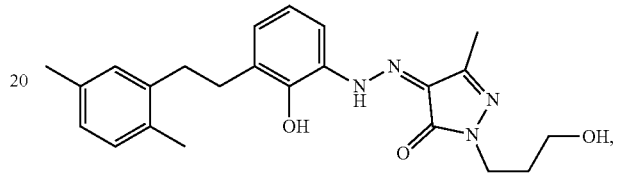
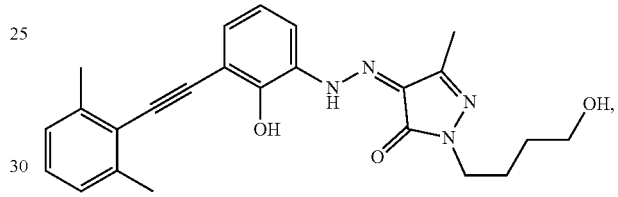
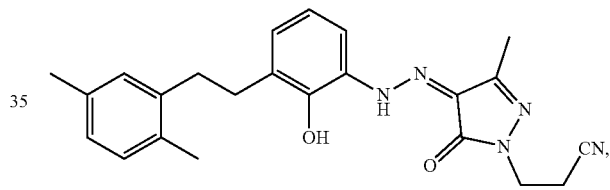
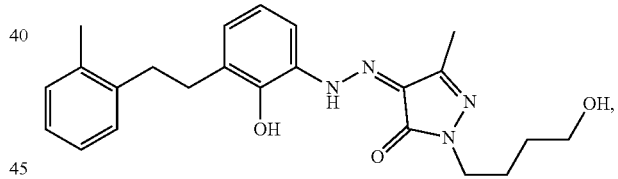
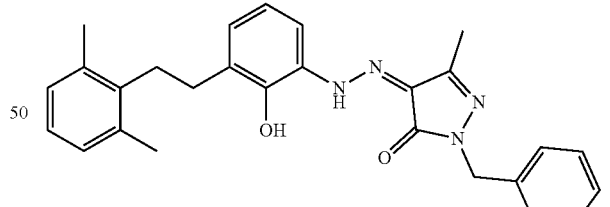
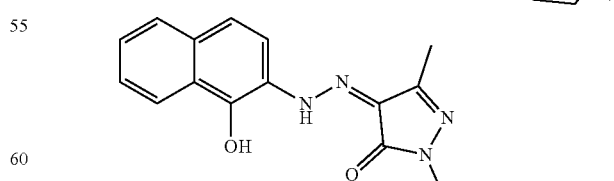

105
-continued
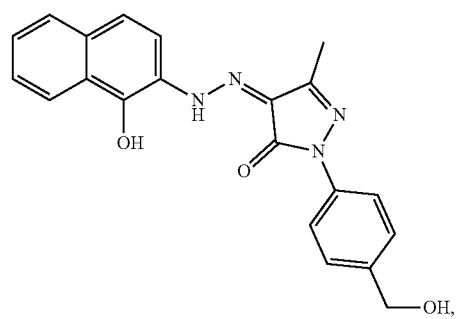
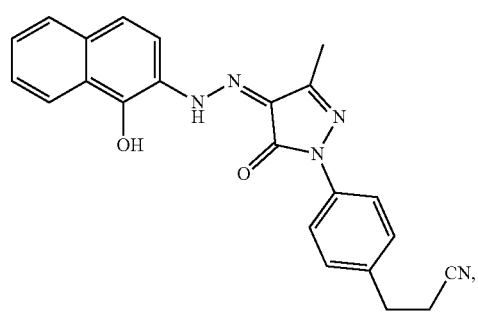
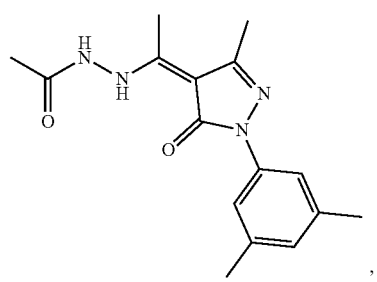
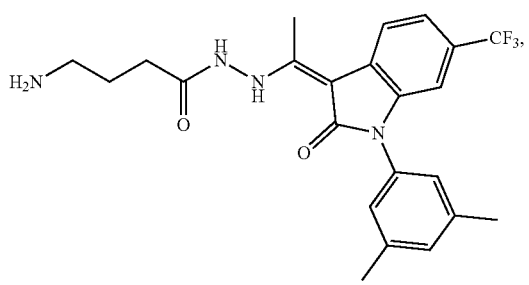
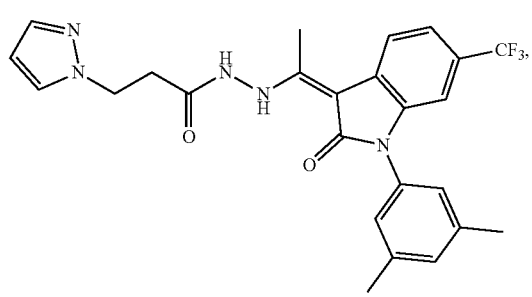
106
-continued
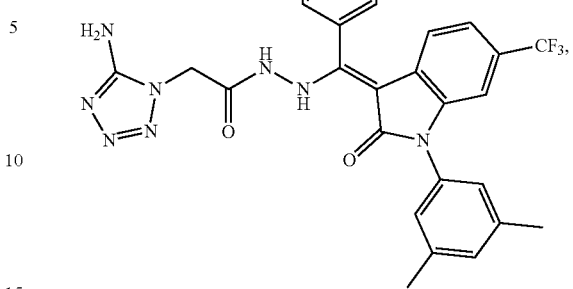
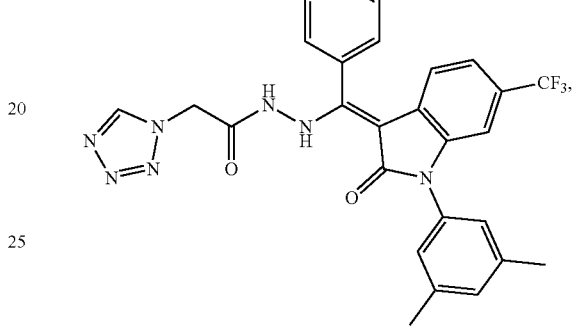
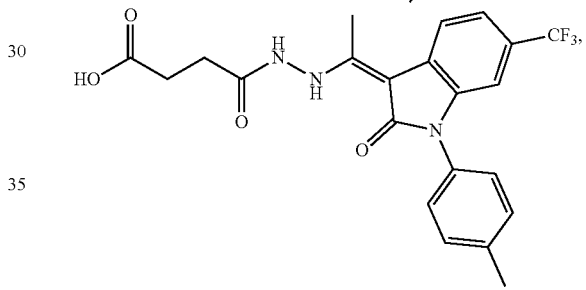
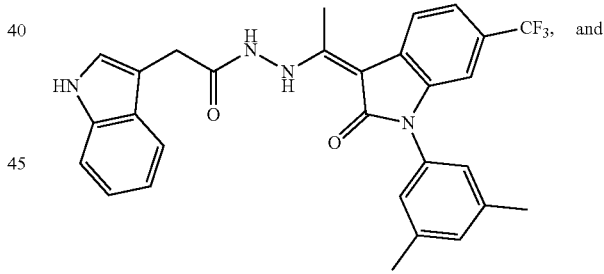 and
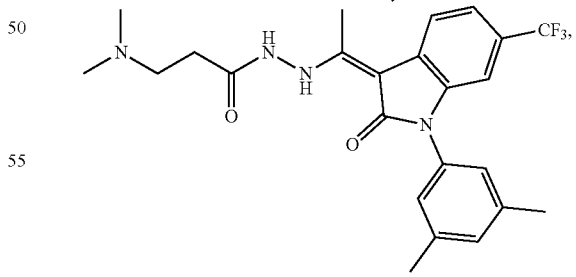
a tautomer thereof, or pharmaceutically acceptable salt thereof.
* * * * *

UNITED STATES PATENT AND TRADEMARK OFFICE
CERTIFICATE OF CORRECTION

PATENT NO. : 10,420,748 B2  
APPLICATION NO. : 15/908504  
DATED : September 24, 2019  
INVENTOR(S) : Keith B. Marschke et al.

It is certified that error appears in the above-identified patent and that said Letters Patent is hereby corrected as shown below:

On the Title Page

On Page 2, Column 1, Item (56), Line 15, under Other Publications, delete "thrombopoetin" and insert --thrombopoietin--.

On Page 2, Column 1, Item (56), Line 23, under Other Publications, delete "Classificiaton" and insert --Classification--.

On Page 2, Column 1, Item (56), Line 24, under Other Publications, delete "Fene" and insert --Gene--.

On Page 2, Column 2, Item (56), Line 10, under Other Publications, delete "Rolse" and insert --Role--.

On Page 2, Column 2, Item (56), Line 14, under Other Publications, delete "cycteine" and insert --cysteine--.

On Page 2, Column 2, Item (56), Line 16, under Other Publications, delete "Bioloigcal" and insert --Biological--.

On Page 2, Column 2, Item (56), Line 18, under Other Publications, delete "cycteine" and insert --cysteine--.

On Page 2, Column 2, Item (56), Line 42, under Other Publications, delete "Aalts:" and insert --Salts:--.

In the Specification

In Column 1, Line 39, delete "hematopietic" and insert --hematopoietic--.

Signed and Sealed this  
Eleventh Day of February, 2020

Andrei Iancu  
*Director of the United States Patent and Trademark Office*

CERTIFICATE OF CORRECTION (continued)

In Column 1, Line 63, delete "cycteine" and insert --cysteine--.

In Column 4, Line 14, delete "Alemtuzumab" and insert --Alemtuzumab.--.

In Column 4, Line 27 (Approx.), delete "cytotoxicity" and insert --cytotoxicity.--.

In Column 6, Line 65, delete "$C_3$-$C_6$" and insert --$C_3$-$C_8$--.

In Column 7, Line 2, delete "$C_3$-$C_6$" and insert --$C_3$-$C_8$--.

In Column 7, Line 3, delete "$C_3$-$C_6$" and insert --$C_3$-$C_8$--.

In Column 29, Lines 22-34 (Approx.), delete " 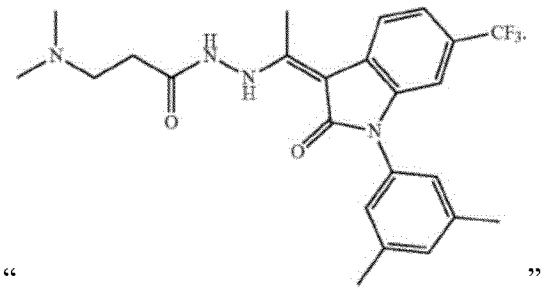 "

and insert -- 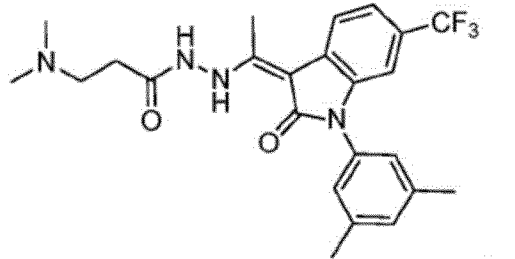 ,--.

In Column 30, Line 64, delete "and or" and insert --and/or--.

In Column 32, Lines 10-11, delete "norbomyl," and insert --norbornyl,--.

In Column 32, Line 30, delete "norbomylenyl," and insert --norbornylenyl,--.

In Column 33, Line 8, delete "Carbocylic" and insert --Carbocyclic--.

In Column 33, Lines 60-65, delete "Heteroatoms........the others." and insert the same in Column 33, Line 59 as the continuation of same paragraph.

In Column 34, Line 64, delete "t-electron" and insert --$\pi$-electron--.

In Column 49, Line 15, delete "heteroaryl; and" and insert --heteroaryl;--.

In Column 60, Lines 60-67 (Approx.), after " 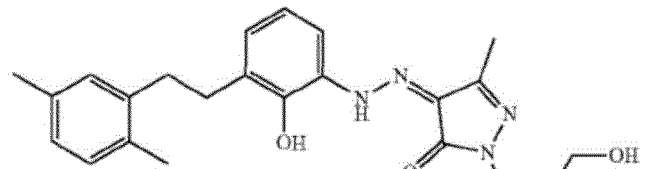 " insert --,--.

In Column 66, Line 43 (Approx.), delete "from" and insert --from:--.

In Column 68, Line 37, delete "subaceatate," and insert --subacetate,--.

In Column 77, Line 5, delete "somatostan," and insert --somatostatin,--.

In Column 77, Line 20, delete "hematopietic" and insert --hematopoietic--.

In Column 81, Line 3, delete "istep Kit" and insert --1step Kit--.

In Column 81, Line 10, delete "100 tiM." and insert --100 µM.--.

In Column 81, Line 63, delete "1 step Kit." and insert --1step Kit.--.

In Column 82, Line 14 (Approx.), delete "istep Kit." and insert --1step Kit.--.

In the Claims

In Column 83, Line 18 (Approx.), Claim 1, delete "Ill," and insert --(III),--.

In Column 83, Line 22 (Approx.), Claim 1, delete "Ill," and insert --(III),--.

In Column 84, Line 55, Claim 1, delete "$C_1C_6$" and insert --$C_1$-$C_6$--.

In Column 103, Lines 15-30 (Approx.), Claim 14, delete " 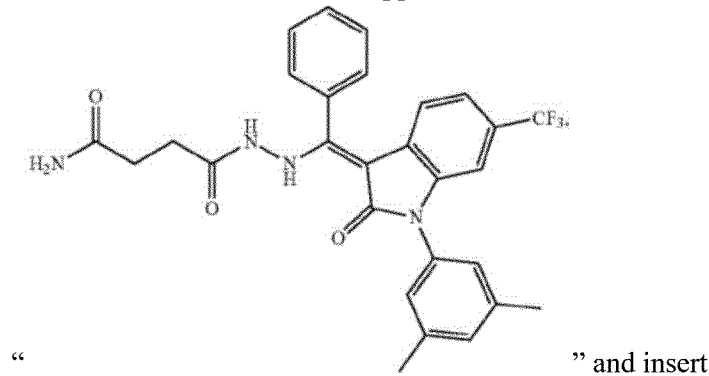 " and insert

CERTIFICATE OF CORRECTION (continued)
U.S. Pat. No. 10,420,748 B2

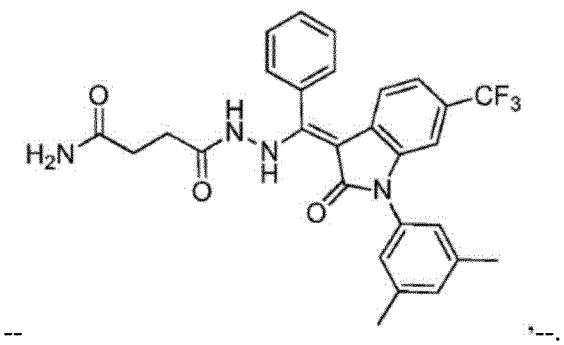

-- *--.